(12) United States Patent
Tounge et al.

(10) Patent No.: US 11,319,290 B2
(45) Date of Patent: *May 3, 2022

(54) SUBSTITUTED 3-DIALKYLAMINOMETHYL-PIPERIDIN-4-YL-BENZAMIDES AND METHODS OF MAKING AND USING SAME

(71) Applicant: MEBIAS DISCOVERY, INC., Philadelphia, PA (US)

(72) Inventors: Brett A. Tounge, Blue Bell, PA (US); Shariff Bayoumy, North Wales, PA (US); Lawrence C. Kuo, Gwynedd Valley, PA (US); Scott L. Dax, Landenberg, PA (US)

(73) Assignee: Mebias Discovery, Inc., Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/025,665

(22) Filed: Sep. 18, 2020

(65) Prior Publication Data

US 2021/0101868 A1    Apr. 8, 2021

Related U.S. Application Data

(63) Continuation of application No. 16/477,817, filed as application No. PCT/US2018/014090 on Jan. 17, 2018, now Pat. No. 10,836,728.

(60) Provisional application No. 62/599,834, filed on Dec. 18, 2017, provisional application No. 62/447,197, filed on Jan. 17, 2017.

(51) Int. Cl.
| | |
|---|---|
| *C07D 221/00* | (2006.01) |
| *A61P 23/00* | (2006.01) |
| *C07D 401/06* | (2006.01) |
| *C07D 409/06* | (2006.01) |
| *C07D 211/08* | (2006.01) |
| *A61K 31/445* | (2006.01) |

(52) U.S. Cl.
CPC .......... *C07D 221/00* (2013.01); *A61K 31/445* (2013.01); *A61P 23/00* (2018.01); *C07D 211/08* (2013.01); *C07D 401/06* (2013.01); *C07D 409/06* (2013.01)

(58) Field of Classification Search
CPC ................ C07D 221/00; C07D 211/08; C07D 401/06; C07D 409/06; A61P 23/00; A61K 31/445

See application file for complete search history.

(56) References Cited

U.S. PATENT DOCUMENTS

| | | |
|---|---|---|
| 5,202,345 A | 4/1993 | Matsumura et al. |
| 6,387,949 B1 | 5/2002 | Delorme et al. |
| 6,900,196 B2 | 5/2005 | Liebeschuetz et al. |
| 7,049,327 B2 | 5/2006 | Sattlegger et al. |
| 7,244,866 B2 | 7/2007 | Carson et al. |
| 7,368,444 B2 | 5/2008 | Seko et al. |
| 7,745,492 B2 | 6/2010 | Carson et al. |
| 7,884,102 B2 | 2/2011 | Dolle et al. |
| 2004/0048797 A1 | 3/2004 | Miller et al. |
| 2004/0127516 A1 | 7/2004 | Sattlegger et al. |
| 2004/0204453 A1 | 10/2004 | McHardy et al. |
| 2008/0306071 A1 | 12/2008 | Dolle et al. |
| 2011/0237622 A1 | 9/2011 | Chen et al. |

FOREIGN PATENT DOCUMENTS

| | | |
|---|---|---|
| CN | 105646332 A | 6/2016 |
| JP | 2000344746 A | 12/2000 |
| JP | 2002524445 A | 8/2002 |
| WO | 2004089370 A1 | 10/2004 |
| WO | 2015091939 A1 | 6/2015 |

OTHER PUBLICATIONS

International Search Report and Written Opinion, dated Mar. 26, 2018, PCT/US2018/014090.
Supplemental European Search Report, Application No. 18741698.7, dated Dec. 15, 2020.

*Primary Examiner* — Alicia L Otton
(74) *Attorney, Agent, or Firm* — Saul Ewing Arnstein & Lehr LLP; Kathryn Doyle; Domingos J. Silva

(57) ABSTRACT

The invention relates to certain substituted 3-dialkylaminomethyl-piperidin-4-yl-benzamides, and compositions comprising the same, which in certain embodiments are useful for treating and/or preventing pain in a subject in need thereof.

23 Claims, 6 Drawing Sheets

Specification includes a Sequence Listing.

Crystal structure of 4b *Ent*-B-*syn*

SUBSTITUTED 3-DIALKYLAMINOMETHYL-PIPERIDIN-4-YL-BENZAMIDES AND METHODS OF MAKING AND USING SAME

CROSS REFERENCE TO RELATED APPLICATIONS

The present application is a continuation of, and claims priority to, U.S. patent application Ser. No. 16/477,817, filed Jul. 12, 2019, now issued as U.S. Pat. No. 10,836,728, which is a 35 U.S.C. § 371 national phase application of, and claims priority to, International Application No. PCT/US2018/014090, filed Jan. 17, 2018, which claims priority under 35 U.S.C. § 119(e) to U.S. Provisional Patent Application No. 62/447,197, filed Jan. 17, 2017, and U.S. Provisional Patent Application No. 62/599,834, filed Dec. 18, 2017, all of which applications are incorporated herein by reference in their entireties.

BACKGROUND OF THE INVENTION

Pain is defined as an unpleasant sensory and emotional experience. Pain, however, can be informative and useful. Nociceptive pain is often indicative of injury (e.g., tissue damage), and such pain typically evokes escape or protective behaviors in animals, including humans. However, inflammation, cellular and neuronal damage and other processes resulting from injury or disease can lead to states of chronic pathological pain. Hyperalgesia is a condition in which enhanced sensitivity to noxious stimuli is present, and thus the perception of pain is exaggerated. Allodynia is a condition in which normally non-noxious stimuli become painful. Persistent or chronic pain, manifested as hyperalgesia and/or allodynia, remains challenging to treat. Chronic pain contributes to over $600 billion worth of healthcare expenditures annually, more than the yearly cost of cancer, heart disease, and diabetes combined. Neuropathic pain affects about 6-10% of the population, and is associated with decreased quality of life and socioeconomic burdens exceeding all other chronic pain disorders. Many patients do not respond to existing therapeutics, have their pain poorly managed (i.e., inadequate relief), or experience relief for an inadequate duration.

The administration of opioids to treat pain is a well-recognized and commonly employed therapy in medicine. Mu opioids from natural sources have used by humans for millennia for a wide variety of purposes, including the relief of dysentery and pain. Opium alkaloids were not isolated until the 1800s, and synthetic opioids, structural alterations of naturally-occurring precursors or newly designed molecules, came much later. Agonists of the Mu opioid receptor (MOR) are the standard analgesic agents to treat acute, severe pain conditions in humans. Furthermore, the ineffectiveness of non-opioid agents to manage chronic pain states, such as pain caused by cancer, often leaves few options other than to extend the duration of opioid treatment beyond acute applications.

Unfortunately, tachyphylaxis and tolerance to opioids and opioid-induced hyperalgesia often result during the course of therapy. In such patients, increasingly higher doses of opioids are needed to provide an acceptable level of pain relief and, in doing so, the patient is thereby subjected to a higher risk of additional adverse side effects and safety concerns, which include respiratory depression, constipation, nausea and vomiting. Prolonged opioid therapy to treat chronic pain states may subject the patient to develop dependence on opioids, suffer opioid withdrawal on discontinuation of treatment, and some patients may be more susceptible to engage in abuse of these medications. These phenomena present significant clinical challenges for the treatment of pain.

G-Protein coupled receptors are membrane-bound proteins that contain seven transmembrane domains, an extracellular N-terminus, intracellular loops and an intracellular C-terminus. The GPCR family constitutes the largest class of cell surface receptors in the human genome (about 800 different members), and small molecules that modulate GPCRs account for nearly one-third of all marketed drugs.

Historically, from a conceptual perspective, GPCRs were thought to behave as switches (off/on), whereupon agonist binding induces a conformational change to recruit G-protein coupling, thereby producing second-messengers such as cAMP to alter cellular functions [e.g., polarization (neurons), contractility (myocytes), transcription, translation, and so forth]. Antagonists block agonist access, thereby providing a means to prevent GPCR activation, which is also useful therapeutically depending upon the specific GPCR.

Upon ligand binding, GPCRs not only interact with G-proteins as described above, but also recruit cytosolic proteins of the arrestin family. Arrestin recruitment occurs as a result of phosphorylation by a family of G-protein receptor kinases (GRKs). One apparent role of the β-arrestin pathway is to turn off signaling, possibly serving as an evolutionary 'brake' to avoid deleterious effects of extended constitutive signaling. β-Arrestins accomplish signal termination in several ways: (1) G-protein uncoupling causes desensitization (loss of signaling); (2) degradation of the second messenger(s) turns down/off signaling; and (3) receptor internalization precludes agonist binding and signaling since the receptor is not exposed/present on the cell membrane. Furthermore, there are other signaling modalities (e.g., MAP kinase) that can be activated by β-arrestins.

Thus GPCR ligands that can behave in a "biased" (i.e., "signaling pathway-selective") manner by activating either G-protein or β-arrestin pathways (but not both), offer an opportunity to develop new therapeutics that retain efficacy but are devoid of adverse effects. The βarrestin pathway is responsible for many of the adverse effects caused by the classic mu opioid drugs. Thus there is a need to develop mu opioid agonists that are biased towards activating the G-protein pathway. Furthermore, there is a need in the art for novel compounds and/or compositions that can be used to treat pain and/or reduce hyperalgesia and allodynia. In certain embodiments, the compounds and/or compositions do not induce significant (or any at all) respiratory depression, constipation, and/or tolerance, while providing pain relief. The present invention addresses these unmet needs.

BRIEF SUMMARY OF THE INVENTION

The invention provides certain compounds of the invention. The invention further provides a pharmaceutical composition comprising at least one pharmaceutically acceptable carrier and at least one compound of the invention. The invention further provides a method of treating and/or preventing pain in a subject.

In certain embodiments, the method comprises administering to the subject a therapeutically effective amount of at least one compound of the invention and/or at least one pharmaceutical composition of the invention.

In certain embodiments, the compound of the invention is the compound of formula (I):

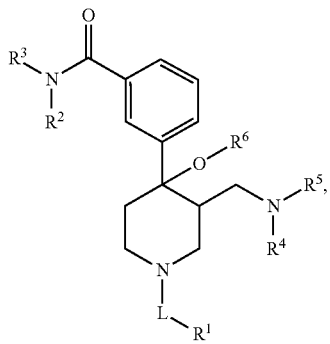

(I)

wherein: L is selected from the group consisting of —(CZ$^1$Z$^2$)—, —(CZ$^1$Z$^2$—CZ$^1$Z$^2$)—, and —(CZ$^1$Z$^2$—CZ$^1$Z$^2$—CZ$^1$Z$^2$)—; R$^1$ is selected from the group consisting of

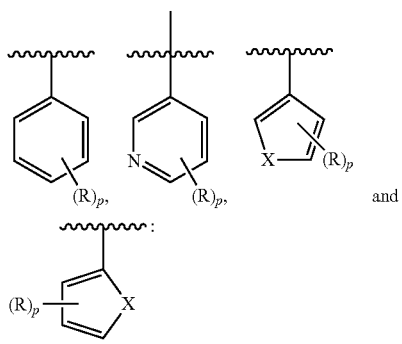

R$^2$ is selected from the group consisting of hydrogen, C$_1$-C$_6$ alkyl, and substituted C$_1$-C$_6$ alkyl; R$^3$ is selected from the group consisting of hydrogen, methyl and ethyl; R$^4$ is selected from the group consisting of methyl and ethyl; R$^5$ is selected from the group consisting of methyl and ethyl; R$^6$ is selected from the group consisting of H and C$_1$-C$_6$ alkyl; each occurrence of Z$^1$ and Z$^2$ is independently selected from the group consisting of hydrogen, fluoro, and methyl; X is selected from the group consisting of S, O, and N—R$^7$; each occurrence of R is independently selected from the group consisting of hydrogen, fluoro, chloro, bromo, iodo, cyano, nitro, hydroxyl, C$_1$-C$_6$ alkoxy, C$_1$-C$_6$ alkyl, substituted C$_1$-C$_6$ alkyl, C$_2$-C$_6$ alkenyl, substituted C$_2$-C$_6$ alkenyl, alkynyl, substituted C$_2$-C$_6$ alkynyl, phenyl, substituted phenyl, —COOR$^7$, and carboxamide; or -L-R$^1$ combine to form H, C$_1$-C$_6$ alkyl, or substituted C$_1$-C$_6$ alkyl; each occurrence of p is independently selected from the group consisting of 0, 1, 2 and 3; and each occurrence of R$^7$ is independently selected from the group consisting of hydrogen and C$_1$-C$_6$ alkyl, or a salt, solvate, enantiomer, diastereoisomer and/or tautomer thereof, and any mixtures thereof.

In certain embodiments, R$^2$ and R$^3$ are H. In certain embodiments, R$^4$ and R$^5$ are methyl. In certain embodiments, R$^6$ is selected from the group consisting of H and methyl. In certain embodiments, L is selected from the group consisting of methylene (—CH$_2$—), 1,2-ethylene (—CH$_2$—CH$_2$—), and 1,3-propylene (—CH$_2$—CH$_2$—CH$_2$—). In certain embodiments, R$^1$ is selected from the group consisting of phenyl, thienyl, furanyl, 3-pyridinyl, substituted phenyl, substituted thienyl, substituted furanyl, and substituted 3-pyridinyl. In certain embodiments, R$^2$ and R$^3$ are H, R$^4$ and R$^5$ are methyl, R$^6$ is selected from the group consisting of H and methyl, L is selected from the group consisting of methylene (—CH$_2$—), 1,2-ethylene (—CH$_2$—CH$_2$—), and 1,3-propylene (—CH$_2$—CH$_2$—CH$_2$—), and R$^1$ is selected from the group consisting of phenyl, thienyl, furanyl, 3-pyridinyl, substituted phenyl, substituted thienyl, substituted furanyl, and substituted 3-pyridinyl. In certain embodiments, the —R$^6$ and —CH$_2$NR$^4$R$^5$ groups have syn relative stereochemistry.

In certain embodiments, the compound is selected from the group consisting of:

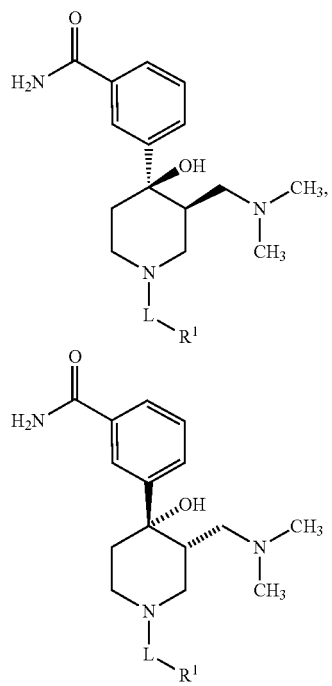

and any mixtures thereof.

In certain embodiments, the compound is at least one selected from the group consisting of: 3-(-(2-Chloro-4-fluoro-benzyl)-3-dimethylaminomethyl-4-hydroxy-piperidin-4-yl)-benzamide (6); (+)-Ent-A-syn-3-(1-(2-chloro-4-fluorobenzyl)-3-((dimethylamino) methyl)-4-hydroxy piperidin-4-yl)benzamide [(+)-Ent-A-syn-(6)]; (−)-Ent-B-syn-3-(1-(2-chloro-4-fluorobenzyl)-3-((dimethylamino) methyl)-4-hydroxy piperidin-4-yl)benzamide [(−)-Ent-B-syn-(6)]; (+)-Ent-A-anti-3-[1-(2-chloro-4-fluorobenzyl)-3-[(dimethylamino)methyl]-4-hydroxypiperidin-4-yl] benzamide [(+)-Ent-A-anti-(6)]; (−)-Ent-B-anti-3-[1-(2-chloro-4-fluorobenzyl)-3-[(dimethylamino)methyl]-4-hydroxypiperidin-4-yl]benzamide [(−)-Ent-B-anti-(6)]; 3-(3-Dimethylaminomethyl-4-hydroxy-1-thiophen-3-ylmethyl-piperidin-4-yl)-benzamide (11); (+)-Ent-A-syn-3-[3-[(dimethylamino)methyl]-4-hydroxy-1-[(thiophen-3-yl) methyl]piperidin-4-yl] benzamide [(+)-Ent-A-syn-(11)]; (−)-Ent-B-syn-3-[3-[(dimethylamino)methyl]-4-hydroxy-1-[(thiophen-3-yl)methyl]piperidin-4-yl] benzamide [(−)-Ent-B-syn-(11)]; (+)-Ent-A-anti-3-[3-[(dimethylamino)methyl]-4-hydroxy-1-[(thiophen-3-yl)methyl]piperidin-4-yl] benzamide [(+)-Ent-A-anti-(11)]; (−)-Ent-B-anti-3-[3-[(dimethylamino)methyl]-4-hydroxy-1-[(thiophen-3-yl)methyl]

piperidin-4-yl] benzamide [(−)-Ent-B-anti-(11)]; 3-{3-[(dimethylamino)methyl]-1-[(5-fluoropyridin-3-yl)methyl]-4-hydroxypiperidin-4-yl} benzamide; 3-[(3S,4R)-3-Dimethylaminomethyl-1-(5-fluoro-pyridin-3-ylmethyl)-4-hydroxy-piperidin-4-yl]-benzamide (29a); 3-[(3R,4S)-3-Dimethylamino methyl-1-(5-fluoro-pyridin-3-ylmethyl)-4-hydroxy-piperidin-4-yl]-benzamide (29b); (+)-Ent-A-anti-3-[(dimethylamino)methyl]-1-[(5-fluoropyridin-3-yl)methyl]-4-hydroxypiperidin-4-yl]benzamide; (−)-Ent-B-anti-3-[3-[(dimethylamino)methyl]-1-[(5-fluoropyridin-3-yl)methyl]-4-hydroxypiperidin-4-yl]benzamide; 3-(3-Dimethylaminomethyl-4-hydroxy-1-phenethyl-piperidin-4-yl)-benzamide (9); (+)-Ent-A-syn-3-[3-[(dimethylamino)methyl]-4-hydroxy-1-(2-phenylethyl)piperidin-4-yl] benzamide (45a); (−)-Ent-B-syn-3-[3-[(dimethylamino)methyl]-4-hydroxy-1-(2-phenylethyl)piperidin-4-yl] benzamide (45b); (+)-Ent-A-anti-3-[3-[(dimethylamino)methyl]-4-hydroxy-1-(2-phenylethyl)piperidin-4-yl] benzamide [(+)-Ent-A-anti-(9)]; (−)-Ent-B-anti-3-[3-[(dimethylamino)methyl]-4-hydroxy-1-(2-phenylethyl) piperidin-4-yl]benzamide [(−)-Ent-B-anti-(9)]; 3-(1-(2-Chloro-4-fluorophenethyl)-3-((dimethylamino)methyl)-4-hydroxypiperidin-4-yl) benzamide (13); 3-((3S,4R)-1-(2-Chloro-4-fluorophenethyl)-3-((dimethylamino)methyl)-4-hydroxypiperidin-4-yl)benzamide (32a); 3-((3R,4S)-1-(2-Chloro-4-fluorophenethyl)-3-((dimethylamino)methyl)-4-hydroxypiperidin-4-yl)benzamide (32b); (+)-Ent-A-anti-3-[1-[2-(2-chloro-4-fluorophenyl)ethyl]-3-[(dimethylamino)methyl]-4-hydroxypiperidin-4-yl]benzamide [(+)-Ent-A-anti-(13)]; (−)-Ent-B-anti-3-[1-[2-(2-chloro-4-fluorophenyl)ethyl]-3-[(dimethylamino) methyl]-4-hydroxypiperidin-4-yl]benzamide [(−)-Ent-B-anti-(13)]; 3-(3-((Dimethylamino)methyl)-4-hydroxy-1-(4-methoxyphenethyl)piperidin-4-yl) benzamide (17); (+)-Ent-A-syn-3-(3-((dimethylamino)methyl)-4-hydroxy-1-(4-methoxyphenethyl)piperidin-4-yl) benzamide [(+)-Ent-A-syn-(17)]; (−)-Ent-B-syn-3-(3-((dimethylamino)methyl)-4-hydroxy-1-(4-methoxyphenethyl)piperidin-4-yl)benzamide [(−)-Ent-B-syn-(17)]; (+)-Ent-A-anti-3-(3-((dimethylamino)methyl)-4-hydroxy-1-(4-methoxyphenethyl)piperidin-4-yl)benzamide [(+)-Ent-A-anti-(17)]; (−)-Ent-B-anti-3-(3-((dimethylamino)methyl)-4-hydroxy-1-(4-methoxyphenethyl)piperidin-4-yl)benzamide [(−)-Ent-B-anti-(17)]; 3-(3-((Dimethylamino) methyl)-4-hydroxy-1-(4-hydroxyphenethyl)piperidin-4-yl)benzamide (18); (+)-Ent-A-syn-3-[3-[(dimethylamino)methyl]-4-hydroxy-1-[2-(4-hydroxyphenyl)ethyl] piperidin-4-yl]benzamide (38a); (−)-Ent-B-syn-3-[3-[(dimethylamino)methyl]-4-hydroxy-1-[2-(4-hydroxyphenyl)ethyl] piperidin-4-yl]benzamide (38b); (+)-Ent-A-anti-3-[3-[(dimethylamino) methyl]-4-hydroxy-1-[2-(4-hydroxyphenyl)ethyl]piperidin-4-yl]benzamide [(+)-Ent-A-anti-(18)]; (−)-Ent-B-anti-3-[3-(dimethylamino)methyl]-4-hydroxy-1-[2-(4-hydroxyphenyl)ethyl] piperidin-4-yl]benzamide [(−)-Ent-B-anti-(18)]; 3-(3-((Dimethylamino)methyl)-4-hydroxy-1-(2-(thiophen-3-yl)ethyl) piperidin-4-yl)benzamide (15); 3-(3S,4R)-3-((Dimethylamino) methyl)-4-hydroxy-1-(2-(thiophen-3-yl) ethyl)piperidin-4-yl)benzamide (41a); 3-((3R,4S)-3-((Dimethylamino)methyl)-4-hydroxy-1-(2-(thiophen-3-yl) ethyl)piperidin-4-yl)benzamide_(41b); (+)-Ent-A-anti-3-[3-[(dimethylamino)methyl]-4-hydroxy-1-[2-(thiophen-3-yl) ethyl]piperidin-4-yl]benzamide [(+)-Ent-A-anti-(15)]; (−)-Ent-B-anti-3-[3-[(dimethylamino)methyl]-4-hydroxy-1-[2-(thiophen-3-yl)ethyl]piperidin-4-yl]benzamide [(−)-Ent-B-anti-(15)]; 3-[3-Dimethylaminomethyl-4-hydroxy-1-(3-phenyl-propyl)-piperidin-4-yl]-benzamide (20); (+)-Ent-A-syn-3-[3-[(dimethylamino)methyl]-4-hydroxy-1-(3-phenylpropyl) piperidin-4-yl]benzamide (44a); (−)-Ent-B-syn-3-[3-[(dimethylamino)methyl]-4-hydroxy-1-(3-phenyl-propyl)piperidin-4-yl]benzamide (44b); (+)-Ent-A-anti-3-[3-[(dimethylamino) methyl]-4-hydroxy-1-(3-phenylpropyl)piperidin-4-yl]benzamide [(+)-Ent-A-anti-(20)]; (−)-Ent-B-anti-3-[3-[(dimethylamino)methyl]-4-hydroxy-1-(3-phenylpropyl)piperidin-4-yl]benzamide [(−)-Ent-B-anti-(20)]; 3-{1-[3-(2-Chloro-4-fluorophenyl)propyl]-3-[(dimethylamino)methyl]-4-hydroxypiperidin-4-yl}benzamide (23); 3-((3S,4R)-1-(3-(2-Chloro-4-fluorophenyl)propyl)-3-((dimethylamino)methyl)-4-hydroxypiperidin-4-yl)benzamide (23a); 3-((3R,4S)-1-(3-(2-Chloro-4-fluorophenyl)propyl)-3-((dimethylamino) methyl)-4-hydroxypiperidin-4-yl)benzamide (23b); (+)-Ent-A-anti-3-[1-[3-(2-chloro-4-fluorophenyl)propyl]-3-[(dimethylamino)methyl]-4-hydroxypiperidin-4-yl]benzamide [(+)-Ent-A-anti-(23)]; (−)-Ent-B-anti-3-[1-[3-(2-chloro-4-fluorophenyl)propyl)-3-((dimethylamino)methyl)-4-hydroxypiperidin-4-yl)benzamide [(−)-Ent-B-anti-(23)]; 3-{3-[(Dimethylamino)methyl]-1-[3-(5-fluoropyridin-3-yl) propyl]-4-hydroxypiperidin-4-yl}benzamide; 3-[(3S,4R)-3-Dimethylaminomethyl-1-(5-fluoro-pyridin-3-ylmethyl)-4-hydroxy-piperidin-4-yl]-benzamide (26a); 3-[(3R,4S)-3-Dimethylaminomethyl-1-(5-fluoro-pyridin-3-ylmethyl)-4-hydroxy-piperidin-4-yl]-benzamide (26b); (+)-Ent-A-anti-3-[3-[(dimethylamino)methyl]-1-[3-(5-fluoropyridin-3-yl)propyl]-4-hydroxypiperidin-4-yl]benzamide; (−)-Ent-B-anti-3-[3-[(dimethylamino)methyl]-1-[3-(5-fluoropyridin-3-yl)propyl]-4-hydroxypiperidin-4-yl]benzamide; 3-[1-(cyclopropylmethyl)-3-[(dimethylamino)methyl]-4-hydroxypiperidin-4-yl]benzamide (35); (+)-Ent-A-syn-3-[1-(cyclopropylmethyl)-3-[(dimethylamino)methyl]-4-hydroxypiperidin-4-yl]benzamide [(+)-Ent-A-syn-(35)]; (−)-Ent-B-syn-3-[1-(cyclopropylmethyl)-3-[(dimethylamino)methyl]-4-hydroxypiperidin-4-yl]benzamide [(−)-Ent-B-syn-(35)]; (+)-Ent-A-anti-3-[1-(cyclopropylmethyl)-3-[(dimethylamino)methyl]-4-hydroxypiperidin-4-yl] benzamide [(+)-Ent-A-anti-(35)]; (−)-Ent-B-anti-3-[1-(cyclopropylmethyl)-3-[(dimethylamino)methyl]-4-hydroxypiperidin-4-yl]benzamide [(−)-Ent-B-anti-(35)]; 3-(3-((dimethylamino)methyl)-4-hydroxypiperidin-4-yl) benzamide (21); Rac-syn-3-(3-((dimethylamino)methyl)-4-hydroxypiperidin-4-yl)benzamide (rac-syn-21); Rac-anti-3-(3-((dimethylamino)methyl)-4-hydroxypiperidin-4-yl) benzamide (rac-anti-21); (+)-Ent-A-syn-3-(3-((dimethylamino) methyl)-4-hydroxypiperidin-4-yl) benzamide ((+)-Ent-A-syn-21); (−)-Ent-B-syn-3-(3-((dimethylamino)methyl)-4-hydroxypiperidin-4-yl) benzamide ((−)-Ent-B-syn-21); (+)-Ent-A-anti-3-(3-((dimethylamino)methyl)-4-hydroxypiperidin-4-yl) benzamide ((+)-Ent-A-anti-21); (−)-Ent-B-anti-3-(3-((dimethylamino)methyl)-4-hydroxypiperidin-4-yl) benzamide ((−)-Ent-B-anti-21); or a salt, solvate, enantiomer, diastereoisomer and/or tautomer thereof, and any mixtures thereof.

In certain embodiments, the at least one compound is a MOR agonist. In certain embodiments, the at least one compound decreases cyclic adenosine monophosphate (cAMP) levels in the subject. In certain embodiments, the at least one compound does not significantly induce recruitment, binding to, or association with a β-arrestin. In certain embodiments, the at least one compound does not significantly cause at least one side effect selected from the group consisting of tachyphylaxis, respiratory depression, constipation, nausea, emesis, withdrawal, dependence, and addiction. In certain embodiments, the pain comprises chronic pain, neuropathic pain, nociceptive pain, hyperalgesia, and/ or allodynia. In certain embodiments, the subject is a mammal. In certain embodiments, the mammal is human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
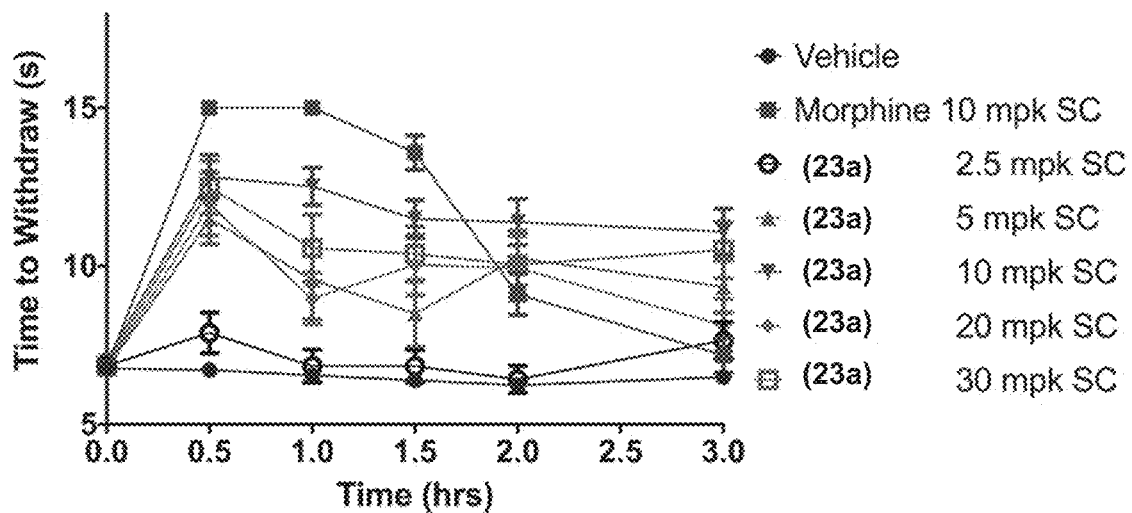
FIG. 1 is a graph illustrating results from a nociceptive analgesia test (rat tail flick, 76° C., N=8) for morphine and illustrative compound (23a). Error bars shown=standard error of the mean.

The invention relates in one aspect to compounds, and compositions comprising such compounds, that can be used to treat and/or prevent pain in a subject in need thereof. In certain embodiments, the subject is a mammal. In other embodiments, the mammal is a dog or cat. In yet other embodiments, the mammal is human, In certain embodiments, the compounds of the invention bind to the mu opioid receptor (MOR). In other embodiments, the compounds of the invention activate and/or act as agonists of the mu opioid receptor. In yet other embodiments, upon binding to the MOR, the compounds of the invention induce certain secondary messenger signaling manifested as intracellular responses, such as but not limited to G-protein signaling and β-arrestin signaling. In yet other embodiments, upon binding to the MOR, the compounds of the invention decrease cyclic adenosine monophosphate (cAMP) levels.

In certain embodiments, upon binding to the MOR, the compounds of the invention activate or behave as agonists of the MOR, induce intracellular responses such as but not limited to G-protein signaling and produce a decrease in cAMP.

In certain embodiments, the compounds of the invention do not significantly induce secondary messenger signaling, such as, but not limited to, recruitment of, binding to, and/or association with β-arrestins. More specifically, compounds of this invention have half-maximal effective concentration ($EC_{50}$) values for β-arrestin that are higher than approximately 1 micromolar ($EC_{50}>1$ µM) and/or exhibit β-arrestin activity of less than, or equal to 20% of the maximal response produced by the synthetic opioid peptide known as DAMGO (H-Tyr-D-Ala-Gly-NMe-Phe-Gly-OH; SEQ ID NO:1) as defined by the assays described herein. In certain embodiments, the compounds of the invention induce intracellular responses such as G-protein recruitment and binding, such as for the proteins known as Gi, decrease cAMP levels, and do not significantly induce recruitment, binding to, and/or association with β-arrestins.

In certain embodiments, the compounds of the invention induce intracellular responses, such as G-protein recruitment, and binding, such as for the proteins known as Gi, produce a decrease in cAMP, and do not significantly induce recruitment, binding to, and/or association with β-arrestins. In yet other embodiments, the compounds of the invention are G-protein biased (i.e., signaling pathway-selective) agonists.

In certain embodiments, the compounds of the invention provide relief from, and/or alleviate, pain in a subject. In other embodiments, the compounds of the invention bind to the MOR in a biased (i.e., signaling pathway-selective) manner, decreasing cAMP levels with minimal or no recruitment, association and/or interaction with β-arrestins.

In certain embodiments, the compounds of the invention diminish pain without producing respiratory depression, such as that caused by morphine and other well-known and widely used opioids and narcotics.

In certain embodiments, the compounds of the invention diminish pain without producing constipation, such as that caused by morphine and other well-known and widely used opioids and narcotics.

In certain embodiments, the compounds of the invention diminish pain without producing nausea, such as that caused by morphine and other well-known and widely used opioids and narcotics.

In certain embodiments, the compounds of the invention diminish pain without producing significant (or any at all) tolerance, such as that caused by morphine and other well-known and widely used opioids and narcotics.

In certain embodiments, the compounds of the invention diminish pain without producing significant (or any at all) tachyphylaxis, such as that caused by morphine and other well-known and widely used opioids and narcotics.

In certain embodiments, the compounds of the invention diminish pain without producing emesis, such as that caused by morphine and other well-known and widely used opioids and narcotics.

In certain embodiments, the compounds of the invention diminish pain without producing adverse effects associated with withdrawal, such as that caused by morphine and other well-known and widely used opioids and narcotics.

In certain embodiments, the compounds of the invention diminish pain without producing dependence, such as that caused by morphine and other well-known and widely used opioids and narcotics.

In certain embodiments, the compounds of the invention diminish pain without producing one or more of the following phenomena: nausea, emesis, constipation, respiratory depression, somnolence, tolerance, tachyphylaxis, dependence and/or addiction.

The invention further provides methods of administering a compound of the invention to provide pain relief. In certain embodiments, the pain comprises chronic pain. In other embodiments, the pain comprises neuropathic pain. In yet other embodiments, the pain comprises nociceptive pain. In yet other embodiments, the pain comprises hyperalgesia. In yet other embodiments, the pain comprises allodynia.

Prior to the present day understanding of the β-arrestin pathways, many GPCR ligands were developed pursuing optimization of binding to the 7-transmembrane (7-TM) receptor and not surprisingly, many widely used therapeutics are now known to be promiscuous, engaging both G-protein and β-arrestin pathways. For example, morphine, the classic, prototypic MOR agonist, produces analgesia through G-protein signaling. However, this effect is therapeutically "offset" by β-arrestin driven effects that produce receptor internalization and desensitization, which result in tolerance that necessitates increasing doses to maintain analgesic effect. In addition, β-arrestin driven signaling leads to the production of additional on-target adverse effects such as constipation and respiratory depression.

Mice lacking β-arrestin-2 exhibit enhanced and prolonged analgesia with very little tolerance, as well as attenuated respiratory depression and acute constipation, as compared to wild type. This finding suggests that agonists that selectively activate G-protein signaling, but are devoid of β-arrestin-mediated effects, can provide morphine-like analgesia without the classic adverse effect profile. The biased MOR agonist, oliceridine or N-[(3-methoxy thiophen-2-yl) methyl]-2-[(9R)-9-pyridin-2-yl-6-oxaspiro[4.5]decan-9-yl] ethanamine, which is selective for G-protein signaling ($EC_{50}$=8 nM, $E_{max}$=83% vs morphine) with only minor β-arrestin recruitment (14% $E_{max}$) in cell-based assays, exhibited decreased on-target adverse effects (such as nausea, and decrease in respiratory drive) in healthy volunteers and produced a higher level of analgesia in patients following bunionectomy. This work demonstrates the power of biased ligands for GPCR signaling, which maintain/enhance desired therapeutic benefits while removing adverse side effects.

In certain embodiments, the ability of a compound to activate G-protein or β-arrestin is not an on/off switch for a given pathway, but rather a continuous function. To capture this, each compound is measured for activity in cell assays that are linked to β-arrestin recruitment and G-protein signaling. By comparing the activity between these two measures (accounting for both $EC_{50}$ and maximal response reached, $E_{max}$) a relative activity (RA) value is determined.

$$\Delta RA = LOG\left(\frac{EMAX_{\beta\text{-}Arr}}{EC50_{\beta\text{-}Arr}}\right) - LOG\left(\frac{EMAX_{G\text{-}Protein}}{EC50_{G\text{-}Protein}}\right).$$

In the case of MOR it is desirable to have high activation of the G-protein pathway while reducing activation of β-arrestin. In the case of the formula above, this means a lower RA value.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science, and organic chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

In one aspect, the terms "co-administered" and "co-administration" as relating to a subject refer to administering to the subject a compound of the invention or salt thereof along with a compound that may also treat any disease or disorder contemplated herein and/or with a compound that is useful in treating other medical conditions but which in themselves may cause or facilitate any disease or disorder contemplated herein. In certain embodiments, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "$ED_{50}$" refers to the effective dose of a formulation that produces 50% of the maximal effect in subjects that are administered that formulation.

As used herein, an "effective amount," "therapeutically effective amount" or "pharmaceutically effective amount" of a compound is that amount of compound that is sufficient to provide a beneficial effect to the subject to which the compound is administered.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

The term "prevent," "preventing" or "prevention," as used herein, means avoiding or delaying the onset of symptoms associated with a disease or condition in a subject that has not developed such symptoms at the time the administering of an agent or compound commences. Disease, condition and disorder are used interchangeably herein.

By the term "specifically bind" or "specifically binds," as used herein, is meant that a first molecule preferentially binds to a second molecule (e.g., a particular receptor or enzyme), but does not necessarily bind only to that second molecule.

As used herein, a "subject" may be a human or non-human mammal or a bird. Non-human mammals include, for example, livestock and pets, such as ovine, bovine, porcine, canine, feline and murine mammals. In certain embodiments, the subject is human.

The term "treat," "treating" or "treatment," as used herein, means reducing the frequency or severity with which symptoms of a disease or condition are experienced by a subject by virtue of administering an agent or compound to the subject.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "alkylene" by itself or as part of another substituent means, unless otherwise stated, a straight or branched hydrocarbon group having the number of carbon atoms designated (i.e., $C_1$-$C_{10}$ means one to ten carbon atoms) and includes straight, branched chain, or cyclic substituent groups, wherein the group has two open valencies. Examples include methylene, 1,2-ethylene, 1,1-ethylene, 1,1-propylene, 1,2-propylene and 1,3-propylene.

As used herein, the term "cycloalkyl," by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, alkoxy, tetrahydro-2-H-pyranyl, —$NH_2$, —$N(CH_3)_2$, (1-methyl-imidazol-2-yl), pyridin-2-yl, pyridin-3-yl, pyridin-4-yl, —C(=O)OH, trifluoromethyl, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl. In certain embodiments, the substituted alkyl is not substituted with a hydroxy group.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl or —$CH_2$-phenyl (benzyl). Preferred is aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted. Preferred is substituted aryl ($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two. In yet other embodiments, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, with straight being preferred.

The following abbreviations are used herein: β-arrestin, beta-arrestin-2 (protein); C, carbon; cAMP, cyclic adenosine monophosphate; DCM (or $CH_2Cl_2$), methylene chloride (dichloromethane); DIPEA, N,N-diisopropylethylamine; $EC_{50}$, half-maximal (50%) effective concentration; $E_{MAX}$, maximal response; ESI, electrospray ionization; EtOAc, ethyl acetate; GPCRs, G-protein coupled receptors; HCl, hydrochloric acid; $K_2CO_3$, potassium carbonate; KOH, potassium hydroxide; MeCN (or $CH_3CN$), acetonitrile; MHz, megahertz; MOR, mu opioid receptor; MS, mass spectrometry; $NH_4Cl$, ammonium chloride; $NH_4OH$, ammonium hydroxide (solution); n-BuLi, n-butylllithium; nc, not calculated; nd, not done (not conducted); NMR, nuclear magnetic resonance; PE, petroleum ether; RA, relative activity; TEA, trimethylamine.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds and Compositions

The invention includes a compound of formula (I), or a composition containing a compound of formula (I), or a salt, solvate, racemate, enantiomer, racemic diastereoisomer, single diastereoisomer, and/or tautomer thereof:

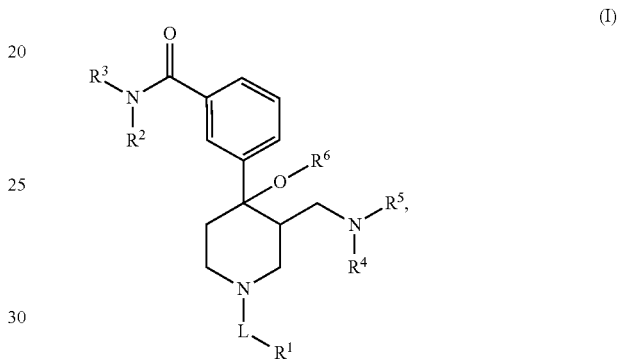

(I)

wherein:

L is selected from the group consisting of —($CZ^1Z^2$)—, —($CZ^1Z^2$—$CZ^1Z^2$)—, and —($CZ^1Z^2$—$CZ^1Z^2$—$CZ^1Z^2$)— (such as, but not limited to, —$CH_2$—, —$CH_2$—$CH_2$—, —$CHZ^2$—$CH_2$—, —$CH_2$—$CHZ^2$—, —$CHZ^2$—$CHZ^2$—, —$CZ^1Z^2$—$CH_2$—, —$CH_2$—$CZ^1Z^2$—, —$CZ^1Z^2$—$CHZ$—, —$CHZ^2$—$CZ^1Z^2$—, —$CZ^1Z^2$—$CZ^1Z^2$—, —$CH_2$—$CH_2$—$CH_2$, —$CHZ^2$—$CH_2$—$CH_2$, —$CH_2$—$CHZ^2$—$CH_2$, —$CH_2$—$CH_2$—$CHZ^2$, —$CZ^1Z^2$—$CH_2$—$CH_2$, —$CH_2$—$CZ^1Z^2$—$CH_2$, and/or —$CH_2$—$CH_2$—$CZ^1Z^2$);

$R^1$ is selected from the group consisting of

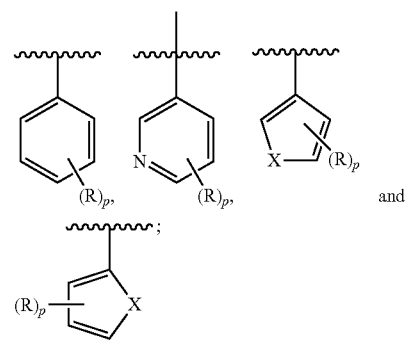

and $R^2$ is selected from the group consisting of hydrogen, $C_1$-$C_6$ alkyl, and substituted $C_1$-$C_6$ alkyl;

$R^3$ is selected from the group consisting of hydrogen, methyl and ethyl;

$R^4$ is selected from the group consisting of methyl and ethyl;

$R^5$ is selected from the group consisting of methyl and ethyl;

$R^6$ is selected from the group consisting of H and $C_1$-$C_6$ alkyl;

each occurrence of $Z^1$ and $Z^2$ is independently selected from the group consisting of hydrogen, fluoro and methyl;

X is selected from the group consisting of S, O, and N—$R^7$;

each occurrence of R is independently selected from the group consisting of hydrogen, fluoro, chloro, bromo, iodo, cyano, nitro, hydroxyl, $C_1$-$C_6$ alkoxy, $C_1$-$C_6$ alkyl, substituted $C_1$-$C_6$ alkyl, $C_2$-$C_6$ alkenyl, substituted $C_2$-$C_6$ alkenyl, alkynyl, substituted $C_2$-$C_6$ alkynyl, phenyl, substituted phenyl, —$COOR^7$ and carboxamide;

or -L-$R^1$ combine to form H, $C_1$-$C_6$ alkyl, or substituted $C_1$-$C_6$ alkyl (such as but not limited to cyclopropylmethyl);

each occurrence of p is independently selected from the group consisting of 0, 1, 2 and 3; and each occurrence of $R^7$ is independently selected from the group consisting of hydrogen and $C_1$-$C_6$ alkyl.

In certain embodiments, $R^2$ and $R^3$ are hydrogen.

In certain embodiments, $R^4$ and $R^5$ are methyl.

In certain embodiments, $R^6$ is selected from the group consisting of hydrogen and methyl. In other embodiments, $R^6$ is hydrogen. In yet other embodiments, $R^6$ is methyl.

In certain embodiments, L is selected from the group consisting of methylene (—$CH_2$—) and 1,2-ethylene (—$CH_2$—$CH_2$—). In other embodiments, L is methylene (—$CH_2$—). In yet other embodiments, L is 1,2-ethylene (—$CH_2$—$CH_2$—). In yet other embodiments, L is 1,3-propylene (—$CH_2$—$CH_2$—$CH_2$—).

In certain embodiments, $R^1$ is selected from the group consisting of phenyl, thienyl, furanyl, 3-pyridinyl, substituted phenyl, substituted thienyl, substituted furanyl, and substituted 3-pyridinyl.

In certain embodiments, $R^2$ and $R^3$ are hydrogen, $R^4$ and $R^5$ are methyl, $R^6$ is hydrogen or methyl, L is methylene (—$CH_2$—), ethylene (—$CH_2$—$CH_2$—), or 1,3-propylene (—$CH_2$—$CH_2$—$CH_2$—), $R^1$ is phenyl, thienyl, furanyl, 3-pyridinyl, substituted phenyl, substituted thienyl, substituted furanyl, or substituted 3-pyridinyl.

In certain embodiments, $R^2$ and $R^3$ are hydrogen, $R^4$ and $R^5$ are methyl, $R^6$ is hydrogen or methyl, L is ethylene (—$CH_2$—$CH_2$—), $R^1$ is phenyl, thienyl, furanyl, 3-pyridinyl, substituted phenyl, substituted thienyl, substituted furanyl, or substituted 3-pyridinyl.

In certain embodiments, $R^2$ and $R^3$ are hydrogen, $R^4$ and $R^5$ are methyl, $R^6$ is hydrogen, L is 1,2-ethylene (—$CH_2$—$CH_2$—), $R^1$ is phenyl, thienyl, furanyl, 3-pyridinyl, substituted phenyl, substituted thienyl, substituted furanyl, or substituted 3-pyridinyl.

In certain embodiments, $R^2$ and $R^3$ are hydrogen, $R^4$ and $R^5$ are methyl, $R^6$ is hydrogen or methyl, L is 1,3-propylene (—$CH_2$—$CH_2$—$CH_2$—), $R^1$ is phenyl, thienyl, furanyl, 3-pyridinyl, substituted phenyl, substituted thienyl, substituted furanyl, or substituted 3-pyridinyl.

In certain embodiments, $R^2$ and $R^3$ are hydrogen, $R^4$ and $R^5$ are methyl, $R^6$ is hydrogen, L is 1,3-propylene (—$CH_2$—$CH_2$—$CH_2$—), $R^1$ is phenyl, thienyl, furanyl, 3-pyridinyl, substituted phenyl, substituted thienyl, substituted furanyl, or substituted 3-pyridinyl.

In certain embodiments, each occurrence of substituted phenyl is independently substituted with at least one selected from the group consisting of $C_1$-$C_6$ alkyl, $C_1$-$C_6$ haloalkyl, $C_1$-$C_6$ haloalkoxy, fluoro, chloro, bromo, iodo, cyano, nitro, —N(R')(R'), —OR', —COOH, —COO($C_1$-$C_6$ alkyl), and carboxamide, wherein each occurrence of R' is independently H or $C_1$-$C_6$ alkyl.

In certain embodiments, each occurrence of substituted phenyl is independently selected from the group consisting of 2-chloro-4-fluoro-phenyl, 4-hydroxy-phenyl, and 4-methoxyphenyl.

In certain embodiments, each occurrence of substituted 3-pyridinyl is 5-halo-3-pyridinyl.

In certain embodiments, the thienyl substituent is 2-thienyl.

In certain embodiments, each occurrence of substituted alkyl, alkenyl and/or alkynyl is independently substituted with at least one substituent selected from the group consisting of $C_1$-$C_6$ alkyl, $C_1$-$C_6$ haloalkyl, $C_1$-$C_6$ haloalkoxy, halo, —OR', phenyl (thus yielding, in non-limiting examples, optionally substituted phenyl-($C_1$-$C_3$ alkyl), such as, but not limited to, benzyl or substituted benzyl) and —N(R')(R'), wherein each occurrence of R' is independently H or $C_1$-$C_6$ alkyl.

The compounds of the invention possess at least two stereocenters (the 3- and 4-positions of the piperidinyl ring), and each stereocenter can exist independently in either the (R) or (S) configuration. In certain embodiments, compounds of the invention exist as a mixture of four diastereoisomers. In certain embodiments, compounds of the invention exist as mixture of two diastereoisomers. In certain embodiments, the two diastereoisomers are the mirror image of each other. In certain embodiments, compounds of the invention exist as a racemic mixture of two diastereoisomers. In certain embodiments, compounds of the invention exist as a pure diastereoisomer.

In certain embodiments, the —O—$R^6$ group and the —$CH_2$—$NR^4R^5$ group are located on the same face of the piperidinyl ring (known herein as syn configuration). In certain embodiments, the —O—$R^6$ group and the —$CH_2$—$NR^4R^5$ group are located on opposite faces of the piperidinyl ring (known as and configuration). In the present disclosure, unless stated otherwise, the terms syn and anti relate to the relationship between the —O—$R^6$ group and the —$CH_2$—$NR^4R^5$ group in a compound of the invention.

All diastereoisomers, racemates, single diastereoisomers, and all possible mixtures thereof, of compounds of the invention are contemplated herein.

In certain embodiments, the compound is

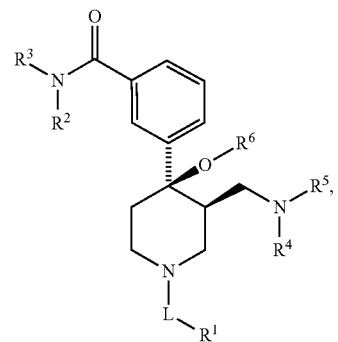

or a salt or solvate thereof. In certain embodiments, the compound is

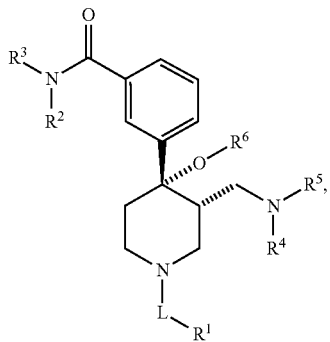

or a salt or solvate thereof. In certain embodiments, the compound is

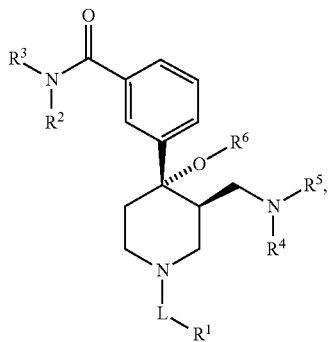

or a salt or solvate thereof. In certain embodiments, the compound is

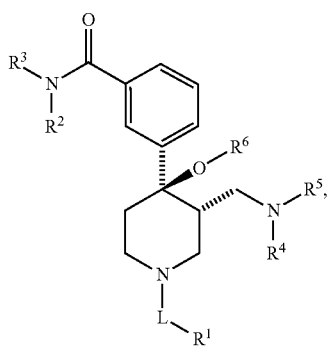

or a salt or solvate thereof.

Unless stated herein otherwise, each diastereomerically pure compound is recited as Ent. In the case where there are two diastereomerically pure compounds that are the mirror image of each other, then they are described as Ent-A and Ent-B, where the terms Ent-A and Ent-B do not mean to imply any absolute stereochemistry. Likewise, as indicated, certain structures illustrated herein are not meant to imply absolute stereochemistry, but rather just indicate the relative configuration of chiral centers in the compound structure.

In a non-limiting example, compounds of the invention that are Ent-A-syn-(I) and Ent-B-syn-(I) are described by the following pair of structures, such that Ent-A-syn-(I) corresponds to one of those structures, and Ent-B-syn-(I) corresponds to the other:

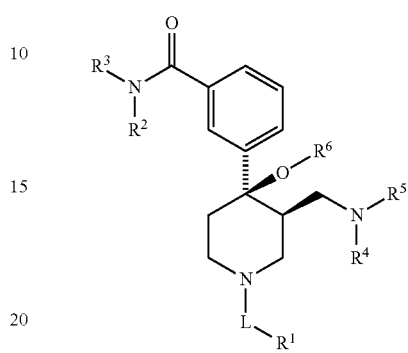

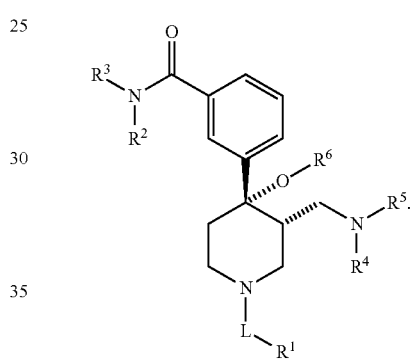

A mixture of 50:50 of Ent-A-syn-(I) and Ent-B-syn-(I) is indicated as rac-syn.

In a non-limiting example, compounds of the invention that are Ent-A-anti-(I) and Ent-B-anti-(I) are described by the following pair of structures, such that Ent-A-anti-(I) corresponds to one of those structures, and Ent-B-anti-(I) corresponds to the other:

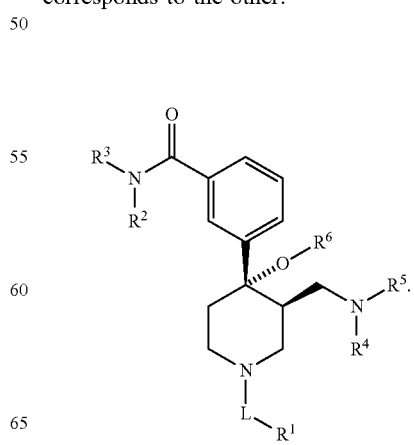

21
-continued

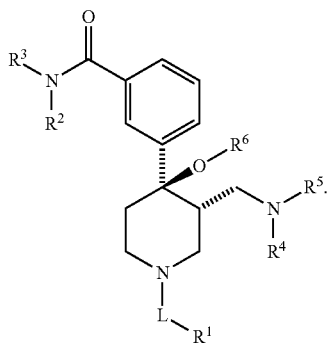

A mixture of 50:50 of Ent-A-ant-(I) and Ent-B-anti-(I) is indicated as rac-anti.

As used herein, the term "(+)" describes a dextrorotatory compound of the invention, and the term "(−)" describes a levorotatory compound of the invention.

In certain embodiments, the compound of the invention is at least one selected from the group consisting of:

3-(-(2-Chloro-4-fluoro-benzyl)-3-dimethylaminomethyl-4-hydroxy-piperidin-4-yl)-benzamide (6)

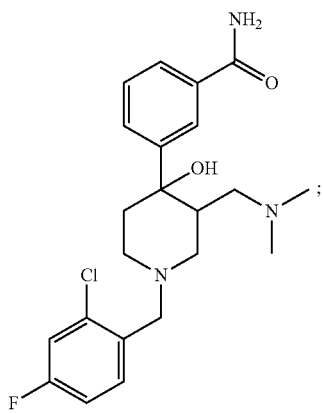 [SMILES: CN(C)CC1CN(Cc2ccc(F)cc2Cl)CCC1(O)c1cccc(C(N)=O)c1]

(+)-Ent-A-syn-3-(1-(2-chloro-4-fluorobenzyl)-3-((dimethylamino)methyl)-4-hydroxy piperidin-4-yl)benzamide [(+)-Ent-A-syn-(6)];

(−)-Ent-B-syn-3-(1-(2-chloro-4-fluorobenzyl)-3-((dimethylamino)methyl)-4-hydroxy piperidin-4-yl)benzamide [(−)-Ent-B-syn-(6)];

(+)-Ent-A-anti-3-[1-(2-chloro-4-fluorobenzyl)-3-[(dimethylamino)methyl]-4-hydroxypiperidin-4-yl]benzamide [(+)-Ent-A-anti-(6)];

(−)-Ent-B-anti-3-[1-(2-chloro-4-fluorobenzyl)-3-[(dimethylamino)methyl]-4-hydroxypiperidin-4-yl]benzamide [(−)-Ent-B-anti-(6)];

22

3-(3-Dimethylaminomethyl-4-hydroxy-1-thiophen-3-ylmethyl-piperidin-4-yl)-benzamide (11)

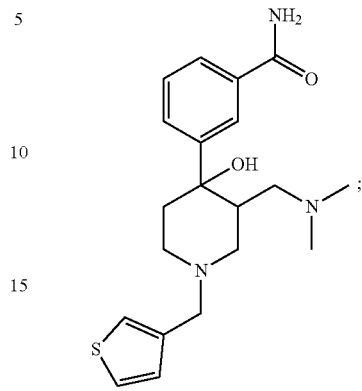

(+)-Ent-A-syn-3-[3-[(dimethylamino)methyl]-4-hydroxy-1-[(thiophen-3-yl)methyl]piperidin-4-yl] benzamide [(+)-Ent-A-syn-(11)];

(−)-Ent-B-syn-3-[3-[(dimethylamino)methyl]-4-hydroxy-1-[(thiophen-3-yl)methyl]piperidin-4-yl]benzamide [(−)-Ent-B-syn-(11)];

(+)-Ent-A-anti-3-[3-[(dimethylamino)methyl]-4-hydroxy-1-[(thiophen-3-yl)methyl]piperidin-4-yl] benzamide [(+)-Ent-A-anti-(11)];

(−)-Ent-B-anti-3-[3-[(dimethylamino)methyl]-4-hydroxy-1-[(thiophen-3-yl)methyl]piperidin-4-yl] benzamide [(−)-Ent-B-anti-(11)];

3-{3-[(dimethylamino)methyl]-1-[(5-fluoropyridin-3-yl)methyl]-4-hydroxypiperidin-4-yl}benzamide

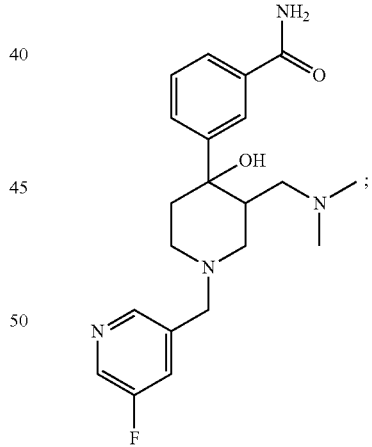

3-[(3S,4R)-3-Dimethylaminomethyl-1-(5-fluoro-pyridin-3-ylmethyl)-4-hydroxy-piperidin-4-yl]-benzamide (29a);

3-[(3R,4S)-3-Dimethylaminomethyl-1-(5-fluoro-pyridin-3-ylmethyl)-4-hydroxy-piperidin-4-yl]-benzamide (29b);

(+)-Ent-A-anti-3-[(dimethylamino)methyl]-1-[(5-fluoro-pyridin-3-yl)methyl]-4-hydroxypiperidin-4-yl]benzamide;

(−)-Ent-B-anti-3-[3-[(dimethylamino)methyl]-1-[(5-fluoro-pyridin-3-yl)methyl]-4-hydroxypiperidin-4-yl]benzamide;

3-(3-Dimethylaminomethyl-4-hydroxy-1-phenethyl-piperidin-4-yl)-benzamide (9)

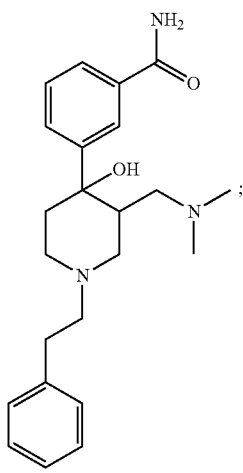 [SMILES: CN(C)CC1CN(CCc2ccccc2)CCC1(O)c1cccc(C(N)=O)c1]

(+)-Ent-A-syn-3-[3-[(dimethylamino)methyl]-4-hydroxy-1-(2-phenylethyl)piperidin-4-yl]benzamide (45a);
(−)-Ent-B-syn-3-[3-[(dimethylamino)methyl]-4-hydroxy-1-(2-phenylethyl)piperidin-4-yl]benzamide (45b);
(+)-Ent-A-anti-3-[3-[(dimethylamino)methyl]-4-hydroxy-1-(2-phenylethyl)piperidin-4-yl]benzamide [(+)-Ent-A-anti-(9)];
(−)-Ent-B-anti-3-[3-[(dimethylamino)methyl]-4-hydroxy-1-(2-phenylethyl)piperidin-4-yl]benzamide [(−)-Ent-B-anti-(9)];
3-(1-(2-Chloro-4-fluorophenethyl)-3-((dimethylamino)methyl)-4-hydroxypiperidin-4-yl) benzamide (13)

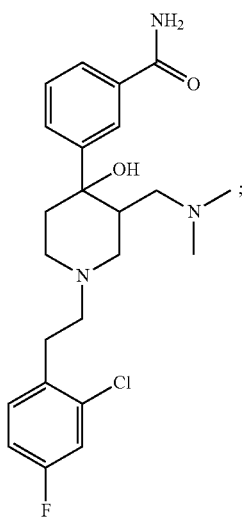 [SMILES: CN(C)CC1CN(CCc2ccc(F)cc2Cl)CCC1(O)c1cccc(C(N)=O)c1]

3-((3S,4R)-1-(2-Chloro-4-fluorophenethyl)-3-((dimethylamino)methyl)-4-hydroxypiperidin-4-yl)benzamide (32a);
3-((3R,4S)-1-(2-Chloro-4-fluorophenethyl)-3-((dimethylamino)methyl)-4-hydroxypiperidin-4-yl)benzamide (32b);
(+)-Ent-A-anti-3-[1-[2-(2-chloro-4-fluorophenyl)ethyl]-3-[(dimethylamino)methyl]-4-hydroxypiperidin-4-yl]benzamide [(+)-Ent-A-anti-(13)];
(−)-Ent-B-anti-3-[1-[2-(2-chloro-4-fluorophenyl)ethyl]-3-[(dimethylamino)methyl]-4-hydroxypiperidin-4-yl]benzamide [(−)-Ent-B-anti-(13)];
3-(3-((Dimethylamino)methyl)-4-hydroxy-1-(4-methoxyphenethyl)piperidin-4-yl)benzamide (17)

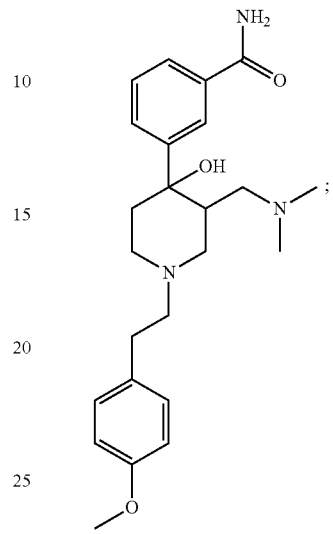

(+)-Ent-A-syn-3-(3-((dimethylamino)methyl)-4-hydroxy-1-(4-methoxyphenethyl)piperidin-4-yl)benzamide [(+)-Ent-A-syn-(17)];
(−)-Ent-B-syn-3-(3-((dimethylamino)methyl)-4-hydroxy-1-(4-methoxyphenethyl)piperidin-4-yl)benzamide [(−)-Ent-B-syn-(17)];
(+)-Ent-A-anti-3-(3-((dimethylamino)methyl)-4-hydroxy-1-(4-methoxyphenethyl)piperidin-4-yl)benzamide [(+)-Ent-A-anti-(17)];
(−)-Ent-B-anti-3-(3-((dimethylamino)methyl)-4-hydroxy-1-(4-methoxyphenethyl)piperidin-4-yl)benzamide [(−)-Ent-B-anti-(17)];
3-(3-((Dimethylamino)methyl)-4-hydroxy-1-(4-hydroxyphenethyl)piperidin-4-yl)benzamide (18)

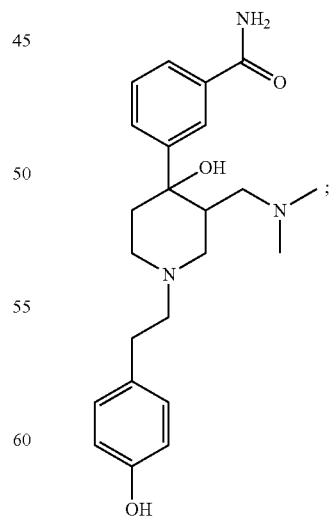

(+)-Ent-A-syn-3-[3-[(dimethylamino)methyl]-4-hydroxy-1-[2-(4-hydroxyphenyl)ethyl]piperidin-4-yl]benzamide (38a);

(−)-Ent-B-syn-3-[3-[(dimethylamino)methyl]-4-hydroxy-1-[2-(4-hydroxyphenyl)ethyl] piperidin-4-yl]benzamide (38b);

(+)-Ent-A-anti-3-[3-[(dimethylamino)methyl]-4-hydroxy-1-[2-(4-hydroxyphenyl)ethyl ]piperidin-4-yl]benzamide [(+)-Ent-A-anti-(18)];

(−)-Ent-B-anti-3-[3-(dimethylamino)methyl]-4-hydroxy-1-[2-(4-hydroxyphenyl)ethyl] piperidin-4-yl]benzamide [(−)-Ent-B-anti-(18)];

3-(3-((Dimethylamino)methyl)-4-hydroxy-1-(2-(thiophen-3-yl)ethyl)piperidin-4-yl)benzamide (15);

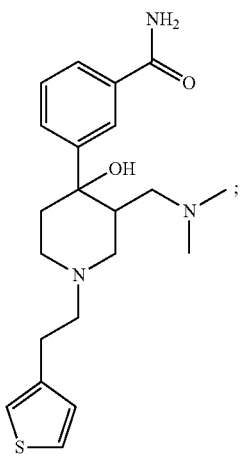 [SMILES: CN(C)CC1CN(CCc2ccsc2)CCC1(O)c1cccc(C(N)=O)c1]

3-(3S,4R)-3-((Dimethylamino)methyl)-4-hydroxy-1-(2-(thiophen-3-yl)ethyl)piperidin-4-yl)benzamide (41a);

3-((3R,4S)-3-((Dimethylamino)methyl)-4-hydroxy-1-(2-(thiophen-3-yl)ethyl)piperidin-4-yl)benzamide_(41b);

(+)-Ent-A-anti-3-[3-[(dimethylamino)methyl]-4-hydroxy-1-[2-(thiophen-3-yl)ethyl]piperidin-4-yl]benzamide [(+)-Ent-A-anti-(15)];

(−)-Ent-B-anti-3-[3-[(dimethylamino)methyl]-4-hydroxy-1-[2-(thiophen-3-yl)ethyl]piperidin-4-yl]benzamide [(−)-Ent-B-anti-(15)];

3-[3-Dimethylaminomethyl-4-hydroxy-1-(3-phenyl-propyl)-piperidin-4-yl]-benzamide (20)

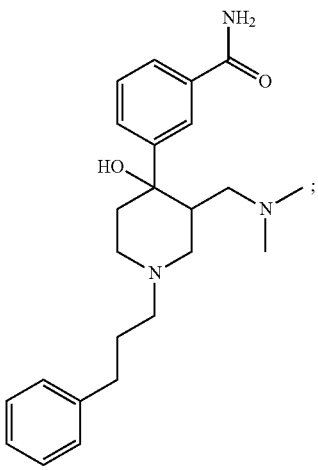 [SMILES: CN(C)CC1CN(CCCc2ccccc2)CCC1(O)c1cccc(C(N)=O)c1]

(+)-Ent-A-syn-3-[3-[(dimethylamino)methyl]-4-hydroxy-1-(3-phenylpropyl)piperidin-4-yl]benzamide (44a);

(−)-Ent-B-syn-3-[3-[(dimethylamino)methyl]-4-hydroxy-1-(3-phenylpropyl)piperidin-4-yl]benzamide (44b);

(+)-Ent-A-anti-3-[3-[(dimethylamino)methyl]-4-hydroxy-1-(3-phenylpropyl)piperidin-4-yl]benzamide [(+)-Ent-A-anti-(20)];

(−)-Ent-B-anti-3-[3-[(dimethylamino)methyl]-4-hydroxy-1-(3-phenylpropyl)piperidin-4-yl]benzamide [(−)-Ent-B-anti-(20)];

3-{1-[3-(2-Chloro-4-fluorophenyl)propyl]-3-[(dimethylamino)methyl]-4-hydroxypiperidin-4-yl}benzamide (23)

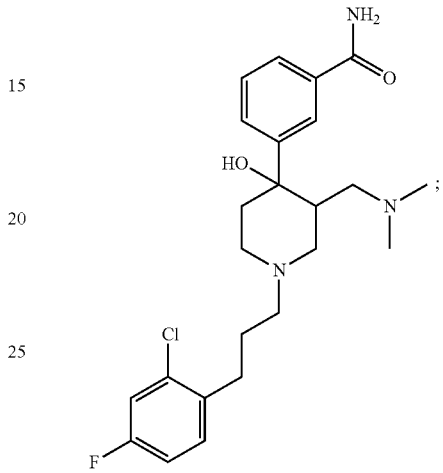

3-((3S,4R)-1-(3-(2-Chloro-4-fluorophenyl)propyl)-3-((dimethylamino)methyl)-4-hydroxypiperidin-4-yl)benzamide (23a);

3-((3R,4S)-1-(3-(2-Chloro-4-fluorophenyl)propyl)-3-((dimethylamino)methyl)-4-hydroxypiperidin-4-yl)benzamide (23b);

(+)-Ent-A-anti-3-[1-[3-(2-chloro-4-fluorophenyl)propyl]-3-[(dimethylamino)methyl]-4-hydroxypiperidin-4-yl]benzamide [(+)-Ent-A-anti-(23)];

(−)-Ent-B-anti-3-[1-(3-(2-chloro-4-fluorophenyl)propyl)-3-((dimethylamino)methyl)-4-hydroxypiperidin-4-yl]benzamide [(−)-Ent-B-anti-(23)];

3-{3-[(Dimethylamino)methyl]-1-[3-(5-fluoropyridin-3-yl)propyl]-4-hydroxypiperidin-4-yl}benzamide

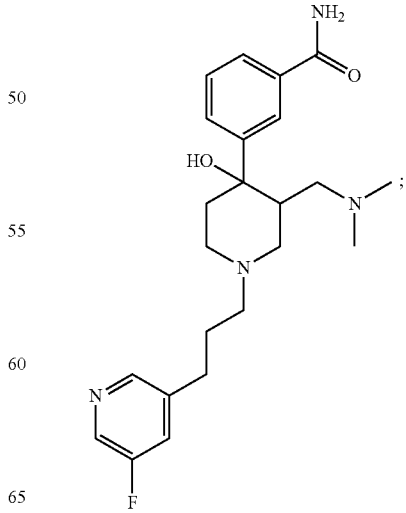

3-[(3S,4R)-3-Dimethylaminomethyl-1-(5-fluoro-pyridin-3-ylmethyl)-4-hydroxy-piperidin-4-yl]-benzamide (26a);
3-[(3R,4S)-3-Dimethylaminomethyl-1-(5-fluoro-pyridin-3-ylmethyl)-4-hydroxy-piperidin-4-yl]-benzamide (26b);
(+)-Ent-A-anti-3-[3-[(dimethylamino)methyl]-1-[3-(5-fluoropyridin-3-yl)propyl]-4-hydroxypiperidin-4-yl]benzamide;
(−)-Ent-B-anti-3-[3-[(dimethylamino)methyl]-1-[3-(5-fluoropyridin-3-yl)propyl]-4-hydroxypiperidin-4-yl]benzamide;
3-[1-(cyclopropylmethyl)-3-[(dimethylamino)methyl]-4-hydroxypiperidin-4-yl]benzamide

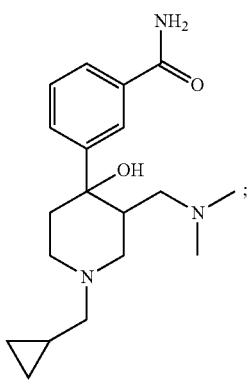

(35)

(+)-Ent-A-syn-3-[1-(cyclopropylmethyl)-3-[(dimethylamino)methyl]-4-hydroxypiperidin-4-yl]benzamide [(+)-Ent-A-syn-(35)];
(−)-Ent-B-syn-3-[1-(cyclopropylmethyl)-3-[(dimethylamino)methyl]-4-hydroxypiperidin-4-yl]benzamide [(−)-Ent-B-syn-(35)];
(+)-Ent-A-anti-3-[1-(cyclopropylmethyl)-3-[(dimethylamino)methyl]-4-hydroxypiperidin-4-yl]benzamide [(+)-Ent-A-anti-(35)];
(−)-Ent-B-anti-3-[1-(cyclopropylmethyl)-3-[(dimethylamino)methyl]-4-hydroxypiperidin-4-yl]benzamide [(−)-Ent-B-anti-(35)];
3-(3-((dimethylamino)methyl)-4-hydroxypiperidin-4-yl)benzamide

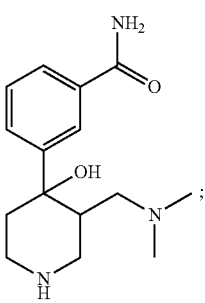

(21)

Rac-syn-3-(3-((dimethylamino)methyl)-4-hydroxypiperidin-4-yl)benzamide (rac-syn-21);
Rac-anti-3-(3-((dimethylamino)methyl)-4-hydroxypiperidin-4-yl)benzamide (rac-anti-21);
(+)-Ent-A-syn-3-(3-((dimethylamino)methyl)-4-hydroxypiperidin-4-yl)benzamide ((+)-Ent-A-syn-21);
(−)-Ent-B-syn-3-(3-((dimethylamino)methyl)-4-hydroxypiperidin-4-yl)benzamide ((−)-Ent-B-syn-21);
(+)-Ent-A-anti-3-(3-((dimethylamino)methyl)-4-hydroxypiperidin-4-yl)benzamide ((+)-Ent-A-anti-21);
(−)-Ent-B-anti-3-(3-((dimethylamino)methyl)-4-hydroxypiperidin-4-yl)benzamide ((−)-Ent-B-anti-21);
or a salt, solvate, enantiomer, diastereoisomer and/or tautomer thereof, and any mixtures thereof.

In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereoisomers. Resolution of compounds and isomers thereof is achieved by any means including, by way of non-limiting example, chemical processes, enzymatic processes, fractional crystallization, distillation, and chromatography. All possible stereochemical configurations of a given compound containing chiral center(s) are contemplated. All possible mixtures enriched with a particular enantiomer or diastereoisomer(s) are contemplated. All pure individual enantiomers or diastereoisomers are contemplated.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention may exist as tautomers. "Tautomerization" is a form of isomerization involving the migration of a proton accompanied by changes in bond order, often the interchange of a single bond with an adjacent double bond. Where tautomerization is possible, (e.g., in solution), a chemical equilibrium of tautomers can be reached. One well known example of tautomerization is between a ketone and its corresponding enol. Heterocycles may form tautomers such as the interconversion of pyrrolidinone and hydroxypyrrole. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention is susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

Compounds of the invention can in certain embodiments form acids or bases. In certain embodiments, the invention contemplates acid addition salts. In other embodiments, the invention contemplates base addition salts. In yet other embodiments, the invention contemplates pharmaceutically acceptable acid addition salts. In yet other embodiments, the invention contemplates pharmaceutically acceptable base addition salts. Pharmaceutically acceptable salts refer to salts of those bases or acids that are not toxic or otherwise biologically undesirable.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium, lithium and copper, iron and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

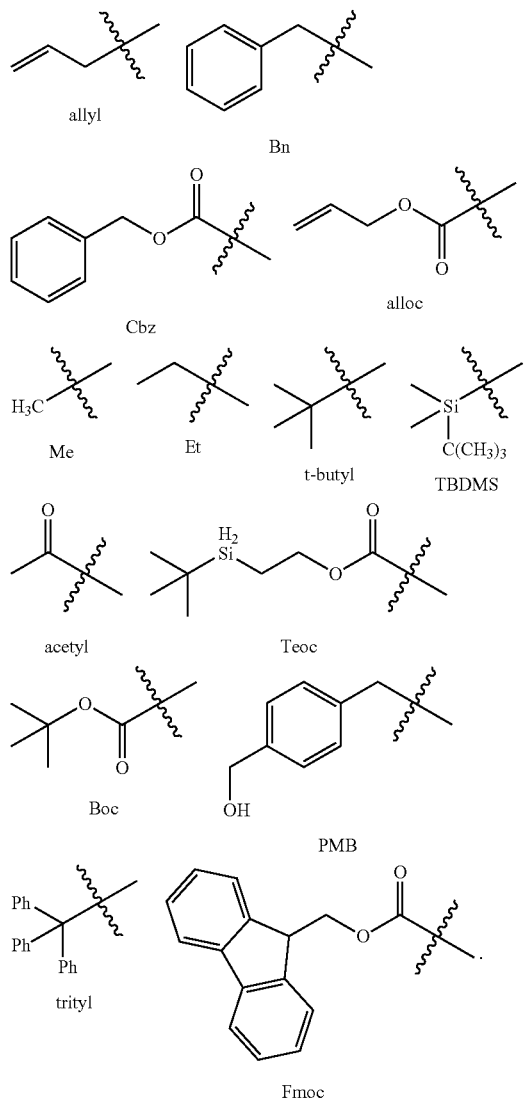

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

In certain embodiments, compounds of the invention can be prepared according to the following general schemes. It should be noted that the compound names and/or drawings provided in figures, schemes, and/or description provide relative or absolute stereochemistries of the various substituents of the compound in question, as appropriate. When used, absolute stereochemistry of a compound is indicated through the compound name and/or its structure as provided herein, unless stated otherwise. When so noted, the chemical structure of a compound can be provided to denote relative stereochemistry only and should not be interpreted as providing absolute stereochemistry of that chemical compound.

In certain embodiments, an N-protected piperidin-4-one (A) is reacted with a secondary amine and formaldehyde (under Mannich conditions), or reacted directly with a dialkylmethyleneimmonium salt such as but not limited to dimethylmethyleneimmonium chloride, to afford an N-protected 3-(dialkylamino)methyl-piperidin-4-one (B). Separately, an iodoarylnitrile, such as but not limited to 3-iodo-benzonitrile, is reacted with magnesium metal or with an alkyllithium species, such as but not limited to n-butyl-lithium, in an inert solvent such as but not limited to diethylether or tetrahydrofuran, under anhydrous conditions and an inert atmosphere, to produce the corresponding 3-cyanophenyl-magnesium bromide or 3-cyano-phenyl-lithium (C) respectively. At low temperatures, such as but not limited to $-78°$ C., N-protected 3-(dialkylamino)methyl-piperidin-4-one (B) is added to 3-cyano-phenyl-lithium (C) to obtain N-protected-4-(3-cyanophenyl)-3-((dimethyl-amino)methyl)-4-hydroxy-piperidine (D). Under appropriate conditions, a diastereoisomeric enrichment of syn-dial-kylamino-alcohol product (D-syn) versus anti-dialkylamino-alcohol product (D-anti) can be achieved. Removal of the N-protecting group, such as cleavage of tert-butyloxycarbonyl (N—BOC) or benzyl (N-Bn) via acid- or base-hydrolysis, or via hydrogenation, respectively, provides 4-(3-cyanophenyl)-3-((dimethylamino)methyl)-4-hydroxy-piperidine (E). N-Alkylation of the piperidine N—H can be accomplished by reaction with a benzyl- or phenethyl-halide, in the presence of a suitable amine base, to obtain the corresponding N-benzyl- or N-phenethyl-4-(3-cyanophenyl)-3-((dimethylamino)methyl)-4-hydroxy-piperidine (F). Alternatively, 4-(3-cyanophenyl)-3-((dimethylamino)methyl)-4-hydroxy-piperidine (E) can be N-alkylated via reductive alkylation by reaction with a benzaldehyde or an aryl-acetaldehyde in the presence of a reducing agent such as sodium cyano-borohydride. Base hydrolysis of N-benzyl- or N-phenethyl-4-(3-cyanophenyl)-3-((dimethylamino)methyl)-4-hydroxy-piperidine (F), such as via reaction with hydroxide, converts the nitrile functionality to carboxamide to produce 3-(1-benzyl or phenethyl)-3-((dimethylamino)methyl)-4-hydroxypiperidin-4-yl)-benzamide (G). Reaction with a strong acid such as but not limited to hydrochloric acid affords the corresponding acid addition salt, such as but not limited to 3-(1-benzyl or phenethyl)-3-((dimethylamino)methyl)-4-hydroxypiperidin-4-yl)-benzamide hydrochloride (Ga) (Scheme 1).

Scheme 1 (absolute stereochemistry not implied).

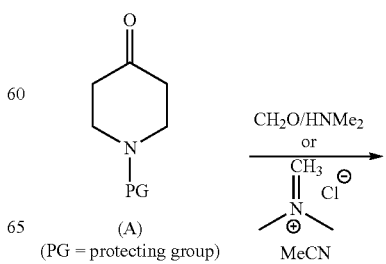

(A)
(PG = protecting group)

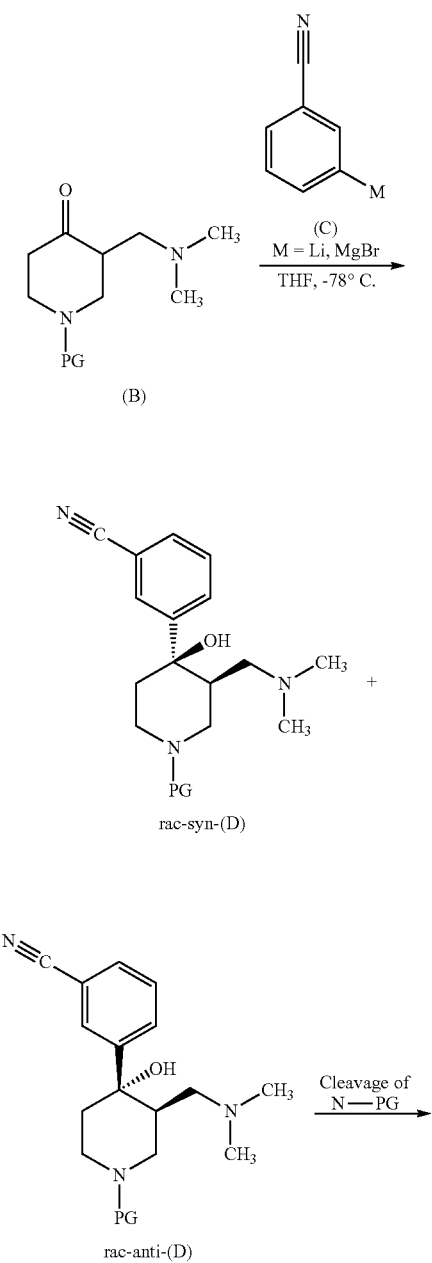

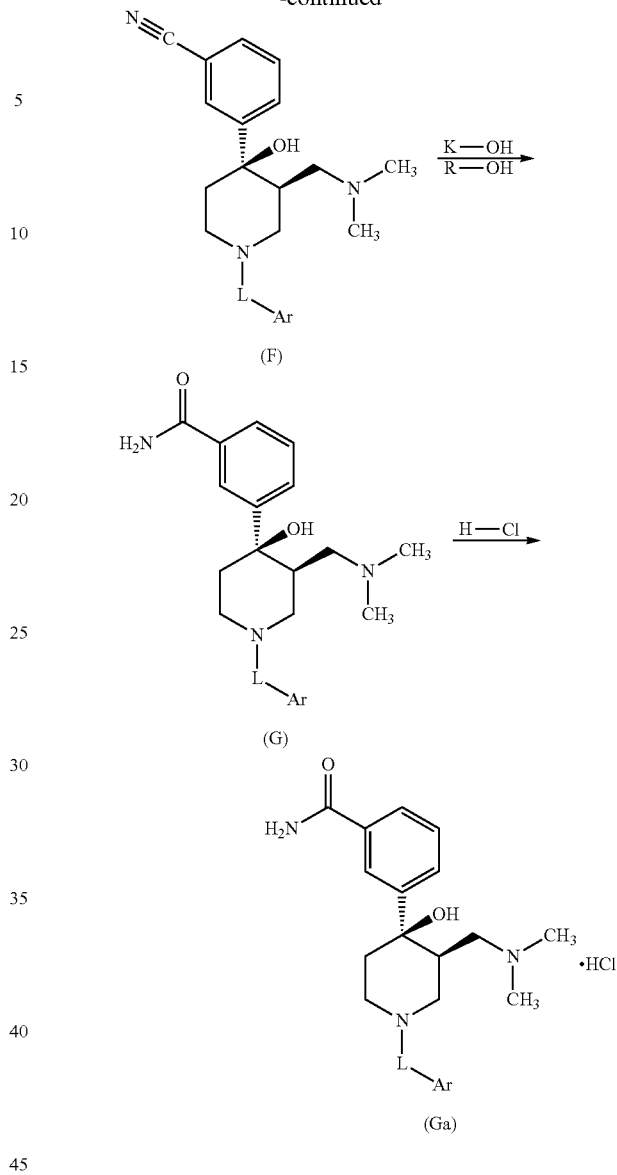

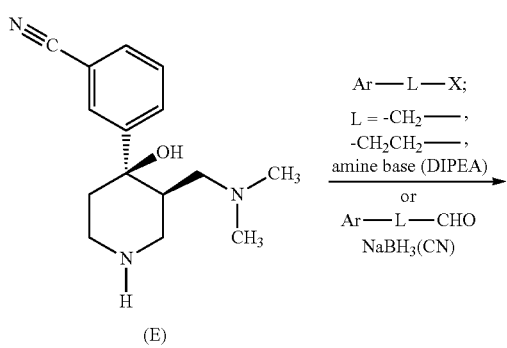

In certain embodiments, mixtures of racemic syn-amino-alcohol and anti-amino-alcohol diastereoisomeric products, such as rac-syn-(D) and rac-anti-(D) are formed and purified to obtain pure racemic diastereoisomer rac-syn-(D) using a separation method, such as but not limited to crystallization, chromatography or resolution of chiral acid-addition salts (Scheme 2).

In certain embodiments, mixtures of racemic syn-amino-alcohol and anti-amino-alcohol diastereoisomeric products, such as rac-syn-(D) and rac-anti-(D), are formed and purified to obtain pure racemic diastereoisomer rac-anti-(D) using a separation method, such as but not limited to crystallization, chromatography or resolution of chiral acid-addition salts (ent-A-anti-(D) and ent-B-anti-(D)).

In certain embodiments, racemic diastereoisomeric products such as rac-(G) are obtained and purified by a separation method, such as but not limited to crystallization, chromatography or resolution of chiral acid-addition salts to obtain pure single diastereoisomer ent-A-syn-(G) or ent-B-syn-(G) (Scheme 3).

Scheme 2 (absolute stereochemistry not implied).

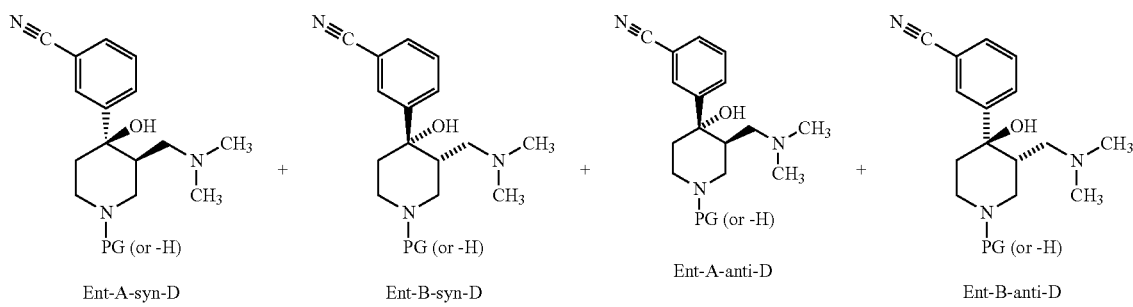

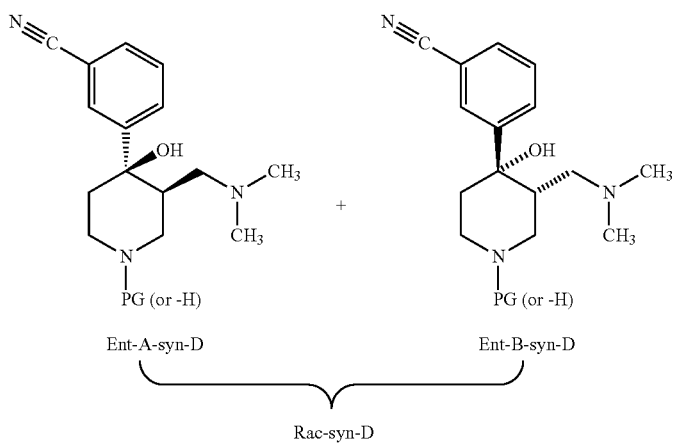

Scheme 3 (absolute stereochemistry not implied).

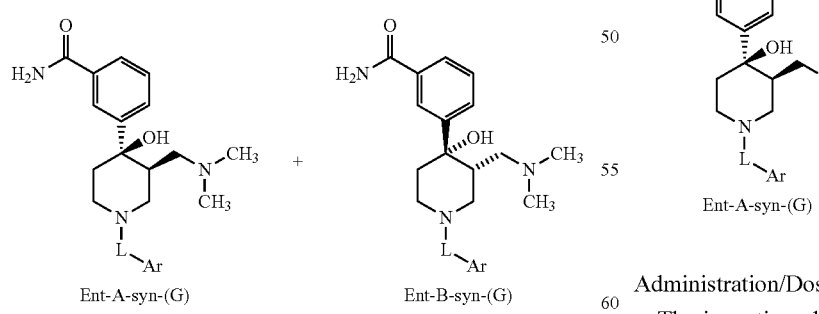

Administration/Dosage/Formulations

The invention also encompasses pharmaceutical compositions and methods of their use. These pharmaceutical compositions may comprise an active ingredient (which can be one or more compounds of the invention, or pharmaceutically acceptable salts thereof) optionally in combination with one or more pharmaceutically acceptable agents. The compositions set forth herein can be used alone or in combination with additional compounds to produce additive, complementary, or synergistic effects.

The regimen of administration may affect what constitutes an effective amount. The therapeutic formulations may be administered to the subject either prior to or after the onset of a disease or disorder contemplated herein. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated herein. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated herein. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect, and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated herein.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 350 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In certain embodiments, the dose of a compound of the invention is from about 1 mg and about 2,500 mg. In other embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in other embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated herein.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropyl methylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In certain embodiments, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated herein in the patient being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population)

and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, point out specific embodiments of the present invention, and are not to be construed as limiting in any way the remainder of the disclosure.

Materials and Methods
Analgesia (Tail Flick), Rat:

In rodents, the tail flick response to radiant heat is commonly used as a model to detect potentially useful analgesic agents. This assay is useful to discriminate between centrally acting morphine-like analgesics (active) and non-opioid or peripherally acting anti-inflammatory agents (inactive).

Procedurally, the time (seconds) required to elicit a tail flick response induced by focused radiant heat is measured as the pain threshold in groups of 8 Sprague-Dawley (SD) male rats weighing 110±20 g. Prolongation by 50 percent or more (≥50) of the time required to elicit a tail flick response 15 and 30 minutes following administration of test substance indicates possible analgesic activity. Also, one-way ANOVA followed by Dunnett's test is applied for comparison between vehicle control and treatment groups. See: D'Amour & Smith, 1941, J. Pharmacol. Exp. Ther. 72:74-79.

Motor (Spontaneous Activity), Rat:

Groups of 10 Sprague-Dawley rats weighing 200±20 g are employed. Test compounds (3, 10 and 100 mg/kg) are dissolved in vehicle (TBD) and administered intravenously. At a pre-treatment time to be selected, the animals are placed individually into locomotor activity chambers (Coulbourn Instruments, USA) in a quiet room at 25° C. For each 10-minute period over 60 min post dosing, individual motility counts (distance traveling, time spent traveling and vertical rearing) measured by interruption of infrared grids, are totaled. The mean±SEM for each treatment group is then calculated and Dunnett's test is applied for comparison between vehicle and treated groups. Differences are considered significant at $p<0.05$. See: Yamanuchi, et al., 1987, Arzneim.-Forsch./Drug Res. 37(II):157-164.

Gastrointestinal Motility, Rat:

Test substances (positive control being morphine) were administered subcutaneously to groups of 5 Wistar rats weighing 200±20 g, fasted with free access to water for 20-24 hours prior to testing. At 30 minutes post subcutaneous dosing, the animals were given a suspension of 5% charcoal in 10% gum arabic solution (2 ml/animal p.o.) and sacrificed 15 minutes later. The intestine was removed, and the length of the gut in cm (GL) as well as extent of charcoal movement from the pylorus to the beginning of the charcoal column in cm (CP) was measured.

Intestinal transit (IT) was calculated as IT=(CP/GL)×100%. A 30% or more (30) increase or decrease intestinal transit (IT), relative to the vehicle control group, was considered significant. The values in animals treated with test compounds compared with vehicle control group were also analyzed by using one-way ANOVA followed by Dunnett's test. Differences are considered statistically significant at $P<0.05$. See: Omosu, et al., 1988, Arzneim.-Forsch./Drug Res. 38(II):1309-1317.

Respiration (RR, TV, pH, $pCO_2$, $pO_2$), Rat:

Sprague Dawley (SD) derived male rats weighing 250±20 g are used. The animals are cannulated via common carotid artery (CCA) and fasted for 16 hours prior to use. Test substance is administered intraperitoneally to groups of 5 Sprague Dawley derived male rats weighing 250±20 g. Respiratory rate (RR), tidal volume (TV) and minute volume (MV) are measured every 30 seconds during baseline (−5 to 0 min) and after dosing (PO, 50 to 60 min; IV and IP, 20 to 30 min). At 65 minutes after test substance administration PO (IV and IP, 35 min), a 0.3 mL sample of blood is collected via carotid artery and immediately injected (less than 20 seconds) into a cassette of the blood gas analyzer (Osmetech, USA) to determine its pH, $pCO_2$ and $pO_2$. The mean±S.E.M. value of respiratory rate, tidal volume, minute volume, pH, $pCO_2$ and $pO_2$ post-treatment in each group is calculated and One-way ANOVA followed by Dunnett's test is applied for comparison between vehicle control and treated groups. Differences are considered significant at $p<0.05$.

Conditioned Placed Preference (Spontaneous Activity), Rat:

The conditioned place preference paradigm is a standard preclinical behavioral model used to study the rewarding and aversive effects of drugs. Although a number of different designs and apparatuses are used in this model, the basic characteristics of this task involve the association of a particular environment with drug treatment, followed by the association of a different environment with the absence of the drug (i.e., the drug's vehicle). A common variation of this design consists of a three-compartment chamber with the outer compartments being designed to have different characteristics (e.g., white vs. black walls, pine vs. corn bedding, horizontal grid vs. cross-grid flooring). The center compartment has no special characteristics and is not paired with a drug, and the gates between the compartments can be opened to allow an animal to pass freely between them. During training, an animal (typically a rat or mouse) is given an injection of a drug with potentially rewarding or aversive properties, and is then placed into one of the outer compartments for several minutes. On the following day, the rat is injected with the drug's vehicle and then placed in the opposite compartment. Generally, these daily sessions alternate between drug and vehicle for 2 or 3 days each. Afterward, a test session is conducted, which consists of placing the animal in the center compartment and then, after opening the gates to both of the outer compartments, recording the time the animal spends in each of the outer compartments during the session. A conditioned place preference (CPP) is found if the animals spend significantly more time in the drug-paired compartment versus the vehicle-paired compartment. On the other hand, if the animals spend significantly more time in the vehicle-paired compartment versus the drug-paired compartment, then this is considered a conditioned place aversion (CPA). Typically, drugs of abuse, such as cocaine, produce CPP, and drugs that elicit aversive effects, such as lithium chloride, produce CPA.

In certain embodiments, there are three days of adaptation where any preferences are assessed. Then, compartment assignments for drug or saline are based on any existing preferences. Drug assignments are always to the non-preferred side. Once training is initiated, drug and saline days are alternated with the animal confined for a period of time in the assigned compartment (60 minutes for (41a); 45 minutes for morphine). There are 8 days of training followed by the test day when both compartments are accessible and the computer counts how much time is spent in the respective compartment. See: Bardo et al., 1995, Neurosci. & Biobehav. Rev. 19(1):39-51

Example 1: G-Protein Assay

G-protein signaling was measured via second messenger cAMP modulation. Detection of cAMP modulation was accomplished in the PathHunter human OPRM1 (µ, MOR) Arrestin CHO-K1 cell line using the Dynamic2 cAMP Kit from Cisbio. The $E_{MAX}$ values of the chemiluminescent signal are all normalized to DAMGO, which is defined as 100%.

Example 2: β-Arrestin Assay

The DISCOVERX PATHHUNTER® β-Arrestin assay is used to measure β-arrestin-2 activity. The technology is based on Enzyme Fragment Complementation (EFC) with β-galactosidase (β-Gal) as the reporter. The enzyme is split into two inactive complementary portions (EA for Enzyme Acceptor, and ED for Enzyme Donor) expressed as fusion proteins in the cell. EA is fused to β-arrestin-2, and ED is fused to the C-terminus of the GPCR of interest. When a ligand binds and the GPCR is activated, β-arrestin-2 is recruited to the receptor resulting in an ED/EA complementation, restoring β-Gal activity, which is measured using chemiluminescence. For this assay, the PathHunter human OPRM1 (µ, MOR) Arrestin CHO-K1 cell line was used. The $E_{MAX}$ values of the chemiluminescent signal were all normalized to DAMGO, which is defined as 100%.

Scheme 4 (absolute stereochemistry not implied).

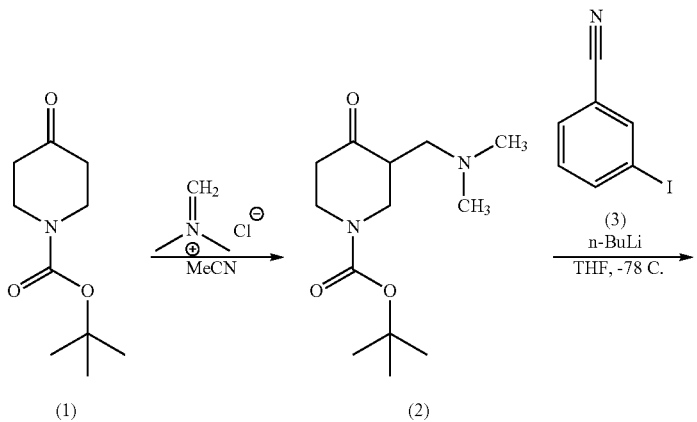

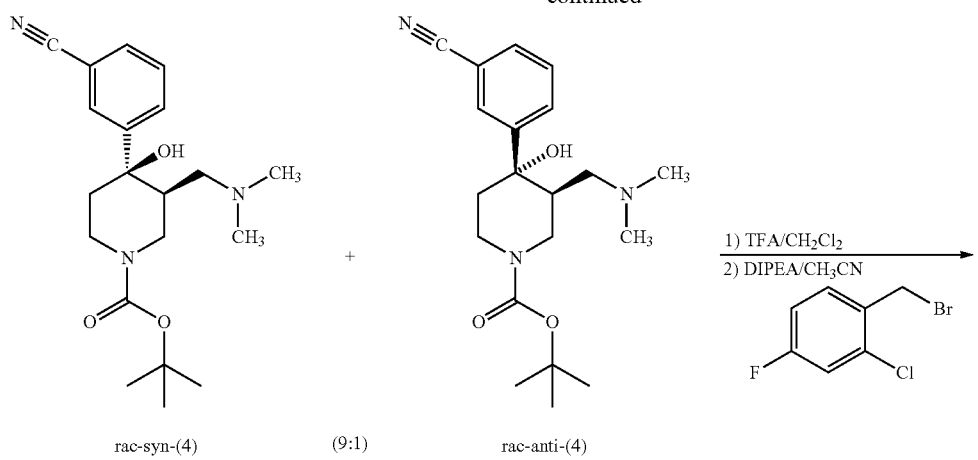
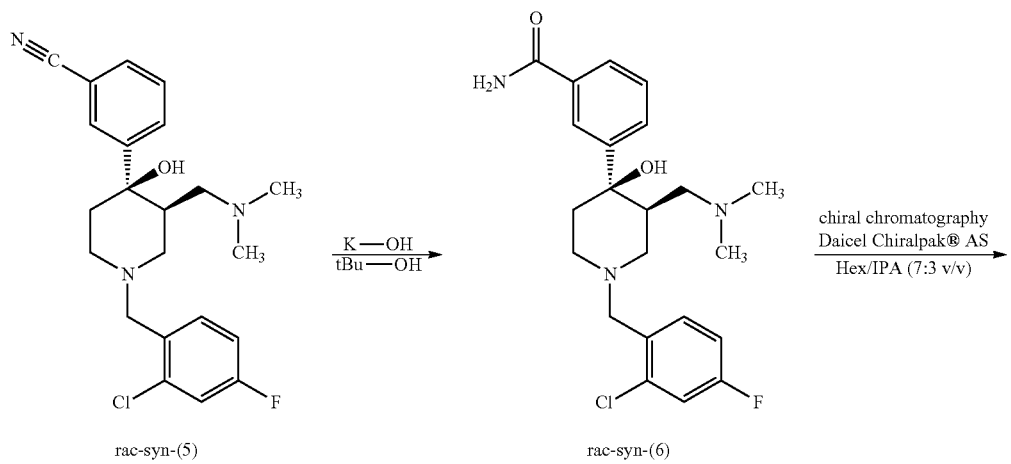
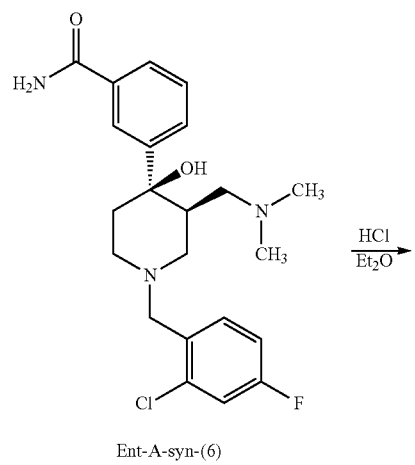

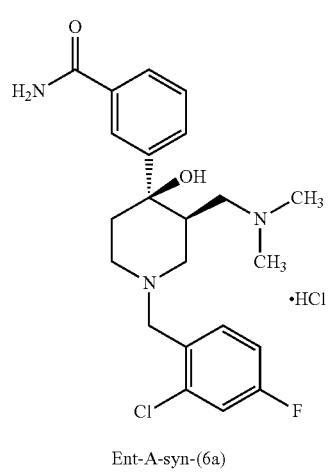
Ent-A-syn-(6a)

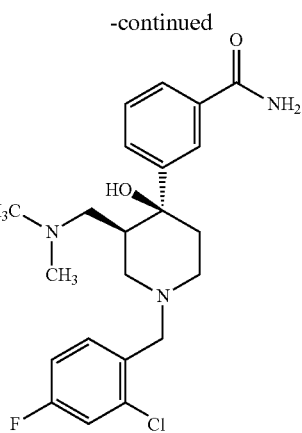
Ent-B-syn-(6)

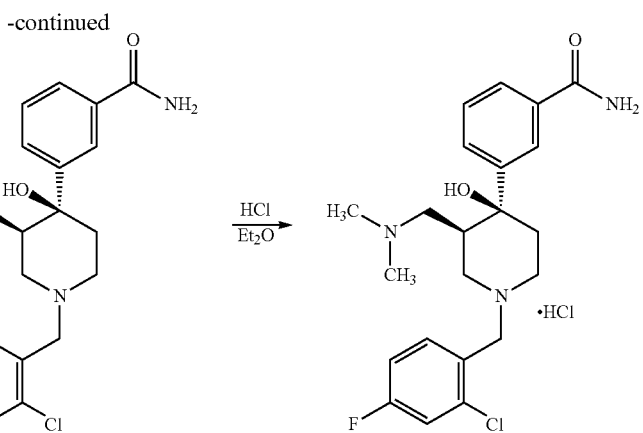
Ent-B-syn-(6a)

Example 3: 3-[1-(2-Chloro-4-fluoro-benzyl)-3-dimethylaminomethyl-4-hydroxy-piperidin-4-yl]-benzamide (6) (see Scheme 4)

(a) tert-Butyl 3-((dimethylamino)methyl)-4-oxopiperidine-1-carboxylate (2)

An oven-dried round bottom flask was charged with 1-tert-butyloxy-carbonyl-piperid-4-one (1) (1.50 g, 7.57 mmol), dimethyl-methyleneimmonium chloride (1.05 g, 11.3 mmol) and purged with argon. Acetonitrile (25 mL) was added, and the resulting suspension was stirred at room temperature for 24 h, during which time all solids dissolved. Aqueous ammonium hydroxide (NH$_4$OH 25% (w/v), 10 mL) and a brine solution (10 mL) were added. The resulting suspension was extracted with EtOAc (3×30 mL); the organic extracts were combined and dried over solid anhydrous Na$_2$SO$_4$. After filtration, the volatiles were removed via rotary evaporation to yield crude tert-butyl 3-((dimethylamino)methyl)-4-oxopiperidine-1-carboxylate (2) as slightly yellow cloudy oil, which was used in the next step without purification. ESI-MS (m/z): 257 [M+H]$^+$.

(b) tert-Butyl-4-(3-cyanophenyl)-3-((dimethylamino)methyl)-4-hydroxypiperidine-1-carboxylate (4)

An oven-dried round bottom flask was charged with 3-iodobenzonitrile (3) (2.08 g, 9.07 mmol) and purged with argon. Anhydrous THE (27 mL) was added and the resulting solution was cooled to −78° C. After cooling, a solution of n-BuLi (2.3 M, 4.40 mL, 9.67 mmol) was added dropwise, upon which mixture turned deep orange and viscous. A solution of tert-butyl 3-((dimethylamino)methyl)-4-oxopiperidine-1-carboxylate (2) (1.55 g, 6.05 mmol) in THE (3 mL) was added dropwise (color of the reaction mixture changed from orange to brown). The resulting mixture was stirred at −78° C. for 10 min and poured into a stirred mixture of a saturated NH$_4$Cl (50 mL) and NH$_4$OH (25%, 5 mL) solution. The resulting suspension was extracted with EtOAc (3×30 mL), and the combined organic extracts were dried over solid anhydrous Na$_2$SO$_4$. After filtration, the volatiles were removed via rotary evaporation, and the residue was purified by reverse phase flash chromatography using gradient elution from H$_2$O/MeCN (70:30) to H$_2$O/MeCN (40:60) to yield tert-butyl-4-(3-cyanophenyl)-3-((dimethylamino)methyl)-4-hydroxypiperidine-1-carboxylate (4) (1.49 g (80% purity), 55% yield in 2 steps from 1) as a mixture of diastereoisomers (9:1). 400 MHz $^1$H-NMR (CDCl$_3$, ppm): δ 7.86 (s, 1H), 7.71 (d, J=7.9 Hz, 1H), 7.55 (ddd, J=7.6, 7.6 1.3 Hz, 1H), 7.46 (dd, J=7.8, 7.8 Hz, 1H), 4.10-3.84 (m, 2H), 3.56-3.41 (m, 1H), 3.33-3.20 (m, 1H), 2.34 (dd, J=14.4, 4.1 Hz, 1H), 2.25 (d, J=14.2 Hz, 1H), 2.10 (s, 6H), 2.04-1.96 (m, 1H), 1.77-1.66 (m, 1H), 1.62-1.54 (m, 1H), 1.50 (s, 9H). ESI-MS (m/z): 360 [M+H]$^+$.

(c) 3-(1-(2-Chloro-4-fluorobenzyl)-3-((dimethylamino)methyl)-4-hydroxypiperidin-4-yl)benzonitrile (5)

Trifluoroacetic acid (1.12 ml, 14.6 mmol) was added to the solution of tert-butyl-4-(3-cyanophenyl)-3-((dimethylamino)methyl)-4-hydroxypiperidine-1-carboxylate (4) (440 mg (80% purity), 0.97 mmol) in CH$_2$Cl$_2$ (10 mL) and the resulting mixture was stirred at ambient temperature for 1 h. The volatiles were removed and the residue was dissolved in MeCN (10 mL). To this solution, DIPEA (0.67 mL, 3.88 mmol) was added followed by 2-chloro-4-fluorobenzyl bromide (239 mg, 1.07 mmol), and the resulting mixture was stirred at ambient temperature for 16 h. A brine solution (10 mL) and a NH$_4$OH solution (25%, 2 mL) were added and the resulting suspension was extracted with EtOAc (3×15 mL). The combined organic extracts were dried over anhydrous solid Na$_2$SO$_4$. After filtration, the volatiles were removed via rotary evaporation, and the residue was purified by reverse phase flash chromatography using gradient elution from H$_2$O/MeCN (60:40) to H$_2$O/MeCN (40:60) to yield 3-(1-(2-chloro-4-fluorobenzyl)-3-((dimethylamino)methyl)-4-hydroxypiperidin-4-yl)benzonitrile (5) (253 mg, 65% yield) as yellowish oil. 400 MHz $^1$H NMR (CDCl$_3$, ppm): δ 7.90 (s, 1H), 7.78 (d, J=7.9 Hz, 1H), 7.55-7.43 (m, 3H), 7.13 (dd, J=8.5, 2.6 Hz, 1H), 6.99 (ddd, J=8.3, 8.3, 2.6 Hz, 1H), 3.73 (s, 2H), 2.91 (t, J=11.2 Hz, 1H), 2.81-2.72 (m, 2H), 2.72-2.64 (m, 1H), 2.33 (dd, J=14.0, 4.5 Hz, 1H), 2.24-2.18 (m, 1H), 2.15 (dd, J=14.4, 1.6 Hz, 1H), 2.08 (s, 6H), 1.99-1.88 (m, 1H), 1.63 (dt, J=13.8, 2.6 Hz, 1H). ESI-MS (m/z): 402 [M+H]$^+$.

(d) 3-(1-(2-Chloro-4-fluorobenzyl)-3-((dimethylamino)methyl)-4-hydroxypiperidin-4-yl)benzamide (6)

An oven-dried round bottom flask was charged with 3-(1-(2-chloro-4-fluorobenzyl)-3-((dimethylamino)methyl)-4-hydroxypiperidin-4-yl)benzonitrile (5) (100 mg, 0.25 mmol) and ground KOH (41 mg, 0.75 mmol), and purged with argon. tBuOH (2 mL) was added and the reaction mixture was heated for 3 h at 80° C. After cooling, a brine solution (1 mL) was added and the resulting suspension was extracted with EtOAc (3×2 mL). The combined organic extracts were dried over solid anhydrous $Na_2SO_4$. After filtration, the volatiles were removed via rotary evaporation, and the residue was purified by reverse phase flash chromatography using eluent gradient from $H_2O$/MeCN (80:20) to $H_2O$/MeCN (40:60) to yield 3-(1-(2-chloro-4-fluorobenzyl)-3-((dimethylamino)methyl)-4-hydroxypiperidin-4-yl)-benzamide (6) (81 mg, 80% yield) as a white foam. 300 MHz $^1$H NMR (CDCl$_3$, ppm): δ 8.03 (s, 1H), 7.79-7.67 (m, 2H), 7.52 (dd, J=8.5, 6.4 Hz, 1H), 7.44 (dd, J=7.7, 7.7 Hz, 1H), 7.12 (dd, J=8.6, 2.6 Hz, 1H), 6.99 (ddd, J=8.3, 8.3, 2.6 Hz, 1H), 6.21 (brs, 1H), 5.74 (brs, 1H), 3.74-3.60 (AB quartet, 2H), 2.89 (dd, J=11.2, 11.2 Hz, 1H), 2.79-2.56 (m, 3H), 2.35 (dd, J=13.9, 4.5 Hz, 1H), 2.30-2.18 (m, 1H), 2.07 (s, 6H), 2.05-1.92 (m, 2H), 1.69-1.60 (m, 1H), (mixture of diastereoisomers). ESI-MS (m/z): 420 [M+H]$^+$.

(e) 3-(1-(2-Chloro-4-fluorobenzyl)-3-((dimethylamino)methyl)-4-hydroxypiperidin-4-yl)benzamide Hydrochloride (6a)

A solution of 2M HCl in diethyl ether (70 μL, 0.14 mmol) was added to a solution of 3-(1-(2-chloro-4-fluorobenzyl)-3-((dimethylamino)methyl)-4-hydroxypiperidin-4-yl) benzamide (6) (60 mg, 0.14 mmol) in diethyl ether/MeOH (10 mL/0.5 mL). The mixture was stirred at ambient temperature for 30 min, during which time a precipitate formed. The solids were filtered, washed with diethyl ether (5 mL) and dried over $P_2O_5$ in vacuo at 65° C. for 24 h to yield 3-(1-(2-chloro-4-fluorobenzyl)-3-((dimethylamino)methyl)-4-hydroxypiperidin-4-yl)benzamide hydrochloride (6a) (41 mg, 63% yield). 300 MHz $^1$H NMR (CD$_3$OD, ppm): δ 8.08 (s, 1H), 7.98 (dd, J=8.7, 5.9 Hz, 1H), 7.85 (d, J=7.7 Hz, 1H), 7.76 (d, J=7.7 Hz, 1H), 7.61-7.53 (m, 1H), 7.47 (dd, J=7.7, 2.6 Hz, 1H), 7.30 (ddd, J=8.3, 8.3, 2.6 Hz, 1H), 4.66 (s, 2H), 3.97-3.87 (m, 1H), 3.67-3.52 (m, 3H), 3.18-3.02 (m, 2H), 2.85-2.67 (m, 5H), 2.49 (s, 3H), 2.02-1.92 (m, 1H). ESI-MS (m/z): 420 [M+H]$^+$.

Example 4

Ent-A-syn-(3-(1-(2-chloro-4-fluorobenzyl)-3-((dimethylamino)methyl)-4-hydroxy piperidin-4-yl)benzamide (Ent-A-syn-(6)); and Ent-B-syn 3-(1-(2-chloro-4-fluorobenzyl)-3-((dimethylamino)methyl)-4-hydroxy piperidin-4-yl)benzamide (Ent-B-syn-(6))

Separation into Individual Stereoisomers:
The mixture of 3-(1-(2-chloro-4-fluorobenzyl)-3-((dimethylamino)methyl)-4-hydroxypiperidin-4-yl)-benzamide (6) diastereoisomers obtained above were separated on chiral stationary phase chromatography using (Daicel CHIRALPAK® AS 250 mm×10 mm) column and Hex/IPA (7:3) as mobile phase on Shimadzu LC-20AP: Rt stereoisomer A=11.3 min, Rt stereoisomer B=16.2 min at 3 mL/min flow rate.

Example 5: 3-(3-Dimethylaminomethyl-4-hydroxy-1-phenethyl-piperidin-4-yl)-benzamide (9), and Corresponding Hydrochloride Salt (9a)

(a) 3-(3-((Dimethylamino)methyl)-4-hydroxy-1-phenethylpiperidin-4-yl)benzonitrile (8)

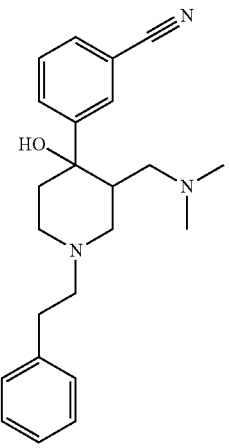 [SMILES: CN(C)CC1CN(CCc2ccccc2)CCC1(O)c1cccc(C#N)c1]

Trifluoroacetic acid (0.64 ml, 8.34 mmol) was added to a solution of tert-butyl-4-(3-cyanophenyl)-3-((dimethylamino)methyl)-4-hydroxypiperidine-1-carboxylate (4) (250 mg (80% purity), 0.56 mmol) in $CH_2Cl_2$ (5 mL), and the resulting mixture was stirred at ambient temperature for 1 h. The volatiles were removed and residue was dissolved in a $CH_2Cl_2$/TEA (5 mL/0.2 mL) solution. Acetic acid (64 μL, 1.11 mmol), 2-phenylacetaldehyde (0.19 mL, 1.67 mmol) and NaBH(OAc)$_3$ (590 mg, 2.78 mmol) were added, and the resulting suspension was stirred at ambient temperature for 16 h. After this time, a brine solution (5 mL) and a NH$_4$OH solution (25%, 1 mL) were added and the suspension was extracted with EtOAc (3×10 mL). The combined organic extracts were dried over solid anhydrous $Na_2SO_4$. After filtration, the volatiles were removed via rotary evaporation, and the residue was purified by reverse phase flash chromatography using gradient elution from $H_2O$/MeCN (90:10) to $H_2O$/MeCN (50:50) to yield 3-(3-((dimethylamino)methyl)-4-hydroxy-1-phenethylpiperidin-4-yl)benzonitrile (8) (166 mg, 82% yield) as yellowish oil. 300 MHz $^1$H-NMR (CDCl$_3$, ppm): δ 7.93 (s, 1H), 7.77 (d, J=7.8 Hz, 1H), 7.54 (d, J=7.6 Hz, 1H), 7.45 (dd, J=7.7, 7.7 Hz, 1H), 7.35-7.27 (m, 2H), 7.25-7.17 (m, 3H), 2.92-2.67 (m, 8H), 2.58 (ddd, J=11.8, 11.8, 2.8 Hz, 1H), 2.35 (dd, J=14.4, 4.8 Hz, 1H), 2.23-2.15 (m, 1H), 2.08 (s, 6H), 1.98-1.87 (m, 1H), 1.67-1.62 (m, 1H). ESI-MS (m/z): 364 [M+H]$^+$.

(b) 3-(3-((Dimethylamino)methyl)-4-hydroxy-1-phenethylpiperidin-4-yl)benzamide (9)

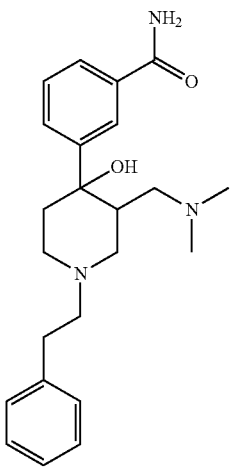 [SMILES: CN(C)CC1CN(CCc2ccccc2)CCC1(O)c1cccc(C(N)=O)c1]

An oven-dried round bottom flask was charged with 3-(3-((dimethylamino)methyl)-4-hydroxy-1-phenethylpiperidin-4-yl)benzonitrile (8) (100 mg, 0.28 mmol), ground KOH (45 mg, 0.81 mmol) and purged with argon. tBuOH (2 mL) was added and the suspension was heated at 80° C. for 3 h. After cooling, brine (1 mL) was added, and the resulting suspension was extracted with EtOAc (3×2 mL). The combined organic extracts were dried over solid anhydrous $Na_2SO_4$. After filtration, the volatiles were removed to yield 3-(3-((dimethylamino)methyl)-4-hydroxy-1-phenethylpiperidin-4-yl)benzamide (9) (92 mg, 88% yield) as white foam. 300 MHz $^1$H NMR (CDCl$_3$, ppm): δ 8.04 (s, 1H), 7.77-7.69 (m, J=7.1 Hz, 2H), 7.48-7.41 (m, 1H), 7.35-7.27 (m, 2H), 7.26-7.17 (m, 3H), 6.23 (s, 1H), 5.68 (s, 1H), 2.95-2.69 (m, 8H), 2.61 (ddd, J=12.0, 12.0, 2.9 Hz, 1H), 2.38 (dd, J=13.9, 4.7 Hz, 1H), 2.32-2.23 (m, 1H), 2.13 (dd, J=14.0, 1.5 Hz, 1H), 2.08 (s, 6H), 1.72-1.65 (m, 1H). ESI-MS (m/z): 382 [M+H]$^+$.

(c) 3-(3-Dimethylaminomethyl-4-hydroxy-1-phenethyl-piperidin-4-yl)-benzamide Hydrochloride (9a)

3-(3-((Dimethylamino)methyl)-4-hydroxy-1-phenethylpiperidin-4-yl)benzamide (9) (80 mg, 0.21 mmol) was treated with 2M HCl (in diethyl ether) in diethyl ether/MeOH (10 mL/0.5 mL) using procedure described for compound (6a) to produce 3-(3-dimethylamino methyl-4-hydroxy-1-phenethyl-piperidin-4-yl)-benzamide hydrochloride (9a) (61 mg, 70% yield). 300 MHz $^1$H NMR (CD$_3$OD, ppm): δ 8.05 (s, 1H), 7.83 (d, J=7.8 Hz, 1H), 7.74 (d, J=7.9 Hz, 1H), 7.54 (dd, J=7.8, 7.8 Hz, 1H), 7.39-7.22 (m, 5H), 3.60-3.50 (m, 1H), 3.45-3.36 (m, 1H), 3.27-2.98 (m, 6H), 2.84-2.70 (m, 1H), 2.67-2.54 (m, 1H), 2.54-2.22 (m, 8H), 1.90 (ddd, J=14.9, 2.6, 2.6 Hz, 1H). ESI-MS (m/z): 382 [M+H]$^+$.

Example 6: 3-(3-Dimethylaminomethyl-4-hydroxy-1-thiophen-3-ylmethyl-piperidin-4-yl)-benzamide (11), and Corresponding Hydrochloride Salt (11a)

(a) 3-(3-((Dimethylamino)methyl)-4-hydroxy-1-(thiophen-3-ylmethyl)piperidin-4-yl)benzonitrile (10)

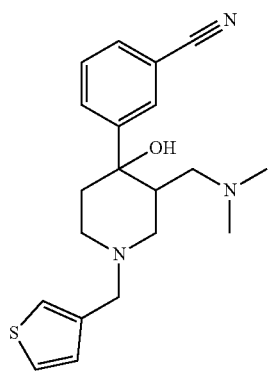 [SMILES: CN(C)CC1CN(Cc2ccsc2)CCC1(O)c1cccc(C#N)c1]

tert-Butyl-4-(3-cyanophenyl)-3-((dimethylamino)methyl)-4-hydroxypiperidine-1-carboxylate (4) (250 mg (80% purity), 0.56 mmol) was treated with trifluoroacetic acid, then reacted with thiophene-3-carboxaldehyde using procedure described for compound (8) to afford 3-(3-((dimethylamino)methyl)-4-hydroxy-1-(thiophen-3-ylmethyl) piperidin-4-yl)benzonitrile (10) (160 mg, 81% yield). 300 MHz $^1$H NMR (CDCl$_3$, ppm): δ 7.90 (s, 1H), 7.76 (d, J=7.8 Hz, 1H), 7.56-7.50 (m, 1H), 7.48-7.41 (m, 1H), 7.29 (dd, J=4.9, 3.0 Hz, 1H), 7.17-7.13 (m, 1H), 7.10 (dd, J=4.9, 1.0 Hz, 1H), 3.63 (s, 2H), 2.81-2.67 (m, 3H), 2.52 (ddd, J=11.8, 11.8, 2.9 Hz, 1H), 2.31 (dd, J=14.1, 4.5 Hz, 1H), 2.21-2.13 (m, 1H), 2.07 (s, 6H), 1.95-1.84 (m, 1H), 1.61 (ddd, J=13.7, 2.6, 2.6 Hz, 1H). ESI-MS (m/z): 356 [M+H]$^+$.

(b) 3-(3-((Dimethylamino)methyl)-4-hydroxy-1-(thiophen-3-ylmethyl)piperidin-4-yl)benzamide (11)

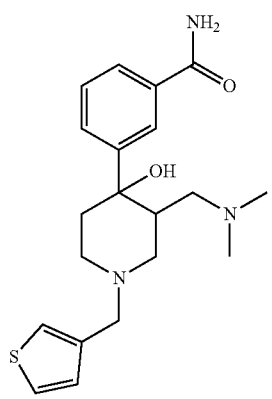 [SMILES: CN(C)CC1CN(Cc2ccsc2)CCC1(O)c1cccc(C(N)=O)c1]

3-(3-((Dimethylamino)methyl)-4-hydroxy-1-(thiophen-3-ylmethyl)piperidin-4-yl)benzonitrile (10) (150 mg, 0.42 mmol) was treated with KOH (70 mg, 1.27 mmol) using procedure described for compound (9) to afford 3-(3-((dimethylamino)methyl)-4-hydroxy-1-(thiophen-3-ylmethyl) piperidin-4-yl)benzamide (11) (142 mg, 90% yield). 300

MHz ¹H NMR (CDCl₃, ppm): δ 8.02 (s, 1H), 7.72 (dd, J=7.7, 1.6 Hz, 2H), 7.44 (dd, J=7.7, 7.7 Hz, 1H), 7.30 (dd, J=4.9, 3.0 Hz, 1H), 7.17 (d, J=2.1 Hz, 1H), 7.11 (d, J=4.9 Hz, 1H), 6.25 (s, 1H), 5.73 (s, 1H), 3.65 (s, 2H), 2.81-2.70 (m, 3H), 2.54 (ddd, J=11.9, 11.9, 2.8 Hz, 1H), 2.35 (dd, J=13.9, 4.6 Hz, 1H), 2.30-2.19 (m, 1H), 2.14-2.07 (m, 1H), 2.06 (s, 6H), 1.97 (dd, J=12.5, 4.6 Hz, 2H), 1.69-1.59 (m, 2H). ESI-MS (m/z): 374 [M+H]⁺.

(c) 3-(3-((Dimethylamino)methyl)-4-hydroxy-1-(thiophen-3-ylmethyl)piperidin-4-yl)benzamide Hydrochloride (11a)

3-(3-((Dimethylamino)methyl)-4-hydroxy-1-(thiophen-3-ylmethyl)piperidin-4-yl) benzamide (11) (120 mg, 0.35 mmol) was treated with 2M HCl (in diethyl ether) in diethyl ether/MeOH (10 mL/0.5 mL) using procedure described for compound (6a) to produce 3-(3-((dimethylamino)methyl)-4-hydroxy-1-(thiophen-3-ylmethyl)piperidin-4-yl)benzamide hydrochloride (11a) (55 mg, 38% yield). 300 MHz ¹H NMR (CD₃OD, ppm): δ 8.08 (s, 1H), 7.90-7.81 (m, 2H), 7.77 (d, J=7.9 Hz, 1H), 7.65-7.54 (m, 2H), 7.44 (d, J=4.9 Hz, 1H), 4.60-4.42 (AB quartet, 2H), 3.87-3.75 (m, 1H), 3.48-3.37 (m, 3H), 3.18-2.97 (m, 2H), 2.84-2.70 (m, 2H), 2.64 (s, 6H), 2.02-1.92 (m, 1H). ESI-MS (m/z): 374 [M+H]⁺.

Example 7: 3-(1-(2-Chloro-4-fluorophenethyl)-3-((dimethylamino)methyl)-4-hydroxy piperidin-4-yl) benzamide (13), and Corresponding Hydrochloride Salt (13a)

(a) 3-(1-(2-Chloro-4-fluorophenethyl)-3-((dimethylamino)methyl)-4-hydroxypiperidin-4-yl)benzonitrile (12)

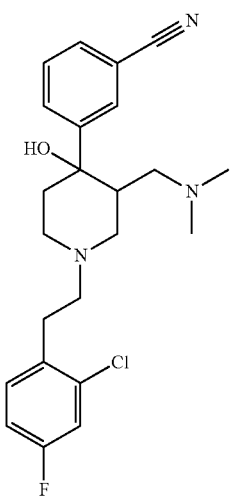 [SMILES: CN(C)CC1CN(CCc2ccc(F)cc2Cl)CCC1(O)c1cccc(C#N)c1]

tert-Butyl-4-(3-cyanophenyl)-3-((dimethylamino)methyl)-4-hydroxypiperidine-1-carboxylate (4) (180 mg, 0.50 mmol) was treated with trifluoroacetic acid, then reacted with 2-(2-chloro-4-fluorophenyl)acetaldehyde using procedure described for compound (8) to afford 3-(1-(2-chloro-4-fluorophenethyl)-3-((dimethylamino)methyl)-4-hydroxypiperidin-4-yl) benzonitrile (12) (125 mg, 60% yield). 300 MHz ¹H NMR (CDCl₃, ppm): δ 7.95-7.89 (m, 1H), 7.81-7.73 (m, 1H), 7.54 (dd, J=7.6, 1.4, 1.4 Hz, 1H), 7.45 (dd, J=7.6, 7.6 Hz, 1H), 7.23 (dd, J=8.6, 6.2 Hz, 1H), 7.11 (dd, J=8.6, 2.6 Hz, 1H), 6.93 (ddd, J=8.2, 8.2, 2.6 Hz, 1H), 3.01-2.91 (m, 3H), 2.91-2.75 (m, 3H), 2.73-2.51 (m, 3H), 2.35 (dd, J=14.5, 4.9 Hz, 1H), 2.23-2.13 (m, 2H), 2.09 (s, 6H), 1.98-1.83 (m, 1H), 1.66 (dt, J=13.8, 2.7 Hz, 1H). ESI-MS (m/z): 416, 418 [M+H]⁺.

(b) 3-(1-(2-Chloro-4-fluorophenethyl)-3-((dimethylamino)methyl)-4-hydroxypiperidin-4-yl)benzamide (13)

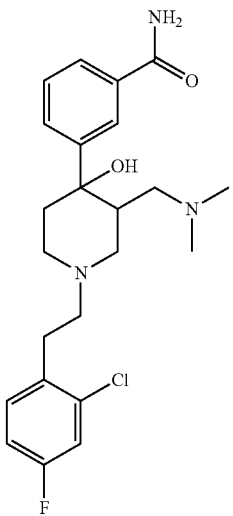 [SMILES: CN(C)CC1CN(CCc2ccc(F)cc2Cl)CCC1(O)c1cccc(C(N)=O)c1]

3-(1-(2-Chloro-4-fluorophenethyl)-3-((dimethylamino) methyl)-4-hydroxypiperidin-4-yl)benzonitrile (12) (120 mg, 0.29 mmol) was treated with KOH using procedure described for compound (9) to afford 3-(1-(2-chloro-4-fluorophenethyl)-3-((dimethylamino)methyl)-4-hydroxypiperidin-4-yl)benzamide (13) (110 mg, 88% yield). 300 MHz ¹H NMR (CDCl₃, ppm): δ 8.07-8.02 (m, 1H), 7.78-7.68 (m, 2H), 7.45 (dd, J=7.7, 7.7 Hz, 1H), 7.24 (dd, J=8.4, 6.2 Hz, 1H), 7.11 (dd, J=8.6, 2.6 Hz, 1H), 6.93 (ddd, J=8.3, 8.3, 2.6 Hz, 1H), 6.22 (br s, 1H), 5.80 (br s, 1H), 3.02-2.93 (m, 2H), 2.93-2.78 (m, 3H), 2.76-2.57 (m, 3H), 2.38 (dd, J=13.9, 4.6 Hz, 1H), 2.32-2.21 (m, 1H), 2.14 (dd, J=14.2, 2.0 Hz, 1H), 2.14-1.95 (m, 2H), 2.08 (s, 6H), 1.74-1.63 (m, 1H). ESI-MS (m/z): 434, 436 [M+H]⁺.

(c) 3-(1-(2-Chloro-4-fluorophenethyl)-3-((dimethylamino)methyl)-4-hydroxypiperidin-4-yl)benzamide Hydrochloride (13a)

3-(1-(2-Chloro-4-fluorophenethyl)-3-((dimethylamino) methyl)-4-hydroxypiperidin-4-yl)benzamide (13) (110 mg, 0.25 mmol) was treated with 2M HCl (in diethyl ether) in diethyl ether/MeOH (15 mL/0.5 mL) using procedure described for compound (6a) to produce 3-(1-(2-chloro-4-fluorophenethyl)-3-((dimethylamino)methyl)-4-hydroxypiperidin-4-yl) benzamide hydrochloride (13a) (98 mg, 82% yield). 300 MHz H-NMR (CD₃OD, ppm): δ 8.10-8.04 (m, 1H), 7.87-7.81 (m, 1H), 7.79-7.72 (m, 1H), 7.56 (dd, J=7.7, 7.7 Hz, 1H), 7.47 (dd, J=8.6, 6.0 Hz, 1H), 7.28 (dd, J=8.6, 2.6 Hz, 1H), 7.10 (ddd, J=8.4, 8.4, 2.6 Hz, 1H), 3.68-3.51 (m, 1H), 3.50-3.36 (m, 1H), 3.35-3.04 (m, 6H), 2.97 (dd, J=13.6, 9.2 Hz, 1H), 2.79-2.65 (m, 1H), 2.65-2.44 (m, 2H), 2.55 (s, 6H), 1.98-1.86 (m, 1H). ESI-MS (m/z): 434, 436 [M+H]⁺.

Example 8: 3-(3-((Dimethylamino)methyl)-4-hydroxy-1-(2-(thiophen-3-yl)ethyl) piperidin-4-yl)benzamide (15), and Corresponding Hydrochloride Salt (15a)

(a) 3-(3-((Dimethylamino)methyl)-4-hydroxy-1-(2-(thiophen-3-yl)ethyl)piperidin-4-yl)benzonitrile (14)

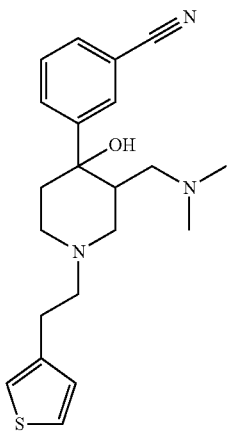 [SMILES: CN(C)CC1CN(CCc2ccsc2)CCC1(O)c1cccc(C#N)c1]

tert-Butyl-4-(3-cyanophenyl)-3-((dimethylamino)methyl)-4-hydroxypiperidine-1-carboxylate (4) (260 mg, 0.72 mmol) was treated with trifluoroacetic acid, then reacted with 2-(thiophen-3-yl)acetaldehyde using procedure described for compound (8) to produce 3-(3-((dimethylamino)methyl)-4-hydroxy-1-(2-(thiophen-3-yl)ethyl)piperidin-4-yl)benzonitrile (14) (55 mg, 21% yield). 300 MHz $^1$H NMR (CDCl$_3$, ppm): δ 7.96-7.91 (m, 1H), 7.81-7.73 (m, 1H), 7.54 (ddd, J=7.6, 1.4, 1.4 Hz, 1H), 7.45 (dd, J=7.6, 7.6 Hz, 1H), 7.28 (dd, J=4.9, 3.0 Hz, 1H), 7.07-7.02 (m, 1H), 7.00 (dd, J=4.9, 1.3 Hz, 1H), 3.10-2.49 (m, 8H), 2.36 (dd, J=14.2, 4.4 Hz, 1H), 2.21-2.03 (m, 3H), 2.09 (s, 6H), 1.73-1.62 (1H). ESI-MS (m/z): 370 [M+H]$^+$.

(b) 3-(3-((Dimethylamino)methyl)-4-hydroxy-1-(2-(thiophen-3-yl)ethyl)piperidin-4-yl)benzamide (15)

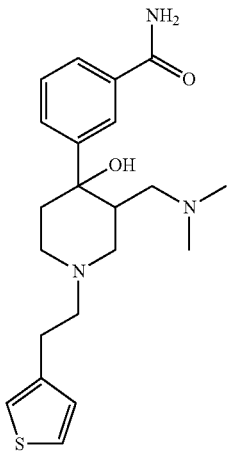 [SMILES: CN(C)CC1CN(CCc2ccsc2)CCC1(O)c1cccc(C(N)=O)c1]

3-(3-((Dimethylamino)methyl)-4-hydroxy-1-(2-(thiophen-3-yl)ethyl)piperidin-4-yl)benzonitrile (14) (50 mg, 0.14 mmol) was treated with KOH using procedure described for compound (9) to afford 3-(3-((dimethylamino)methyl)-4-hydroxy-1-(2-(thiophen-3-yl)ethyl) piperidin-4-yl)benzamide (15) (46 mg, 88% yield). 300 MHz $^1$H NMR (CDCl$_3$, ppm): δ 8.11-8.05 (m, 1H), 7.83-7.69 (m, 2H), 7.46 (dd, J=7.7, 7.7 Hz, 1H), 7.29 (dd, J=4.9, 3.0 Hz, 1H), 7.11-7.03 (m, 1H), 7.00 (dd, J=4.9, 1.3 Hz, 1H), 6.29 (s, 1H), 5.62 (s, 1H), 3.11-2.82 (m, 7H), 2.81-2.69 (m, 1H), 2.55-2.45 (m, 1H), 2.40 (dd, J=14.2, 4.6 Hz, 1H), 2.30-1.92 (m, 4H), 2.09 (s, 6H), 1.76-1.67 (m, 1H). ESI-MS (m/z): 388 [M+H]$^+$.

(c) 3-(3-((Dimethylamino)methyl)-4-hydroxy-1-(2-(thiophen-3-yl)ethyl)piperidin-4-yl) benzamide Hydrochloride (15a)

3-(3-((Dimethylamino)methyl)-4-hydroxy-1-(2-(thiophen-3-yl)ethyl)piperidin-4-yl)benzamide (15) (46 mg, 0.12 mmol) was treated with 2M HCl (in diethyl ether) in diethyl ether/MeOH (10 mL/0.5 mL) using procedure described for compound (9) to produce 3-(3-((dimethylamino)methyl)-4-hydroxy-1-(2-(thiophen-3-yl)ethyl)piperidin-4-yl)benzamide hydrochloride (15a) after washing with ether (47 mg, 93% yield). 300 MHz $^1$H NMR (CD$_3$OD, ppm) δ 8.10-8.04 (m, 1H), 8.87-7.81 (m, 1H), 7.79-7.71 (m, 1H), 7.55 (dd, J=7.8, 7.8 Hz, 1H), 7.42 (dd, J=4.9, 2.9 Hz, 1H), 7.29-7.25 (m, 1H), 7.10 (dd, J=4.9, 1.3 Hz, 1H), 3.75-3.64 (m, 1H), 3.52-3.42 (m, 1H), 3.40-3.29 (m, 2H), 3.28-3.13 (m, 4H), 2.87 (dd, J=13.4, 9.4 Hz, 1H) 2.80-2.67 (m, 1H), 2.63-2.49 (m, 1H), 2.49-2.38 (m, 1H), 2.46 (s, 6H), 1.96-1.85 (m, 1H). ESI-MS (m/z): 388 [M+H]$^+$.

Example 9: 3-(3-((Dimethylamino)methyl)-4-hydroxy-1-(4-methoxyphenethyl) piperidin-4-yl)benzamide (17), and Corresponding Hydrochloride Salt (17a)

(a) 3-(3-((Dimethylamino)methyl)-4-hydroxy-1-(4-methoxyphenethyl)piperidin-4-yl)benzonitrile (16)

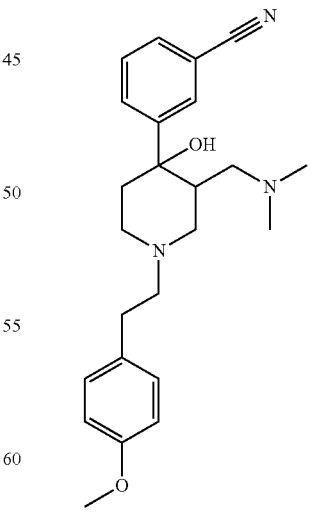

tert-Butyl-4-(3-cyanophenyl)-3-((dimethylamino)methyl)-4-hydroxypiperidine-1-carboxylate (4) (260 mg, 0.72 mmol) was treated with trifluoroacetic acid, then reacted with 2-(4-methoxyphenyl)acetaldehyde using procedure described for compound (8) to afford 3-(3-((dimethylamino)methyl)-4-hydroxy-1-(4-methoxyphenethyl)piperidin-4-yl)benzonitrile (16) (180 mg, 63% yield). 300 MHz $^1$H NMR (CDCl$_3$, ppm): δ 7.96-7.91 (m, 1H), 7.81-7.73 (m, 1H), 7.55 (ddd, J=7.6, 1.4, 1.4 Hz, 1H), 7.46 (dd, J=7.6, 7.6 Hz, 1H), 7.20-7.11 (m, 2H), 6.89-6.79 (m, 2H), 3.80 (s, 3H), 2.96-2.77 (m, 5H), 2.77-2.53 (m, 3H), 2.35 (dd, J=14.0, 4.4 Hz, 1H), 2.30-2.17 (m, 1H), 2.17 (dd, J=14.0, 1.9 Hz, 1H), 2.09 (s, 6H), 2.13-1.89 (m, 2H), 1.67 (dt, J=13.8, 2.7 Hz, 1H). ESI-MS (m/z): 394 [M+H]$^+$.

(b) 3-(3-((Dimethylamino)methyl)-4-hydroxy-1-(4-methoxyphenethyl)piperidin-4-yl)benzamide (17)

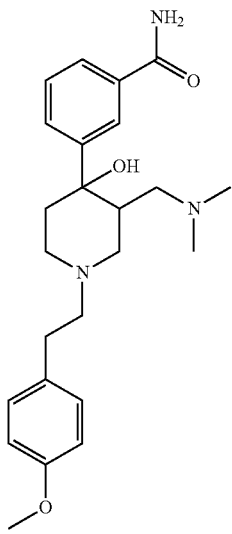 [SMILES: COc1ccc(CCN2CCC(O)(c3cccc(C(N)=O)c3)C(CN(C)C)C2)cc1]

3-(3-((Dimethylamino)methyl)-4-methoxyphenethyl)piperidin-4-yl)benzonitrile (16) (175 mg, 0.45 mmol) was treated with KOH using procedure described for compound (6) to afford 3-(3-((dimethylamino)methyl)-4-hydroxy-1-(4-methoxy phenethyl)piperidin-4-yl) benzamide (17) (182 mg, 99% yield). 300 MHz $^1$H NMR (CDCl$_3$, ppm): δ 8.08-8.02 (m, 1H), 7.78-7.68 (m, 2H), 7.44 (dd, J=7.7, 7.7 Hz, 1H), 7.20-7.10 (m, 2H), 6.91-6.80 (m, 2H), 6.22 (br s, 1H), 5.82 (br s, 1H), 3.79 (s, 3H), 2.93-2.75 (m, 5H), 2.75-2.53 (m, 3H), 2.38 (dd, J=13.9, 4.6 Hz, 1H), 2.30-2.20 (m, 1H), 2.13 (dd, J=14.0, 1.7 Hz, 1H), 2.13-1.93 (m, 2H), 2.08 (s, 6H), 1.74-1.63 (m, 1H). ESI-MS (m/z): 412 [M+H]$^+$.

(c) 3-(3-((Dimethylamino)methyl)-4-hydroxy-1-(4-methoxyphenethyl)piperidin-4-yl)benzamide Hydrochloride (17a)

3-(3-((Dimethylamino)methyl)-4-hydroxy-1-(4-methoxyphenethyl)piperidin-4-yl)benzamide (17) (182 mg, 0.44 mmol) was treated with 2M HCl (in diethyl ether) in diethyl ether/MeOH (15 mL/0.5 mL) using procedure described for compound (6a) to produce 3-(3-((dimethylamino)methyl)-4-hydroxy-1-(4-methoxyphenethyl)piperidin-4-yl)benzamide hydrochloride (17a) (165 mg, 83% yield). 300 MHz $^1$H NMR (CD$_3$OD, ppm): δ 8.12-8.03 (m, 1H), 7.90-7.82 (m, 1H), 7.80-7.72 (m, 1H), 7.57 (dd, J=7.7, 7.7 Hz, 1H), 7.34-7.20 (m, 2H), 6.98-6.88 (m, 2H), 3.81 (s, 3H), 3.74-3.60 (m, 1H), 3.56-3.43 (m, 1H), 3.39-3.02 (m, 6H), 2.89-2.76 (m, 1H), 2.76-2.62 (m, 1H), 2.62-2.29 (m, 2H), 2.42 (s, 6H), 2.00-1.87 (m, 1H). ESI-MS (m/z): 412 [M+H]$^+$.

Example 10: 3-(3-((Dimethylamino)methyl)-4-hydroxy-1-(4-hydroxyphenethyl) piperidin-4-yl)benzamide (18), and Corresponding Hydrochloride Salt (18a)

(a) 3-(3-((Dimethylamino)methyl)-4-hydroxy-1-(4-hydroxyphenethyl)piperidin-4-yl)benzamide (18)

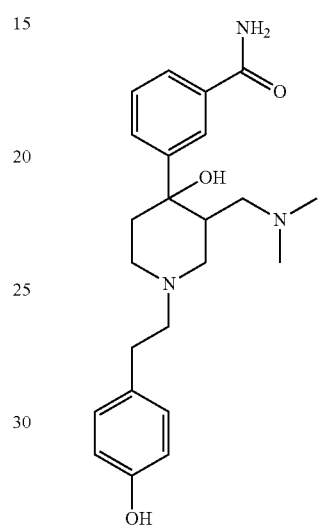

A solution of 3-(3-((dimethylamino)methyl)-4-hydroxy-1-(4-methoxyphenethyl) piperidin-4-yl)benzamide (17) (125 mg, 0.30 mmol) in CH$_2$Cl$_2$ (7 mL) was purged with argon and cooled to 0° C. A solution 1M BBr$_3$ (3.00 mL, 3.00 mmol) in CH$_2$Cl$_2$ was added and resulting solution was stirred at room temperature for 3 h. After this time, MeOH (10 mL) was added dropwise and the mixture was stirred for 1 h. The volatiles were removed via rotary evaporation and the residue was purified by flash chromatography using eluent from CH$_2$Cl$_2$ to CH$_2$Cl$_2$/MeOH (10:90) to yield 3-(3-((dimethylamino)methyl)-4-hydroxy-1-(4-hydroxy phenethyl)piperidin-4-yl)benzamide (18) as colorless foam (110 mg, 91% yield). 300 MHz $^1$H NMR (CD$_3$OD, ppm): δ 8.16-8.03 (m, 1H), 7.90-7.82 (m, 1H), 7.80-7.72 (m, 1H), 7.57 (dd, J=7.7, 7.7 Hz, 1H), 7.34-7.20 (m, 2H), 6.98-6.88 (m, 2H), 3.81 (s, 3H), 3.74-3.60 (m, 1H), 3.56-3.43 (m, 1H), 3.39-3.02 (m, 7H), 2.89-2.76 (m, 1H), 2.76-2.62 (m, 1H), 2.62-2.29 (m, 3H), 2.42 (s, 6H), 2.00-1.87 (m, 1H). ESI-MS (m/z): 412 [M+H]$^+$.

(b) 3-(3-((Dimethylamino)methyl)-4-hydroxy-1-(4-hydroxyphenethyl)piperidin-4-yl)benzamide Hydrochloride (18a)

3-(3-((Dimethylamino)methyl)-4-hydroxy-1-(4-hydroxyphenethyl)piperidin-4-yl)benzamide (18) (105 mg, 0.26 mmol) was treated with 2M HCl (in diethyl ether) in diethyl ether/MeOH (10 mL/5 mL) using procedure described for compound (6a) to produce 3-(3-((dimethylamino)methyl)-4-hydroxy-1-(4-hydroxyphenethyl)piperidin-4-yl)benzamide hydrochloride (18a) (70 mg, 61% yield). 300 MHz $^1$H NMR (CD$_3$OD, ppm): δ 8.14-8.07 (m, 1H), 7.91-7.83 (m, 1H), 7.82-7.75 (m, 1H), 7.59 (dd, J=7.7, 7.7 Hz, 1H), 7.22-7.14 (m, 2H), 6.82-6.73 (m, 2H), 4.10-3.97 (m, 1H), 3.76-3.64 (m, 1H), 3.57-3.37 (m, 5H), 3.24-3.03 (m, 4H), 2.86-2.68 (m, 2H), 2.76 (s, 3H), 2.58 (s, 3H), 2.07-1.95 (m, 1H). ESI-MS (m/z): 412 [M+H]+. ESI-MS (m/z): 412 [M+H]+.

Example 11: 3-[3-Dimethylaminomethyl-4-hydroxy-1-(3-phenyl-propyl)-piperidin-4-yl]-benzamide (20), and Corresponding Hydrochloride Salt (20a)

(a) 3-(3-((Dimethylamino)methyl)-4-hydroxy-1-(3-phenylpropyl)piperidin-4-yl) benzonitrile (19)

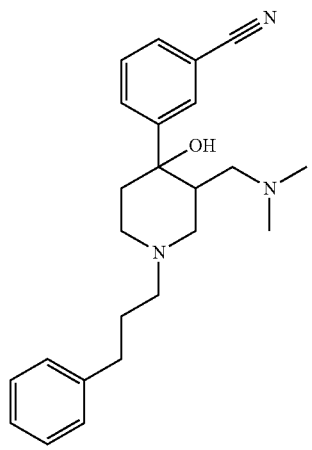 [SMILES: CN(C)CC1CN(CCCc2ccccc2)CCC1(O)c1cccc(C#N)c1]

tert-Butyl-4-(3-cyanophenyl)-3-((dimethylamino) methyl)-4-hydroxypiperidine-1-carboxylate (4) (200 mg, 0.56 mmol) was treated with trifluoroacetic acid, then reacted with 3-phenylpropanal using procedure described for compound (8) to afford 3-(3-((dimethyl amino)methyl)-4-hydroxy-1-(3-phenylpropyl)piperidin-4-yl)benzonitrile (19) (138 mg, 66% yield). 300 MHz $^1$H NMR (CD$_3$OD, ppm): δ 7.93 (s, 1H), 7.80-7.72 (m, 1H), 7.58-7.51 (m, 1H), 7.45 (dd, J=7.7, 7.7 Hz, 1H), 7.34-7.26 (m, 2H), 7.24-7.16 (m, 3H), 3.00-2.40 (m, 8H), 2.34 (dd, J=14.2, 4.5 Hz, 1H), 2.20-2.11 (m, 2H), 2.08 (s, 6H), 2.03-1.77 (m, 3H), 1.70-1.57 (m, 1H). ESI-MS (m/z): 378 [M+H]+.

(b) 3-[3-Dimethylaminomethyl-4-hydroxy-1-(3-phenyl-propyl)-piperidin-4-yl]-benzamide (20)

3-(3-((Dimethylamino)methyl)-4-hydroxy-1-(3-phenylpropyl)piperidin-4-yl) benzonitrile (19) (135 mg, 0.36 mmol) was treated with KOH using procedure described for compound (6) to afford 3-[3-dimethylaminomethyl-4-hydroxy-1-(3-phenyl-propyl)-piperidin-4-yl]-benzamide (20) (141 mg, 100% yield). 300 MHz $^1$H NMR (CD$_3$OD, ppm): δ 8.07-8.03 (m, 1H), 7.79-7.69 (m, 2H), 7.44 (dd, J=7.7, 7.7 Hz, 1H), 7.33-7.27 (m, 2H), 7.25-7.16 (m, 3H), 6.22 (s, 1H), 5.64 (s, 1H), 2.93-2.76 (m, 3H), 2.69 (t, J=7.7 Hz, 2H), 2.65-2.48 (m, 3H), 2.45-2.31 (m, 2H), 2.20-1.89 (m, 5H), 2.07 (s, 6H), 1.75-1.62 (m, 1H). ESI-MS (m/z): 396 [M+H]+.

(c) 3-[3-Dimethylaminomethyl-4-hydroxy-1-(3-phenyl-propyl)-piperidin-4-yl]-benzamide Hydrochloride (20a)

3-[3-Dimethylaminomethyl-4-hydroxy-1-(3-phenyl-propyl)-piperidin-4-yl]-benzamide (20) (135 mg, 0.34 mmol) was treated with 2M HCl (in diethyl ether) in diethyl ether/MeOH (15 mL/0.5 mL) using procedure described for compound (6a) to produce 3-[3-dimethylamino methyl-4-hydroxy-1-(3-phenyl-propyl)-piperidin-4-yl]-benzamide hydrochloride (20a) (132 mg, 90% yield). 300 MHz $^1$H NMR (CD$_3$OD, ppm): δ 8.06-8.00 (m, 1H), 7.86-7.77 (m, 1H), 7.74-7.68 (m, 1H), 7.53 (dd, J=7.8, 7.8 Hz, 1H), 7.35-7.15 (m, 5H), 3.62-3.50 (m, 1H), 3.44-3.35 (m, 1H), 3.25-3.16 (m, 1H), 3.16-2.99 (m, 3H), 2.76 (t, J=7.6 Hz, 2H), 2.71-2.55 (m, 2H), 2.55-2.39 (m, 1H), 2.31 (s, 6H), 2.27-2.05 (m, 3H), 1.94-1.82 (m, 1H). ESI-MS (m/z): 396 [M+H]+.

Example 12: Rac-syn-3-(3-dimethylaminomethyl-4-hydroxy-piperidin-4-yl)-benzamide (rac-syn-21), and Corresponding Hydrochloride Salt (Rac-Syn-21a)

Scheme 5 (absolute stereochemistry not implied).

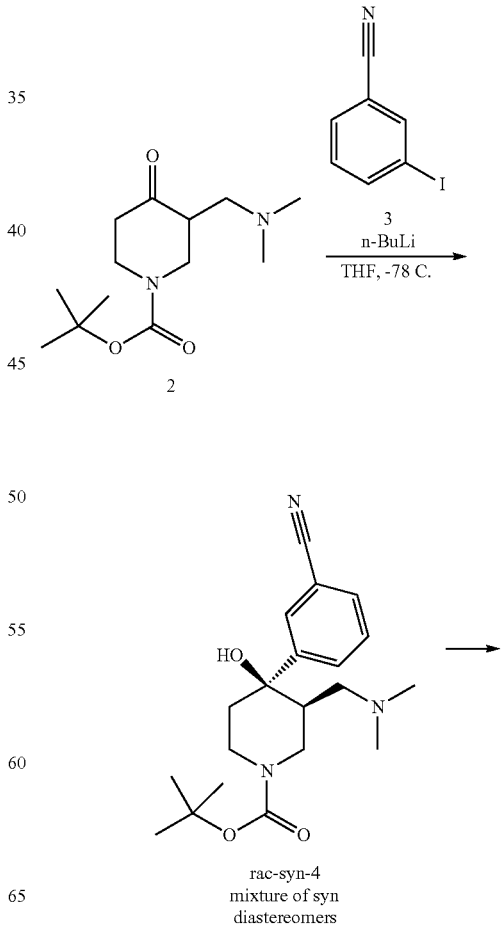

rac-syn-4
mixture of syn
diastereomers

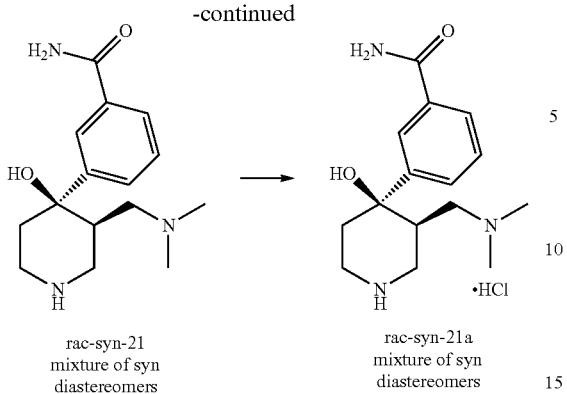

rac-syn-21
mixture of syn
diastereomers rac-syn-21a
mixture of syn
diastereomers (a) Rac-syn-tert-butyl-4-(3-cyanophenyl)-3-((dimethylamino)methyl)-4-hydroxy piperidine-1-carboxylate (rac-syn-4)

An oven-dried round bottom flask was charged with 3-iodobenzonitrile (3) (5.00 g, 21.85 mmol) and purged with argon. THF (60 mL) was added, and the resulting solution was cooled to −78° C. 2.3 M solution of n-BuLi (9.28 mL, 23.21 mmol) was added dropwise (1.7-2.2 mL/min. Then, a solution of tert-butyl-3-((dimethylamino)methyl)-4-oxopiperidine-1-carboxylate (2) (3.50 g, 13.65 mmol) in THF (40 mL) was added dropwise (2.2-2.5 mL/min). The resulting mixture was stirred at −78° C. for 10 min and poured into the stirred mixture of saturated $NH_4C_1$ (30 mL) and $NH_4OH$ (25%, 10 mL). The resulting suspension was extracted with EtOAc (3×30 mL). The combined organic extracts were dried over $Na_2SO_4$. Volatiles were removed, and the residue was purified flash chromatography using gradient elution from $CH_2Cl_2$/diethyl ether (99:1) to $CH_2Cl_2$/diethyl ether (20:80) to give rac-syn-tert-butyl-4-(3-cyanophenyl)-3-((dimethylamino)methyl)-4-hydroxypiperidine-1-carboxylate (rac-syn-4) (2.22 g, 45% yield) as a mixture of enantiomers. ESI-MS (m/z): 360 [M+H]$^+$.

(b) Rac-syn-3-(3-dimethylaminomethyl-4-hydroxy-piperidin-4-yl)-benzamide (rac-syn-21)

Neat trifluoroacetic acid (801 µL, 10.43 mmol) was added to rac-syn-tert-butyl-4-(3-cyanophenyl)-3-((dimethylamino)methyl)-4-hydroxypiperidine-1-carboxylate (rac-syn-4) (250 mg, 0.70 mmol), and the mixture was stirred for 15 min at ambient temperature. Volatiles were then removed. The residue was dissolved in tert-butanol (7 mL), and KOH (383 mg, 6.95 mmol) was added. The suspension was heated at 80° C. for 2 hours. The mixture was extracted with $CH_2CH_2$/$CHCl_3$ (1/1) (6×5 mL). The combined organic extracts were dried over $Na_2SO_4$. Volatiles were removed, and the residue was purified by flash column chromatography using gradient elution from $CH_2Cl_2$/methanol (9:1) to $CH_2Cl_2$/methanol (1:9) to give rac-syn-3-(3-dimethylaminomethyl-4-hydroxy-piperidin-4-yl)-benzamide (rac-syn-21) (87 mg, 45% yield). ESI-MS (m/z): 278 [M+H]$^+$.

(c) Rac-syn-3-(3-dimethylaminomethyl-4-hydroxy-piperidin-4-yl)-benzamidehydrochloride (rac-syn-21a)

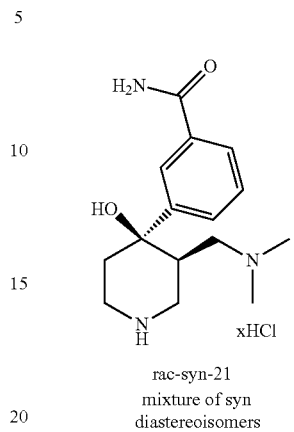

rac-syn-21
mixture of syn
diastereoisomers (Absolute Stereochemistry not Implied)

Rac-syn-3-(3-dimethylaminomethyl-4-hydroxy-piperidin-4-yl)-benzamide (rac-syn-21) (86 mg, 0.31 mmol) was treated with 2M HCl (in diethyl ether) in diethyl ether/methanol (10 mL/0.5 mL) using procedure described for compound 7 to produce rac-syn-3-(3-dimethylaminomethyl-4-hydroxy-piperidin-4-yl)-benzamide hydrochloride (rac-syn-21a) (85 mg, 87% yield). 400 MHz $^1$H NMR (D$_2$O, ppm) 8.01-7.97 (m, 1H), 7.89-7.84 (m, 1H), 7.84-7.79 (m, 1H), 7.67 (dd, J=7.8 Hz, 1H), 3.69 (dd, J=12.8, 4.3 Hz, 1H), 3.55-3.41 (m, 3H), 3.12 (dd, J=14.2, 8.8 Hz, 1H), 2.86 (dd, J=14.2, 1.9 Hz, 1H), 2.80-2.66 (m, 4H), 2.66-2.46 (m, 4H), 2.15-2.01 (m, 1H). ESI-MS (m/z): 278 [M+H]$^+$.

Example 13: Chiral Resolution of rac-syn-tert-butyl-4-(3-cyanophenyl)-3-((dimethyl amino)methyl)-4-hydroxypiperidine-1-carboxylate (4)

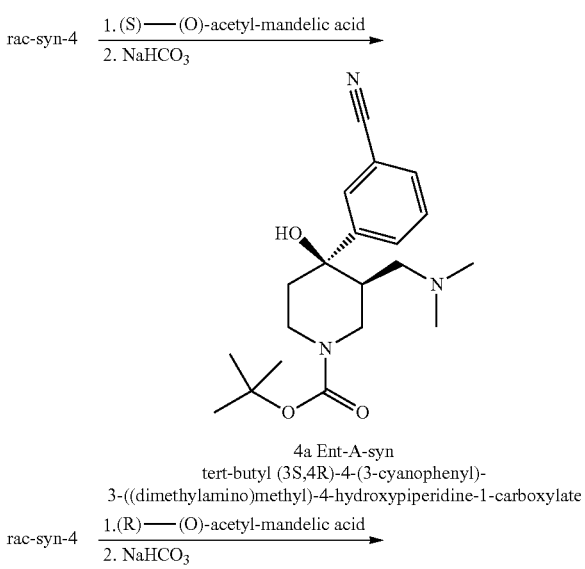

Scheme 6.

rac-syn-4  1. (S)——(O)-acetyl-mandelic acid
           2. NaHCO$_3$

4a Ent-A-syn
tert-butyl (3S,4R)-4-(3-cyanophenyl)-3-((dimethylamino)methyl)-4-hydroxypiperidine-1-carboxylate rac-syn-4  1. (R)——(O)-acetyl-mandelic acid
           2. NaHCO$_3$

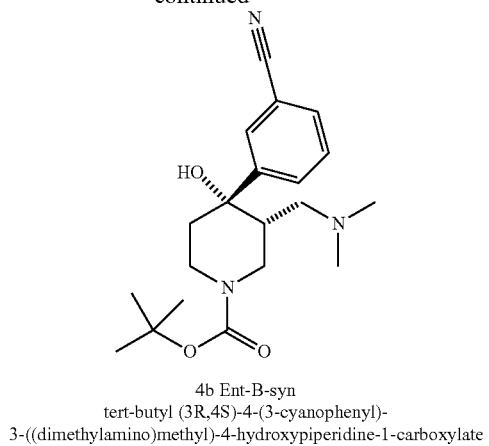

4b Ent-B-syn
tert-butyl (3R,4S)-4-(3-cyanophenyl)-
3-((dimethylamino)methyl)-4-hydroxypiperidine-1-carboxylate

(a) tert-Butyl (3S,4R)-4-(3-cyanophenyl)-3-((dimethylamino)methyl)-4-hydroxypiperidine-1-carboxylate (4a)

Rac-syn-tert-butyl-4-(3-cyanophenyl)-3-((dimethylamino)methyl)-4-hydroxy piperidine-1-carboxylate (rac-syn-4) (4.93 g, 13.71 mmol) was dissolved in hot MeCN (75 mL). Solid (S)—O-acetyl-mandelic acid was added. After solids were dissolved, the solution was cooled and held in a thermostated bath at +3° C. for 60 hours. The formed precipitate was collected by filtration, and washed with small amount of cold MeCN. An aliquot was taken for chiral assay (it was dissolved in 2 mL of $CH_2Cl_2$, and the solution washed with saturated $NaHCO_3$ solution (2 mL); assay shows 93% ee). The material was dissolved in 20 mL of MeCN under reflux and kept in the refrigerator for 14 hours. The precipitate formed was collected by filtration, and washed with small amount of cold MeCN (chiral assay of aliquot shows 97+% ee) to afford {(3S,4R)-[1-tert-butoxycarbonyl-4-(3-cyanophenyl)-4-hydroxy-piperidin-3-yl]methyl-dimethylammonium}-(S)-2-acetoxy-2-phenylacetate (the (S)—O-acetyl-mandelic acid addition salt of tert-butyl (3S,4R)-4-(3-cyanophenyl)-3-((dimethylamino)methyl)-4-hydroxypiperidine-1-carboxylate).

This solid was dissolved in 120 mL $CH_2Cl_2$, and washed with 60 mL of saturated $NaHCO_3$ solution. The aqueous phase was extracted with 30 mL of $CH_2Cl_2$. The combined organics were dried over $MgSO_4$, filtered, and the volatiles were evaporated to give tert-butyl (3S,4R)-4-(3-cyanophenyl)-3-((dimethylamino)methyl)-4-hydroxypiperidine-1-carboxylate (4a) (1.35 g, 27% yield) as a white powder. 300 MHz $^1$H NMR ($CDCl_3$, ppm) 7.89-7.83 (m, 1H), 7.75-7.67 (m, 1H), 7.55 (ddd, J=7.7, 1.4, 1.4 Hz, 1H), 7.46 (dd, J=7.7, 7.7 Hz, 1H), 4.15-3.83 (m, 2H), 3.47 (t, J=12.2 Hz, 1H), 3.28 (t, J=12.1 Hz, 1H), 2.34 (dd, J=14.3, 4.1 Hz, 1H), 2.25 (dd, J=14.3, 1.7 Hz, 1H), 2.09 (s, 6H), 2.05-1.94 (m, 1H), 1.80-1.64 (m, 1H), 1.63-1.53 (m, 1H), 1.49 (s, 9H). ESI-MS (m/z): 360 $[M+H]^+$.

The absolute stereochemistry of tert-butyl (3S,4R)-4-(3-cyanophenyl)-3-((dimethylamino)methyl)-4-hydroxypiperidine-1-carboxylate was inferred from the absolute stereochemical determination of the enantiomer below.

(b) tert-Butyl (3R,4S)-4-(3-cyanophenyl)-3-((dimethylamino)methyl)-4-hydroxy piperidine-1-carboxylate (4b)

Rac-syn-tert-butyl-4-(3-cyanophenyl)-3-((dimethylamino)methyl)-4-hydroxypiperidine-1-carboxylate (rac-syn-4) (1.42 g, 3.95 mmol) was treated with (R)—O-acetylmandelic acid (767 mg, 3.95 mmol) using procedure described for compound 4a to produce {(3R,4S)-[1-tert-butoxycarbonyl-4-(3-cyanophenyl)-4-hydroxy-piperidin-3-yl]methyl-dimethylammonium}-(R)-2-acetoxy-2-phenylacetate (the (R)—O-acetyl-mandelic acid addition salt of tert-butyl (3R,4S)-4-(3-cyanophenyl)-3-((dimethylamino)methyl)-4-hydroxypiperidine-1-carboxylate), which was treated with base as described for compound 4a to obtain tert-butyl (3R,4S)-4-(3-cyanophenyl)-3-((dimethylamino)methyl)-4-hydroxypiperidine-1-carboxylate (4b) (320 mg, 23% yield). 300 MHz $^1$H NMR ($CDCl_3$, ppm) 7.89-7.84 (m, 1H), 7.75-7.68 (m, 1H), 7.55 (ddd, J=7.7, 1.4, 1.4 Hz, 1H), 7.46 (dd, J=7.7, 7.7 Hz, 1H), 4.14-3.85 (m, 2H), 3.48 (t, J=12.2 Hz, 1H), 3.28 (t, J=12.1 Hz, 1H), 2.34 (dd, J=14.3, 4.1 Hz, 1H), 2.25 (dd, J=14.3, 1.7 Hz, 1H), 2.09 (s, 6H), 2.05-1.95 (m, 1H), 1.80-1.64 (m, 1H), 1.63-1.53 (m, 1H), 1.50 (s, 9H). ESI-MS (m/z): 360 $[M+H]^+$.

Figure 11:
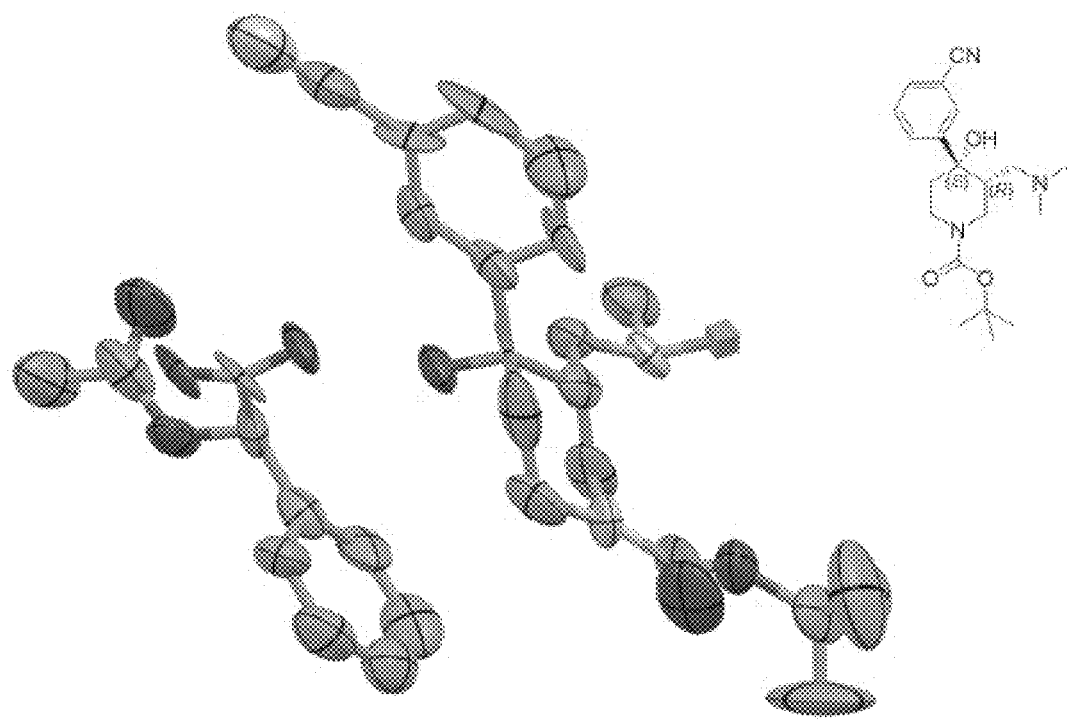
FIG. 11 illustrates a X-ray structure of compound (4b) Ent-B-syn: {(3R,4S)-[1-tert-butoxycarbonyl-4-(3-cyanophenyl)-4-hydroxy-piperidin-3-yl]methyl-dimethylammonium}-(R)-2-acetoxy-2-phenylacetate, which is the (R)—O-acetyl-mandelic acid addition salt of tert-butyl (3R,4S)-4-(3-cyanophenyl)-3-((dimethylamino)methyl)-4-hydroxypiperidine-1-carboxylate.

Crystalline {(3R,4S)-[1-tert-butoxycarbonyl-4-(3-cyanophenyl)-4-hydroxy-piperidin-3-yl]methyl-dimethylammonium}-(R)-2-acetoxy-2-phenylacetate was subjected to X-ray diffraction pattern determination and analysis, which indicated absolute stereochemistry to be (3R, 4S) as shown in FIG. 11. It was inferred that products derived from these intermediate retain the absolute stereochemistry (no racemization was observed).

Example 14: 3-(1-(3-(2-Chloro-4-fluoro-phenyl)-propyl)-3-dimethylaminomethyl-4-hydroxy-piperidin-4-yl)benzamide (23), and Corresponding Hydrochloride Salt (24)

Scheme 7.

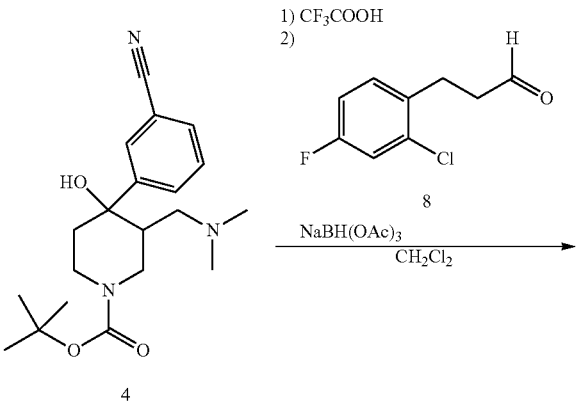

-continued

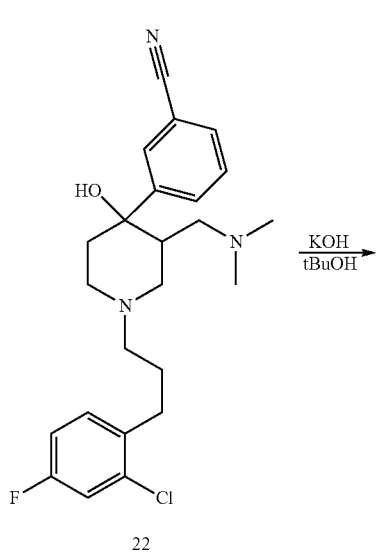

22

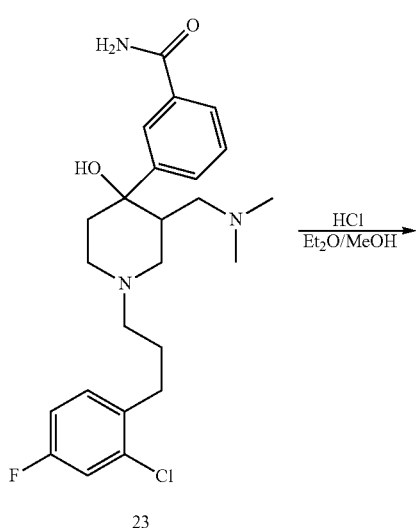

23

-continued

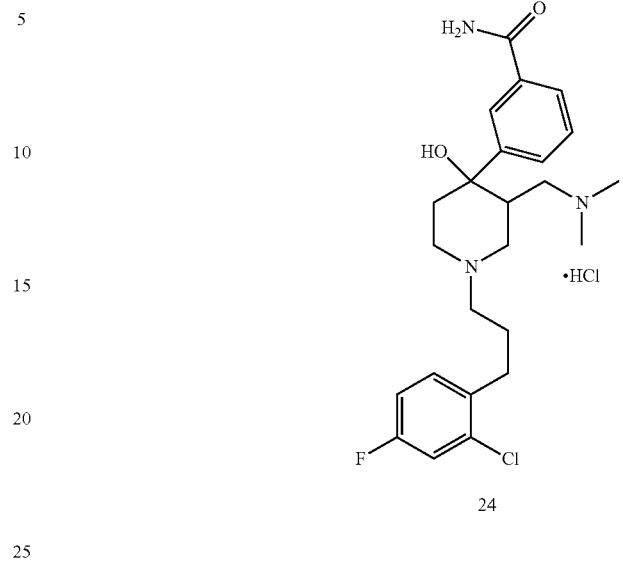

24

(a) 3-(1-(3-(2-Chloro-4-fluorophenyl)propyl)-3-((dimethylamino)methyl)-4-hydroxypiperidin-4-yl)benzonitrile (22)

Trifluoroacetic acid (1.28 mL, 16.69 mmol) was added to a solution of tert-butyl-4-(3-cyanophenyl)-3-((dimethylamino)methyl)-4-hydroxypiperidine-1-carboxylate (4) (400 mg, 1.11 mmol) in $CH_2Cl_2$ (10 mL), and the resulting mixture was stirred for 1 h at ambient temperature. Volatiles were removed, and the residue was dissolved in $CH_2Cl_2$ (10 mL). TEA (930 µL, 6.68 mmol) was added, and the mixture was stirred for 5 min. Acetic acid (127 µl, 2.23 mmol), 3-(2-chloro-4-fluorophenyl)propanal (415 mg, 2.23 mmol), and $NaBH(OAc)_3$ (943 mg, 4.45 mmol) were added, and the resulting suspension was stirred at ambient temperature for 18 h. Saturated $NaHCO_3$ solution (30 mL) was added, and the suspension was extracted with $CH_2Cl_2$ (2×20 mL). The combined organic extracts were washed with water (30 mL) and dried over $Na_2SO_4$. Volatiles were removed, and the residue was purified by flash column chromatography using gradient elution from $CH_2Cl_2$/methanol (99:1) to $CH_2Cl_2$/methanol (1:1) to give 3-(1-(3-(2-chloro-4-fluorophenyl)propyl)-3-((dimethylamino)methyl)-4-hydroxypiperidin-4-yl)benzonitrile (22) (478 mg, 65% yield). 300 MHz $^1$H NMR ($CDCl_3$, ppm) 7.92 (s, 1H), 7.75 (d, J=7.7 Hz, 1H), 7.57-7.51 (m, 1H), 7.45 (dd, J=7.7, 7.7 Hz, 1H), 7.21 (dd, J=8.6, 6.2 Hz, 1H), 7.10 (dd, J=8.6, 2.6 Hz, 1H), 6.92 (ddd, J=8.2, 8.2, 2.6 Hz, 1H), 2.87-2.62 (m, 5H), 2.58-2.41 (m, 3H), 2.34 (dd, J=14.2, 4.6 Hz, 1H), 2.22-2.12 (m, 2H), 2.09 (s, 6H), 1.95-1.79 (m, 3H), 1.70-1.59 (m, 1H), 1.34-1.16 (m, 1H). ESI-MS (m/z): 430, 432 [M+H]$^+$.

(b) 3-(1-(3-(2-Chloro-4-fluoro-phenyl)-propyl)-3-dimethylaminomethyl-4-hydroxy-piperidin-4-yl))benzamide (23)

Ground KOH (278 mg, 5.05 mmol) was added to a solution of rac-syn-3-(1-(3-(2-chloro-4-fluorophenyl)propyl)-3-((dimethylamino)methyl)-4-hydroxypiperidin-4-yl)benzonitrile (22) (310 mg. 0.72 mmol) in tert-butanol (10 mL), and the reaction mixture was heated for 2 hours at 80° C. Brine (5 mL) was added, and the resulting suspension was extracted with EtOAc (3×6 mL). The combined organic extracts were dried over $Na_2SO_4$, and volatiles were removed to give rac-syn-3-(1-(3-(2-chloro-4-fluoro-phenyl)-propyl)-3-dimethylaminomethyl-4-hydroxy-piperidin-4-yl))benzamide (23) (283 mg, 88% yield). ESI-MS (m/z): 448, 450 $[M+H]^+$.

(c) 3-(1-(3-(2-Chloro-4-fluoro-phenyl)-propyl)-3-dimethylaminomethyl-4-hydroxy-piperidin-4-yl))benzamide Hydrochloride (24)

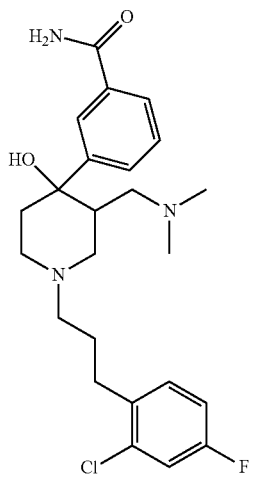 [SMILES: CN(C)CC1CN(CCCc2ccc(F)cc2Cl)CCC1(O)c1cccc(C(N)=O)c1]

3-(1-(3-(2-chloro-4-fluoro-phenyl)-propyl)-3-dimethylaminomethyl-4-hydroxy-piperidin-4-yl))benzamide (23) (12 mg, 0.027 mmol) was treated with 2M HCl (in diethyl ether) in diethyl ether/methanol (10 mL/0.5 mL) using procedure described for compound 7 to produce 3-(1-(3-(2-chloro-4-fluoro-phenyl)-propyl)-3-dimethylamino methyl-4-hydroxy-piperidin-4-yl))benzamide hydrochloride (24) (12 mg, 99% yield). 300 MHz $^1$H NMR ($CD_3OD$, ppm) 8.05-7.99 (m, 1H), 7.79 (dd, J=7.8 Hz, 1H), 7.70 (d, J=7.8 Hz, 1H), 7.50 (dd, J=7.8, 7.8 Hz, 1H), 7.38 (dd, J=8.7, 6.3 Hz, 1H), 7.22 (dd, J=8.7, 2.5 Hz, 1H), 7.05 (ddd, J=8.3, 8.3, 2.5 Hz, 1H), 3.35-3.23 (m, 1H, overlapped with MeOD), 3.20-3.05 (m, 1H), 2.95-2.80 (m, 5H), 2.77-2.68 (m, 1H), 2.64-2.50 (m, 1H), 2.46-2.38 (m, 1H), 2.30 (td, J=13.7, 4.5 Hz, 1H), 2.20 (s, 6H), 2.10-1.93 (m, 3H), 1.84-1.74 (m, 1H). ESI-MS (m/z): 448, 450 $[M+H]^+$.

Example 15: 3-((3S,4R)-1-(3-(2-Chloro-4-fluorophenyl)propyl)-3-((dimethylamino)methyl)-4-hydroxypiperidin-4-yl)benzamide (23a), and corresponding hydrochloride salt (24a)

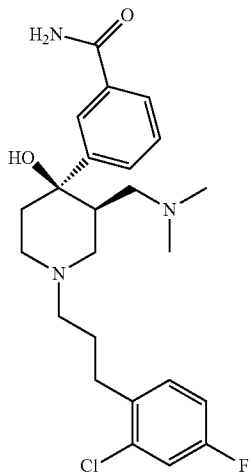 [SMILES: CN(C)C[C@H]1CN(CCCc2ccc(F)cc2Cl)CC[C@]1(O)c1cccc(C(N)=O)c1]

(a) 3-((3S,4R)-1-(3-(2-Chloro-4-fluorophenyl)propyl)-3-((dimethylamino)methyl)-4-hydroxypiperidin-4-yl)benzonitrile (22a)

tert-Butyl (3S,4R)-4-(3-cyanophenyl)-3-((dimethylamino)methyl)-4-hydroxy piperidine-1-carboxylate (4a) (850 mg. 2.36 mmol) was treated with trifluoroacetic acid, and then reacted with 3-(2-chloro-4-fluorophenyl)propanal (706 mg, 3.28 mmol) using procedure described for compound 23 to afford 3-((3S,4R)-1-(3-(2-chloro-4-fluorophenyl)propyl)-3-((dimethylamino)methyl)-4-hydroxypiperidin-4-yl)benzonitrile (22a) (750 mg, 74% yield). ESI-MS (m/z): 430, 432 $[M+H]^+$.

(b) 3-((3S,4R)-1-(3-(2-Chloro-4-fluorophenyl)propyl)-3-((dimethylamino)methyl)-4-hydroxypiperidin-4-yl)benzamide (23a)

3-((3S,4R)-1-(3-(2-Chloro-4-fluorophenyl)propyl)-3-((dimethylamino)methyl)-4-hydroxypiperidin-4-yl)benzonitrile (22a) (750 mg, 1.74 mmol) was treated with KOH (673 mg, 12.21 mmol) using procedure described for compound 23 to afford 3-((3S,4R)-1-(3-(2-chloro-4-fluorophenyl)propyl)-3-((dimethylamino)methyl)-4-hydroxypiperidin-4-yl)benzamide (23a) (700 mg, 90% yield). ESI-MS (m/z): 448, 450 $[M+H]^+$.

(c) 3-((3S,4R)-1-(3-(2-Chloro-4-fluorophenyl)propyl)-3-((dimethylamino)methyl)-4-hydroxypiperidin-4-yl)benzamide Hydrochloride (24a)

3-((3S,4R)-1-(3-(2-Chloro-4-fluorophenyl)propyl)-3-((dimethylamino)methyl)-4-hydroxypiperidin-4-yl)benzamide (23a) (700 mg, 1.56 mmol) was treated with 2M HCl (in diethyl ether) in diethyl ether/methanol (20 mL/1 mL) using procedure described for compound 7 to produce 3-((3S,4R)-1-(3-(2-chloro-4-fluorophenyl)propyl)-3-((dimethylamino)methyl)-4-hydroxypiperidin-4-yl)benzamide hydrochloride (24a). 300 MHz $^1$H NMR ($CD_3OD$, ppm) 8.08-8.03 (m, 1H), 7.86-7.79 (m, 1H), 7.77-7.68 (m, 1H), 7.54 (dd, J=7.8, 7.8 Hz, 1H), 7.43 (dd, J=8.6, 6.1 Hz, 1H), 7.23 (dd, J=8.6, 2.6 Hz, 1H), 7.07 (ddd, J=8.4, 8.4, 2.6 Hz, 1H), 3.72-3.59 (m, 1H), 3.51-3.37 (m, 1H), 3.35-3.05 (m, 4H), 2.94-2.80 (m, 3H), 2.80-2.68 (m, 1H), 2.63-2.35 (m, 2H), 2.44 (s, 6H), 2.24-2.06 (m, 2H), 1.96-1.83 (m, 1H). ESI-MS (m/z): 448, 450 [M+H]$^+$. [$\alpha_D^{20}$]=+13.7 (0.44, methanol).

Example 16: 3-((3R,4S)-1-(3-(2-Chloro-4-fluorophenyl)propyl)-3-((dimethylamino) methyl)-4-hydroxypiperidin-4-yl)benzamide (23b), and Corresponding Hydrochloride Salt (24b)

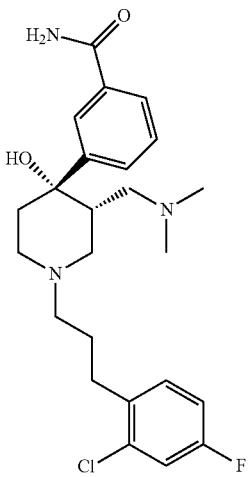 [SMILES: CN(C)C[C@@H]1CN(CCCc2ccc(F)cc2Cl)CC[C@@]1(O)c1cccc(C(N)=O)c1]

(a) 3-((3R,4S)-1-(3-(2-Chloro-4-fluorophenyl)propyl)-3-((dimethylamino)methyl)-4-hydroxypiperidin-4-yl)benzamide (23b)

Rac-syn-3-(1-(3-(2-Chloro-4-fluoro-phenyl)-propyl)-3-dimethylaminomethyl-4-hydroxy-piperidin-4-yl))benzamide (23) was separated into individual diastereoisomers on chiral stationary phase chromatography using (Daicel CHIRALPAK® ID 250 mm×30 mm) column and Hex/IPA (9:1)+0.1% NH$_2$CH$_2$CH$_2$OH as mobile phase on Shimadzu LC-8A: Rt stereoisomer (+) (23a)=27 min, Rt stereoisomer (−) (23b)=32 min at 40 mL/min flow rate.

(b) 3-((3R,4S)-1-(3-(2-Chloro-4-fluorophenyl)propyl)-3-((dimethylamino)methyl)-4-hydroxypiperidin-4-yl)benzamide Hydrochloride (24b)

3-((3R,4S)-1-(3-(2-Chloro-4-fluorophenyl)propyl)-3-((dimethylamino)methyl)-4-hydroxypiperidin-4-yl)benzamide (23b) (150 mg, 0.33 mmol) was treated with 2M HCl (in diethyl ether) in diethyl ether/methanol (10 mL/0.5 mL) using procedure described for compound 7 to produce 3-((3R,4S)-1-(3-(2-chloro-4-fluorophenyl)propyl)-3-((dimethylamino)methyl)-4-hydroxypiperidin-4-yl)benzamide hydrochloride (24b) (112 mg, 69% yield). 400 Hz $^1$H NMR (CD$_3$OD, ppm) 8.08-8.03 (m, 1H), 7.86-7.81 (m, 1H), 7.77-7.70 (m, 1H), 7.55 (dd, J=7.8, 7.8 Hz, 1H), 7.46-7.39 (m, 1H), 7.24 (dd, J=8.7, 2.5 Hz, 1H), 7.07 (ddd, J=8.3, 8.3, 2.5 Hz, 1H), 3.80-3.58 (m, 1H), 3.57-3.39 (m, 1H), 3.38-3.07 (m, 4H), 3.00-2.83 (m, 3H), 2.83-2.67 (m, 1H), 2.67-2.30 (m, 2H), 2.49 (s, 6H), 2.25-2.06 (m, 2H), 1.99-1.86 (m, 1H). ESI-MS (m/z): 448, 450 [M+H]$^+$. [$\alpha_D^{20}$]=−10.3 (1.04, acetone). The absolute stereochemistry is inferred from the enantiomer (Example 15) above.

Example 17: 3-[(3S,4R)-3-Dimethylaminomethyl-1-(5-fluoro-pyridin-3-ylmethyl)-4-hydroxy-piperidin-4-yl]-benzamide (26a), and Corresponding Hydrochloride Salt (27a)

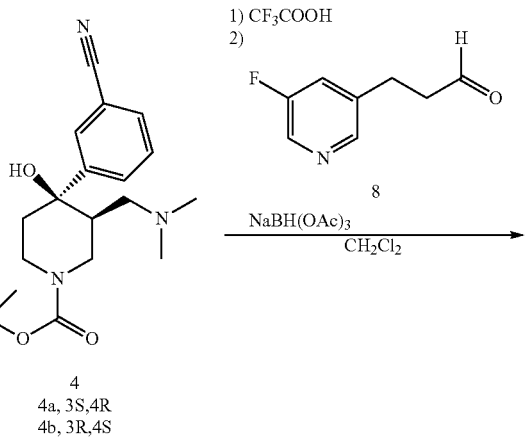

Scheme 8.

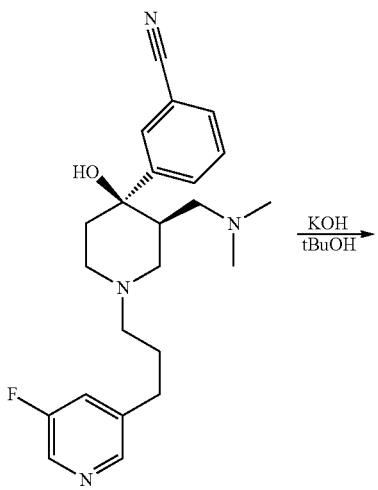

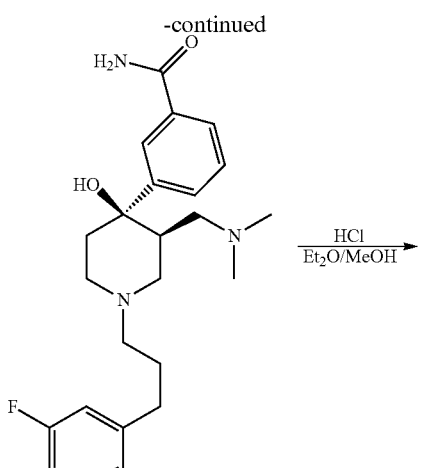

26a, 3S,4R (+)-ent
26b, 3R,4S (-)-ent

HCl
Et₂O/MeOH →

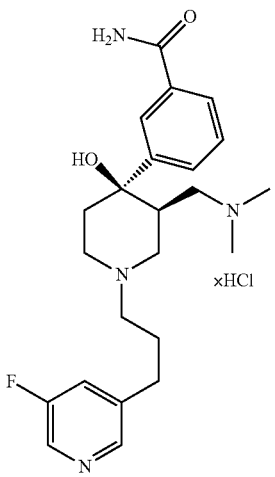

27a, 3S,4R (+)-ent
27b, 3R,4S (-)-ent (a) 3-((3S,4R)-3-((dimethylamino)methyl)-1-(3-(5-fluoropyridin-3-yl)propyl)-4-hydroxypiperidin-4-yl) benzonitrile (25a)

tert-Butyl (3S,4R)-4-(3-cyanophenyl)-3-((dimethylamino)methyl)-4-hydroxypiperidine-1-carboxylate (4a) (260 mg. 0.72 mmol) was treated with trifluoroacetic acid, then reacted with 3-(5-fluoropyridin-3-yl)propanal (133 mg, 0.87 mmol) using procedure described for compound 23 to afford 33-((3S,4R)-3-((Dimethylaminomethyl)-1-(3-(5-fluoropyridin-3-yl)propyl)-4-hydroxypiperidin-4-yl)benzonitrile (25a) (220 mg, 77% yield). ESI-MS (m/z): 397 [M+H]⁺.

(b) 3-[(3S,4R)-3-Dimethylaminomethyl-1-(5-fluoro-pyridin-3-ylmethyl)-4-hydroxy-piperidin-4-yl]-benzamide (26a)

3-((3S,4R)-3-((Dimethylaminomethyl)-1-(3-(5-fluoro-pyridin-3-yl)propyl)-4-hydroxypiperidin-4-yl)benzonitrile (25a) (215 mg, 0.54 mmol) was treated with KOH (209 mg, 3.80 mmol) using procedure described for compound 23 to afford 3-[(3S,4R)-3-dimethylaminomethyl-1-(5-fluoro-pyridin-3-ylmethyl)-4-hydroxy-piperidin-4-yl]-benzamide (26a) (205 mg, 910% yield). ESI-MS (m/z): 415 [M+H]⁺.

(c) 3-[(3S,4R)-3-Dimethylaminomethyl-1-(5-fluoro-pyridin-3-ylmethyl)-4-hydroxy-piperidin-4-yl]-benzamide Hydrochloride (27a)

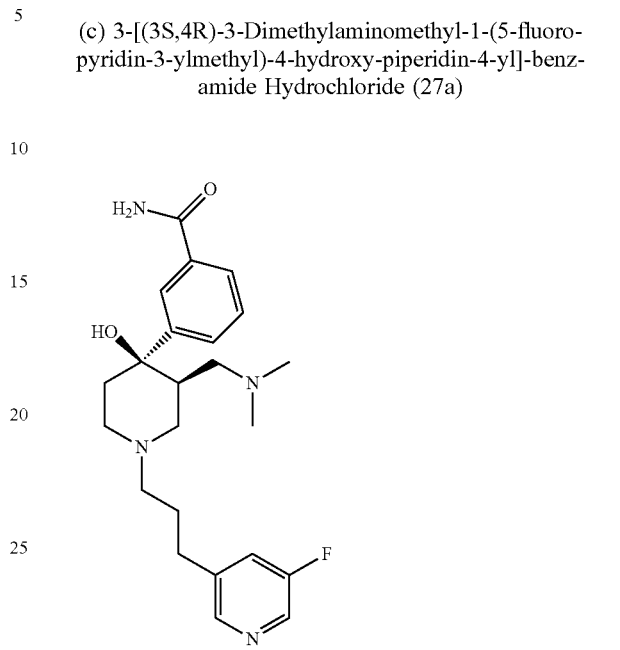

3-[(3S,4R)-3-Dimethylaminomethyl-1-(5-fluoro-pyridin-3-ylmethyl)-4-hydroxy-piperidin-4-yl]-benzamide (26a) (200 mg, 0.48 mmol) was treated with 2M HCl (in diethyl ether) in diethyl ether/methanol (10 mL/3 mL) using procedure described for compound 7 to produce 3-[(3S,4R)-3-dimethylaminomethyl-1-(5-fluoro-pyridin-3-ylmethyl)-4-hydroxy-piperidin-4-yl]-benzamide hydrochloride (27a) (17 mg, 78% yield). 300 MHz ¹H NMR (CD₃OD, ppm) 8.39-8.32 (m, 2H), 8.08-8.02 (m, 1H), 7.86-7.79 (m, 1H), 7.77-7.69 (m, 1H), 7.69-7.62 (m, 1H), 7.54 (dd, J=7.8, 7.8 Hz, 1H), 3.72-3.56 (m, 1H), 3.49-3.36 (m, 1H), 3.26-3.00 (m, 4H), 2.94-2.80 (m, 3H), 2.80-2.66 (m, 1H), 2.62-2.34 (m, 2H), 2.47 (s, 6H), 2.26-2.09 (m, 2H), 1.99-1.84 (m, 1H). ESI-MS (m/z): 415[M+H]⁺. [α$_D^{20}$]=+23.6 (0.42, methanol).

Example 18: 3-[(3R,4S)-3-Dimethylaminomethyl-1-(5-fluoro-pyridin-3-ylmethyl)-4-hydroxy-piperidin-4-yl]-benzamide (26b), and Corresponding Hydrochloride Salt (27b)

(a) 3-((3R,4S)-3-((Dimethylamino)methyl)-1-(3-(5-fluoropyridin-3-yl)propyl)-4-hydroxypiperidin-4-yl) benzonitrile (25b)

tert-Butyl (3R,4S)-4-(3-cyanophenyl)-3-((dimethylamino)methyl)-4-hydroxypiperidine-1-carboxylate (4b) (260 mg. 0.72 mmol) was treated with trifluoroacetic acid, then reacted with 3-(5-fluoropyridin-3-yl)propanal (133 mg, 0.87 mmol) using procedure described for compound 23 to afford 3-((3R,4S)-3-((dimethylamino)methyl)-1-(3-(5-fluoropyridin-3-yl)propyl)-4-hydroxypiperidin-4-yl)benzonitrile (25b) (215 mg, 75% yield). ESI-MS (m/z): 397 [M+H]⁺.

(b) 3-[(3R,4S)-3-Dimethylaminomethyl-1-(5-fluoro-pyridin-3-ylmethyl)-4-hydroxy-piperidin-4-yl]-benzamide (26b)

3-((3R,4S)-3-((Dimethylamino)methyl)-1-(3-(5-fluoro-pyridin-3-yl)propyl)-4-hydroxypiperidin-4-yl)benzonitrile (25b) (210 mg, 0.53 mmol) was treated with KOH (204 mg, 3.70 mmol) using procedure described for compound 23 to afford 3-[(3R,4S)-3-dimethylaminomethyl-1-(5-fluoro-pyridin-3-ylmethyl)-4-hydroxy-piperidin-4-yl]-benzamide (26b) (205 mg, 93% yield). ESI-MS (m/z): 415 [M+H]+.

(c) 3-[(3R,4S)-3-Dimethylaminomethyl-1-(5-fluoro-pyridin-3-ylmethyl)-4-hydroxy-piperidin-4-yl]-benzamide Hydrochloride (27b)

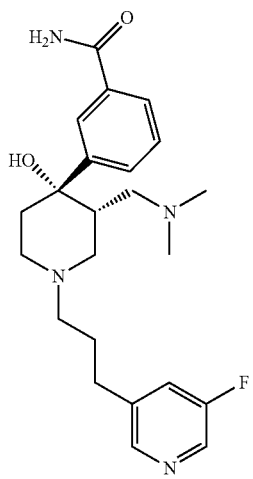 [SMILES: CN(C)C[C@@H]1CN(CCCc2cncc(F)c2)CC[C@@]1(O)c1cccc(C(N)=O)c1]

3-[(3R,4S)-3-Dimethylaminomethyl-1-(5-fluoro-pyridin-3-ylmethyl)-4-hydroxy-piperidin-4-yl]-benzamide (26b) (200 mg, 0.48 mmol) was treated with 2M HCl (in diethyl ether) in diethyl ether/methanol (10 mL/3 mL) using procedure described for compound 7 to produce 3-[(3R,4S)-3-dimethylaminomethyl-1-(5-fluoro-pyridin-3-ylmethyl)-4-hydroxy-piperidin-4-yl]-benzamide hydrochloride (27b) (170 mg, 78% yield). 300 MHz $^1$H NMR (CD$_3$OD, ppm) 8.39-8.29 (m, 2H), 8.09-8.01 (m, 1H), 7.86-7.79 (m, 1H), 7.77-7.69 (m, 1H), 7.69-7.62 (m, 1H), 7.54 (dd, J=7.8, 7.8 Hz, 1H), 3.66-3.51 (m, 1H), 3.42-3.25 (m, 1H), 3.23-2.96 (m, 4H), 2.92-2.76 (m, 3H), 2.76-2.60 (m, 1H), 2.60-2.28 (m, 2H), 2.42 (s, 6H), 2.25-2.06 (m, 2H), 1.95-1.82 (m, 1H). ESI-MS (m/z): 415[M+H]+. $[\alpha_D^{20}]$=−14.1 (0.54, methanol).

Example 19: 3-[(3S,4R)-3-Dimethylaminomethyl-1-(5-fluoro-pyridin-3-ylmethyl)-4-hydroxy-piperidin-4-yl]-benzamide (29a), and Corresponding Hydrochloride Salt (30a)

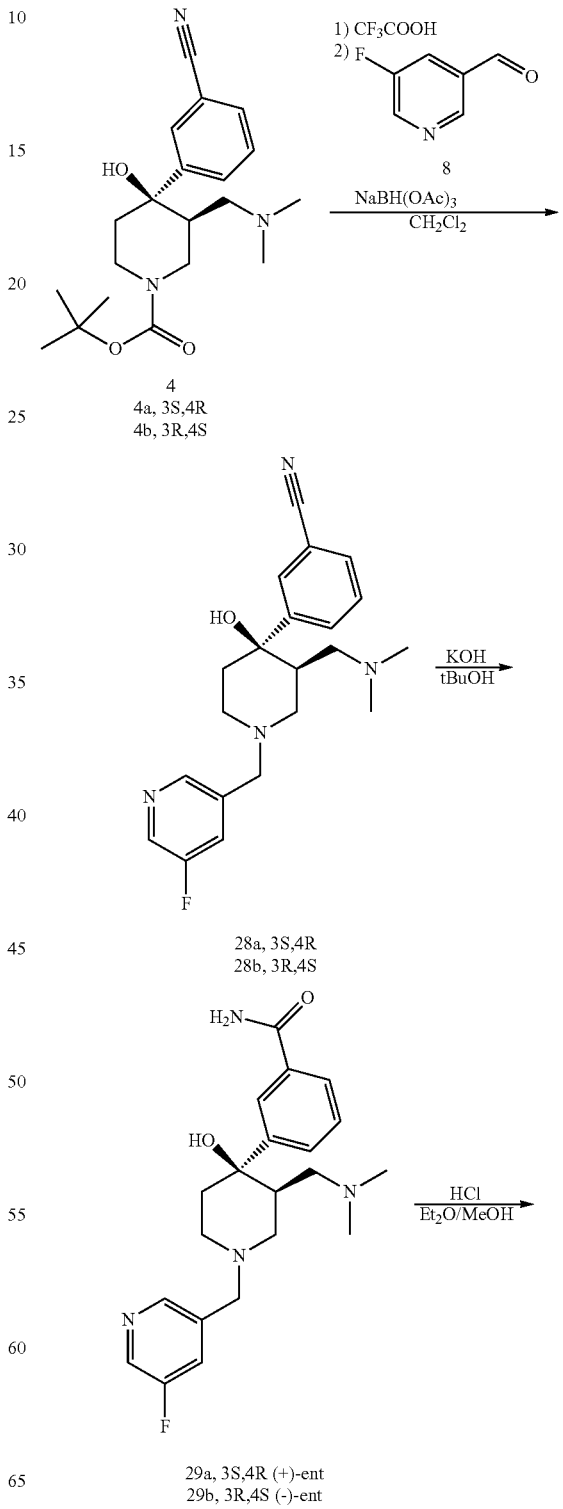

(c) 3-[(3S,4R)-3-Dimethylaminomethyl-1-(5-fluoro-pyridin-3-ylmethyl)-4-hydroxy-piperidin-4-yl]-benzamide Hydrochloride (30a)

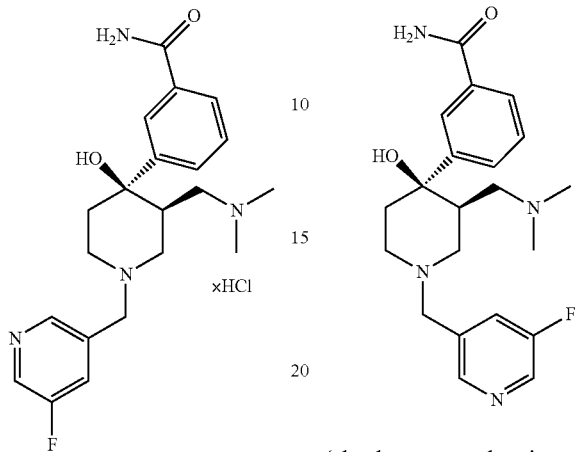

30a, 3S,4R (+)-ent
30b, 3R,4S (−)-ent (absolute stereochemistry inferred)

3-[(3S,4R)-3-Dimethylaminomethyl-1-(5-fluoro-pyridin-3-ylmethyl)-4-hydroxy-piperidin-4-yl]-benzamide (29a) (180 mg, 0.47 mmol) was treated with 2M HCl (in diethyl ether) in diethyl ether/methanol (20 mL/1.5 mL) using procedure described for compound 7 to produce 3-[(3S,4R)-3-dimethylaminomethyl-1-(5-fluoro-pyridin-3-ylmethyl)-4-hydroxy-piperidin-4-yl]-benzamide hydrochloride (30a) (165 mg, 84% yield). 300 MHz $^1$H NMR (CD$_3$OD, ppm) 8.49 (s, 1H), 8.45 (d, J=2.7 Hz, 1H), 8.10-8.03 (m, 1H), 7.88-7.72 (m, 3H), 7.53 (dd, J=7.8, 7.8 Hz, 1H), 3.90 (s, 2H), 3.16-2.96 (m, 2H), 2.96-2.86 (m, 1H), 2.85-2.50 (m, 4H), 2.60 (s, 6H), 2.49-2.32 (m, 1H), 1.88-1.72 (m, 1H). ESI-MS (m/z): 387 [M+H]$^+$. $[\alpha_D^{20}]$=+26.9 (0.55, methanol).

Example 20: 3-[(3R,4S)-3-Dimethylaminomethyl-1-(5-fluoro-pyridin-3-ylmethyl)-4-hydroxy-piperidin-4-yl]-benzamide (29b), and Corresponding Hydrochloride Salt (30b)

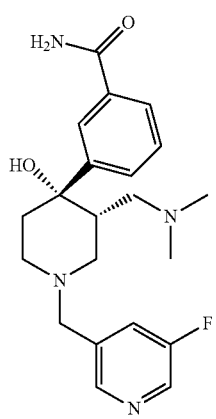 [SMILES: CN(C)C[C@@H]1CN(Cc2cncc(F)c2)CC[C@@]1(O)c1cccc(C(N)=O)c1]

(a) 3-((3R,4S)-3-((Dimethylamino)methyl)-1-((5-fluoropyridin-3-yl)methyl)-4-hydroxypiperidin-4-yl)benzonitrile (28b)

tert-Butyl (3R,4S)-4-(3-cyanophenyl)-3-((dimethylamino)methyl)-4-hydroxypiperidine-1-carboxylate (4b)

(a) 3-((3S,4R)-3-((Dimethylamino)methyl)-1-((5-fluoropyridin-3-yl)methyl)-4-hydroxypiperidin-4-yl)benzonitrile (28a)

tert-Butyl (3S,4R)-4-(3-cyanophenyl)-3-((dimethylamino)methyl)-4-hydroxypiperidine-1-carboxylate (4a) (290 mg. 0.78 mmol) was treated with trifluoroacetic acid, then reacted with 5-fluoronicotinaldehyde (130 μL, 1.17 mmol) using procedure described for compound 23 to produce 3-((3S,4R)-3-((dimethylamino)methyl)-1-((5-fluoropyridin-3-yl)methyl)-4-hydroxypiperidin-4-yl)benzonitrile (28a) (225 mg, 78% yield). ESI-MS (m/z): 369 [M+H]$^+$.

(b) 3-[(3S,4R)-3-Dimethylaminomethyl-1-(5-fluoro-pyridin-3-ylmethyl)-4-hydroxy-piperidin-4-yl]-benzamide (29a)

3-((3S,4R)-3-((Dimethylamino)methyl)-1-((5-fluoropyridin-3-yl)methyl)-4-hydroxypiperidin-4-yl)benzonitrile (28a) (225 mg, 0.61 mmol) was treated with KOH (336 mg, 6.11 mmol) using procedure described for compound 23 to afford 3-[(3S,4R)-3-dimethylaminomethyl-1-(5-fluoro-pyridin-3-ylmethyl)-4-hydroxy-piperidin-4-yl]-benzamide (29a) (185 mg, 78% yield). ESI-MS (m/z): 387 [M+H]$^+$.

(280 mg. 0.78 mmol) was treated with trifluoroacetic acid, then reacted with 5-fluoronicotinaldehyde (130 μL, 1.17 mmol) using procedure described for compound 23 to give 3-((3R,4S)-3-((dimethylamino)methyl)-1-((5-fluoropyridin-3-yl)methyl)-4-hydroxypiperidin-4-yl)benzonitrile (28b) (218 mg, 76% yield). ESI-MS (m/z): 369 [M+H]⁺.

(b) 3-[(3R,4S)-3-Dimethylaminomethyl-1-(5-fluoro-pyridin-3-ylmethyl)-4-hydroxy-piperidin-4-yl]-benzamide (29b)

3-((3R,4S)-3-((Dimethylamino)methyl)-1-((5-fluoropyridin-3-yl)methyl)-4-hydroxypiperidin-4-yl)benzonitrile (28b) (215 mg, 0.58 mmol) was treated with KOH (322 mg, 5.84 mmol) using procedure described for compound 23 to afford 3-[(3R,4S)-3-dimethylaminomethyl-1-(5-fluoro-pyridin-3-ylmethyl)-4-hydroxy-piperidin-4-yl]-benzamide (29b) (180 mg, 80% yield). ESI-MS (m/z): 387 [M+H]⁺.

(c) 3-[(3R,4S)-3-Dimethylaminomethyl-1-(5-fluoro-pyridin-3-ylmethyl)-4-hydroxy-piperidin-4-yl]-benzamide Hydrochloride (30b)

3-[(3R,4S)-3-Dimethylaminomethyl-1-(5-fluoro-pyridin-3-ylmethyl)-4-hydroxy-piperidin-4-yl]-benzamide (29b) (170 mg, 0.44 mmol) was treated with 2M HCl (in diethyl ether) in diethyl ether/methanol (25 mL/1.5 mL) using procedure described for compound 7 to produce 3-[(3R,4S)-3-dimethylaminomethyl-1-(5-fluoro-pyridin-3-ylmethyl)-4-hydroxy-piperidin-4-yl]-benzamide hydrochloride (30b) (156 mg, 84% yield). 300 MHz ¹H NMR (CD₃OD, ppm) 8.48-8.43 (m, 1H), 8.40 (d, J=2.7 Hz, 1H), 8.10-8.03 (m, 1H), 7.83-7.70 (m, 3H), 7.51 (dd, J=7.8, 7.8 Hz, 1H), 3.77 (s, 2H), 2.99 (dd, J=10.7, 2.7 Hz, 1H), 2.89-2.73 (m, 2H), 2.64 (td, J=11.7, 2.7 Hz, 1H), 2.55 (t, J=10.7 Hz, 1H), 2.51-2.38 (m, 2H), 2.43 (s, 6H), 2.32 (ddd, J=14.0, 12.2, 4.6 Hz, 1H), 1.80-1.68 (m, 1H). ESI-MS (m/z): 387 [M+H]⁺. $[\alpha_D^{20}]=-18.6$ (0.54, methanol).

Example 21: Rac-syn-3-(1-(2-Chloro-4-fluorophenethyl)-3-((dimethylamino)methyl)-4-hydroxypiperidin-4-yl)benzamide (32), and Corresponding Hydrochloride Salt (33)

Scheme 10.

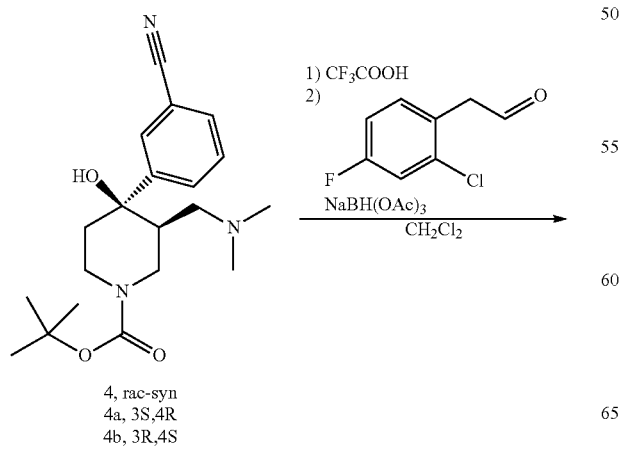

4, rac-syn
4a, 3S,4R
4b, 3R,4S

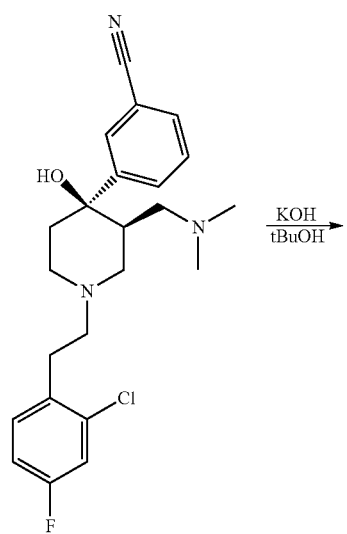

31, rac-syn
31a, 3S,4R
31b, 3R,4S

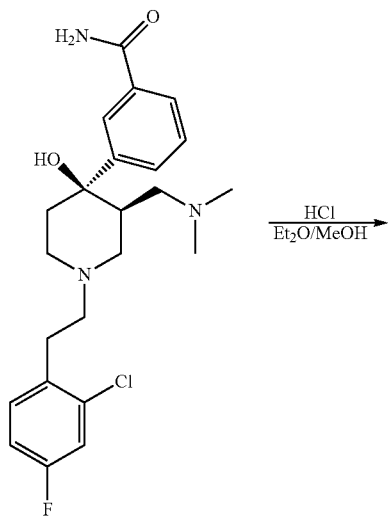

32, rac-syn
32a, 3S,4R (+)-ent
32b, 3R,4S (−)-ent

(a) Rac-syn-3-(1-(2-Chloro-4-fluorophenethyl)-3-((dimethylamino)methyl)-4-hydroxypiperidin-4-yl)benzonitrile (31)

Rac-syn-tert-butyl 4-(3-cyanophenyl)-3-((dimethylamino)methyl)-4-hydroxy piperidine-1-carboxylate (4) (180 mg, 0.50 mmol) was treated with trifluoroacetic acid, and then reacted with 2-(2-chloro-4-fluorophenyl)acetaldehyde (121 mg, 0.70 mmol) using procedure described for compound 23 to produce rac-syn-3-(1-(2-chloro-4-fluorophenethyl)-3-((dimethylamino)methyl)-4-hydroxypiperidin-4-yl)benzonitrile (31) (125 mg, 60% yield). ESI-MS (m/z): 416, 418 [M+H]$^+$.

(b) Rac-syn-3-(1-(2-Chloro-4-fluorophenethyl)-3-((dimethylamino)methyl)-4-hydroxypiperidin-4-yl)benzamide (32)

Rac-syn-3-(1-(2-Chloro-4-fluorophenethyl)-3-((dimethylamino)methyl)-4-hydroxypiperidin-4-yl)benzonitrile (31) (120 mg, 0.29 mmol) was treated with KOH (111 mg, 2.02 mmol) using procedure described for compound 23 to produce rac-syn-3-(1-(2-chloro-4-fluorophenethyl)-3-((dimethylamino)methyl)-4-hydroxypiperidin-4-yl)benzamide (32) (110 mg, 88% yield). ESI-MS (m/z): 434, 436 [M+H]$^+$.

(c) Rac-syn-3-(1-(2-Chloro-4-fluorophenethyl)-3-((dimethylamino)methyl)-4-hydroxypiperidin-4-yl)benzamidehydrochloride (33)

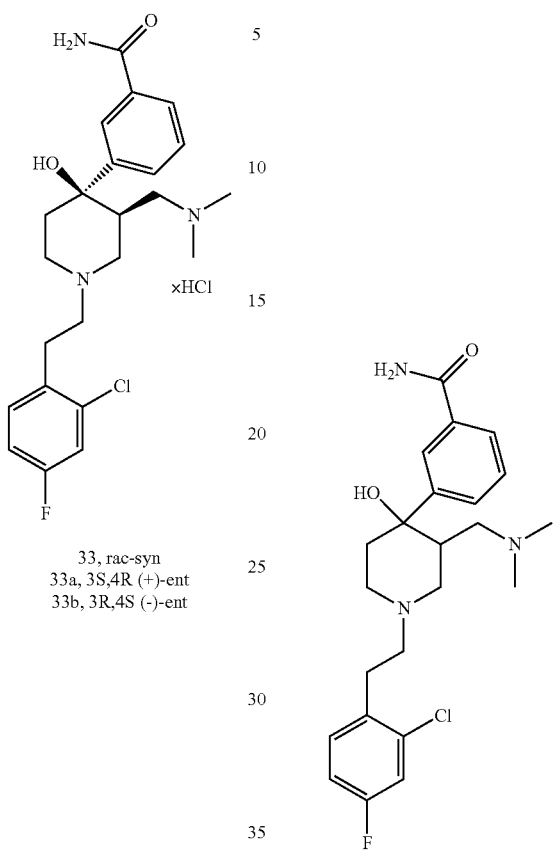

Rac-syn-3-(1-(2-Chloro-4-fluorophenethyl)-3-((dimethylamino)methyl)-4-hydroxypiperidin-4-yl)benzamide (32) (110 mg, 0.25 mmol) was treated with 2M HCl (in diethyl ether) in diethyl ether/methanol (16 mL/0.5 mL) using procedure described for compound 7 to give rac-syn-3-(1-(2-chloro-4-fluorophenethyl)-3-((dimethylamino)methyl)-4-hydroxypiperidin-4-yl)benzamide hydrochloride (33) (98 mg, 82% yield). 300 MHz $^1$H NMR (CD$_3$OD, ppm) 8.10-8.04 (m, 1H), 7.87-7.81 (m, 1H), 7.79-7.72 (m, 1H), 7.56 (dd, J=7.7, 7.7 Hz, 1H), 7.47 (dd, J=8.6, 6.0 Hz, 1H), 7.28 (dd, J=8.6, 2.6 Hz, 1H), 7.10 (ddd, J=8.4, 8.4, 2.6 Hz, 1H), 3.68-3.51 (m, 1H), 3.50-3.36 (m, 1H), 3.35-3.04 (m, 6H), 2.97 (dd, J=13.6, 9.2 Hz, 1H), 2.79-2.65 (m, 1H), 2.65-2.44 (m, 2H), 2.55 (s, 6H), 1.98-1.86 (m, 1H). ESI-MS (m/z): 434, 436 [M+H]$^+$.

Example 22: 3-((3S,4R)-1-(2-Chloro-4-fluorophenethyl)-3-((dimethylamino)methyl)-4-hydroxypiperidin-4-yl)benzamide (32a), and Corresponding Hydrochloride Salt (33a)

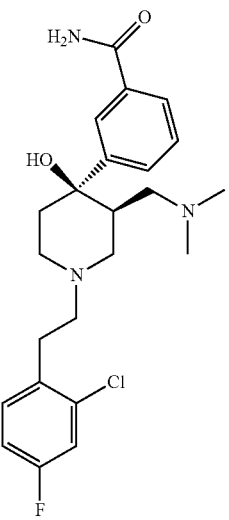 [SMILES: CN(C)C[C@H]1CN(CCc2ccc(F)cc2Cl)CC[C@]1(O)c1cccc(C(N)=O)c1]

(a) 3-((3S,4R)-1-(2-Chloro-4-fluorophenethyl)-3-((dimethylamino)methyl)-4-hydroxypiperidin-4-yl)benzonitrile (31a)

tert-Butyl (3S,4R)-4-(3-cyanophenyl)-3-((dimethylamino)methyl)-4-hydroxypiperidine-1-carboxylate (4a) (150 mg. 0.42 mmol) was treated with trifluoroacetic acid, then reacted with 2-(2-chloro-4-fluorophenyl)acetaldehyde (156 mg, 0.90 mmol) using procedure described for compound 23 to produce 3-((3S,4R)-1-(2-chloro-4-fluorophenethyl)-3-((dimethylamino)methyl)-4-hydroxypiperidin-4-yl)benzonitrile (31a) (110 mg, 63% yield). ESI-MS (m/z): 416, 418 [M+H]$^+$.

(b) 3-((3S,4R)-1-(2-Chloro-4-fluorophenethyl)-3-((dimethylamino)methyl)-4-hydroxypiperidin-4-yl)benzamide (32a)

3-((3S,4R)-1-(2-Chloro-4-fluorophenethyl)-3-((dimethylamino)methyl)-4-hydroxypiperidin-4-yl)benzonitrile (31a) (105 mg, 0.25 mmol) was treated with KOH (97 mg, 1.77 mmol) using procedure described for compound 23 to produce 3-((3S,4R)-1-(2-chloro-4-fluorophenethyl)-3-((dimethylamino)methyl)-4-hydroxypiperidin-4-yl)benzamide (32a) (74 mg, 68% yield). ESI-MS (m/z): 434, 436 [M+H]$^+$.

(c) 3-((3S,4R)-1-(2-Chloro-4-fluorophenethyl)-3-((dimethylamino)methyl)-4-hydroxypiperidin-4-yl)benzamide Hydrochloride (33a)

3-((3S,4R)-1-(2-Chloro-4-fluorophenethyl)-3-((dimethylamino)methyl)-4-hydroxypiperidin-4-yl)benzamide (32a) (72 mg, 0.17 mmol) was treated with 2M HCl (in diethyl ether) in diethyl ether/methanol (10 mL/0.5 mL) using procedure described for compound 7 to produce 3-((3S,4R)-1-(2-chloro-4-fluorophenethyl)-3-((dimethylamino)methyl)-4-hydroxypiperidin-4-yl)benzamide hydrochloride (33a) (65 mg, 77% yield). 400 MHz $^1$H NMR (CD$_3$OD, ppm) 8.10-8.05 (m, 1H), 7.86-7.82 (m, 1H), 7.78-7.76 (m, 1H), 7.56 (dd, J=7.8, 7.8 Hz, 1H), 7.47 (dd, J=8.6, 6.0 Hz, 1H), 7.27 (dd, J=8.6, 2.6 Hz, 1H), 7.10 (ddd, J=8.3, 8.3, 2.6 Hz, 1H), 3.69-3.55 (m, 1H), 3.48-3.36 (m, 1H), 3.29-3.03 (m, 7H), 3.03-2.89 (m, 1H), 2.81-2.67 (m, 1H), 2.64-2.42 (m, 1H), 2.54 (6H, s), 1.97-1.85 (m, 1H). ESI-MS (m/z): 434, 436 [M+H]$^+$. [α$_D^{20}$]=+22.3 (0.56, methanol).

Example 23: 3-((3R,4S)-1-(2-Chloro-4-fluorophenethyl)-3-((dimethylamino)methyl)-4-hydroxypiperidin-4-yl)benzamide (32b), and Corresponding Hydrochloride Salt (33b)

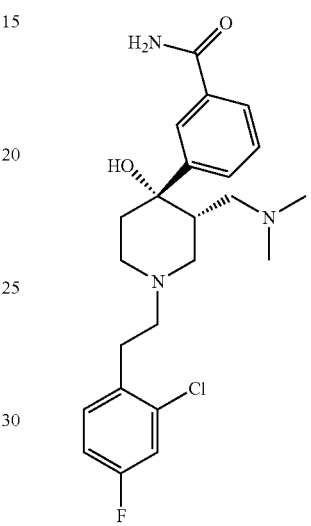

(a) 3-((3R,4S)-1-(2-Chloro-4-fluorophenethyl)-3-((dimethylamino)methyl)-4-hydroxypiperidin-4-yl)benzonitrile (31b)

tert-Butyl (3R,4S)-4-(3-cyanophenyl)-3-((dimethylamino)methyl)-4-hydroxypiperidine-1-carboxylate (4b) (150 mg. 0.42 mmol) was treated with trifluoroacetic acid, then reacted with 2-(2-chloro-4-fluorophenyl)acetaldehyde (144 mg, 0.83 mmol) using procedure described for compound 23 to produce 3-((3R,4S)-1-(2-chloro-4-fluorophenethyl)-3-((dimethylamino)methyl)-4-hydroxypiperidin-4-yl)benzonitrile (31b) (102 mg, 59% yield). ESI-MS (m/z): 416, 418 [M+H]$^+$.

(b) 3-((3R,4S)-1-(2-Chloro-4-fluorophenethyl)-3-((dimethylamino)methyl)-4-hydroxypiperidin-4-yl)benzamide (32b)

3-((3R,4S)-1-(2-Chloro-4-fluorophenethyl)-3-((dimethylamino)methyl)-4-hydroxypiperidin-4-yl)benzonitrile (31b) (100 mg, 0.24 mmol) was treated with KOH (93 mg, 1.69 mmol) using procedure described for compound 23 to produce 3-((3R,4S)-1-(2-chloro-4-fluorophenethyl)-3-((dimethylamino)methyl)-4-hydroxypiperidin-4-yl)benzamide (32b) (66 mg, 63% yield). ESI-MS (m/z): 434, 436 [M+H]$^+$.

(c) 3-((3R,4S)-1-(2-Chloro-4-fluorophenethyl)-3-((dimethylamino)methyl)-4-hydroxypiperidin-4-yl)benzamide Hydrochloride (33b)

3-((3R,4S)-1-(2-Chloro-4-fluorophenethyl)-3-((dimethylamino)methyl)-4-hydroxypiperidin-4-yl)benzamide (32b)

(66 mg, 0.15 mmol) was treated with 2M HCl (in diethyl ether) in diethyl ether/methanol (10 mL/0.5 mL) using procedure described for compound 7 to produce 3-((3R,4S)-1-(2-chloro-4-fluorophenethyl)-3-((dimethylamino)methyl)-4-hydroxypiperidin-4-yl)benzamide hydrochloride (33b) (62 mg, 87% yield). 400 MHz $^1$H NMR (CD$_3$OD, ppm) 8.10-8.05 (m, 1H), 7.84 (d, J=7.8 Hz, 1H), 7.76 (d, J=7.8 Hz, 1H), 7.55 (dd, J=7.8, 7.8 Hz, 1H), 7.47 (dd, J=8.7, 6.0 Hz, 1H), 7.27 (dd, J=8.3, 2.6 Hz, 1H), 7.10 (ddd, J=8.3, 8.3, 2.6 Hz, 1H), 3.68-3.53 (m, 1H), 3.48-3.35 (m, 1H), 3.29-3.03 (m, 7H), 3.02-2.89 (m, 1H), 2.79-2.66 (m, 1H), 2.64-2.42 (m, 1H), 2.54 (6H, s), 1.97-1.85 (m, 1H). ESI-MS (m/z): 434, 436 [M+H]$^+$. [α$_D^{20}$]=−24.2 (0.54, methanol).

Example 24: 3-(1-(Cyclopropylmethyl)-3-((dimethylamino)methyl)-4-hydroxy piperidin-4-yl)benzamide (35), and Corresponding Hydrochloride Salt (36)

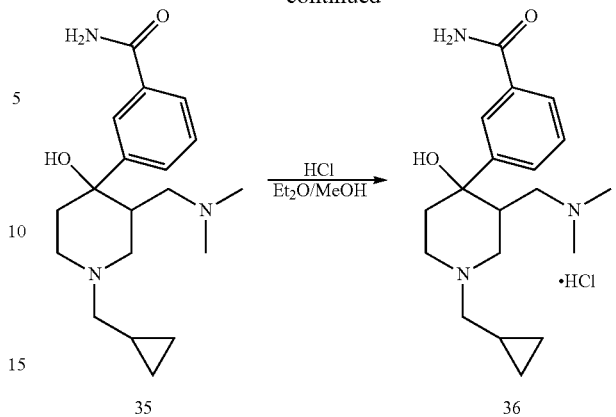

(a) 3-(1-(Cyclopropylmethyl)-3-((dimethylamino)methyl)-4-hydroxypiperidin-4-yl)benzonitrile (34)

tert-Butyl 4-(3-cyanophenyl)-3-((dimethylamino)methyl)-4-hydroxypiperidine-1-carboxylate (4) (220 mg. 0.61 mmol) was treated with trifluoroacetic acid, then reacted with cyclopropanecarbaldehyde (129 mg, 1.84 mmol) using procedure described for compound 23 to produce 3-(1-(cyclopropylmethyl)-3-((dimethylamino)methyl)-4-hydroxypiperidin-4-yl)benzonitrile (34) (84 mg, 44% yield). ESI-MS (m/z): 314 [M+H]$^+$.

(b) 3-(1-(Cyclopropylmethyl)-3-((dimethylamino)methyl)-4-hydroxypiperidin-4-yl)benzamide (35)

3-(1-(Cyclopropylmethyl)-3-((dimethylamino)methyl)-4-hydroxypiperidin-4-yl)benzonitrile (34) (80 mg, 0.26 mmol) was treated with KOH (98 mg, 1.79 mmol) using procedure described for compound 23 to produce 3-(1-(cyclopropylmethyl)-3-((dimethyl amino)methyl)-4-hydroxypiperidin-4-yl)benzamide (35) (60 mg, 71% yield). ESI-MS (m/z): 332 [M+H]$^+$.

(c) 3-(1-(Cyclopropylmethyl)-3-((dimethylamino)methyl)-4-hydroxypiperidin-4-yl)benzamide hydrochloride (36)

3-(1-(Cyclopropylmethyl)-3-((dimethylamino)methyl)-4-hydroxypiperidin-4-yl)benzamide (35) (50 mg, 0.15 mmol) was treated with 2M HCl (in diethyl ether) in diethyl ether/methanol (25 mL/1.0 mL) using procedure described for compound 7 to give 3-(1-(cyclopropylmethyl)-3-((dimethylamino)methyl)-4-hydroxypiperidin-4-yl)benzamide hydrochloride (36) (40 mg, 72% yield). 300 MHz $^1$H NMR (CD$_3$OD, ppm) 8.10-8.03 (m, 1H), 7.87-7.81 (m, 1H), 7.79-7.71 (m, 1H), 7.55 (dd, J=7.7, 7.7 Hz, 1H), 3.85-3.73 (m, 1H), 3.68-3.56 (m, 1H), 3.42-3.22 (m, 2H), 3.19-3.05 (m, 2H), 2.85-2.66 (m, 2H), 2.65-2.49 (m, 1H), 2.48-2.19 (m, 1H), 2.35 (s, 6H), 2.00-1.90 (m, 1H), 1.30-1.19 (m, 1H), 0.85-0.77 (m, 2H), 0.55-0.46 (m, 2H). ESI-MS (m/z): 332 [M+H]$^+$.

Scheme 11.

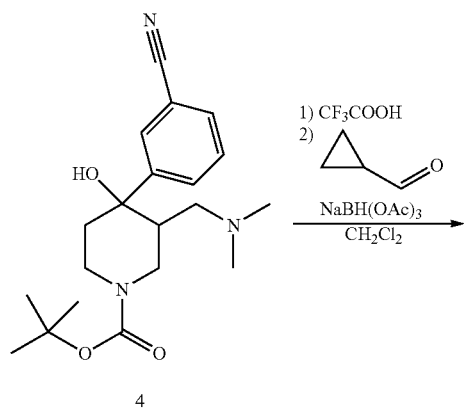

4

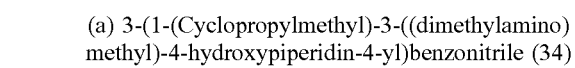

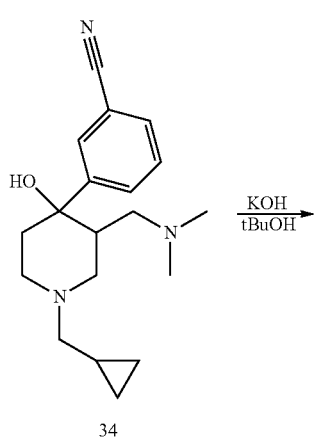

34

Example 25

(+)-Ent-A-syn-3-(3-((Dimethylamino)methyl)-4-hydroxy-1-(4-hydroxyphenethyl)-piperidin-4-yl)benzamide (38a), and Corresponding Hydrochloride Salt (39a)

(−)-Ent-B-syn-3-(3-((Dimethylamino)methyl)-4-hydroxy-1-(4-hydroxyphenethyl)-piperidin-4-yl)benzamide (38b), and Corresponding Hydrochloride Salt (39b)

Scheme 12 (absolute stereochemistry not implied).

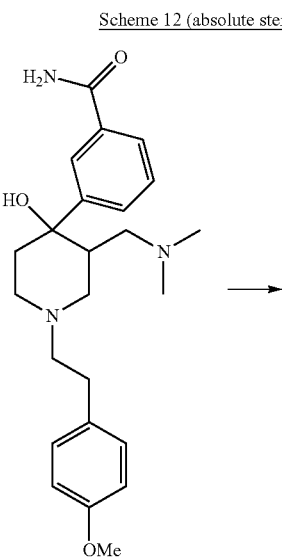

10e, rac-syn

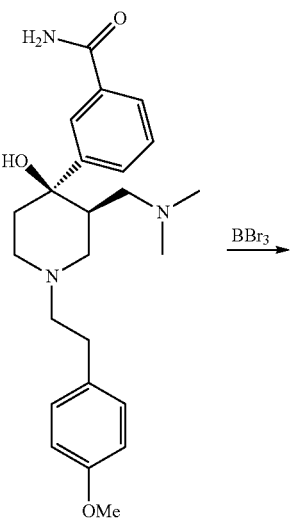

37a, (+)-Ent-A-syn
37b, (−)-Ent-B-syn

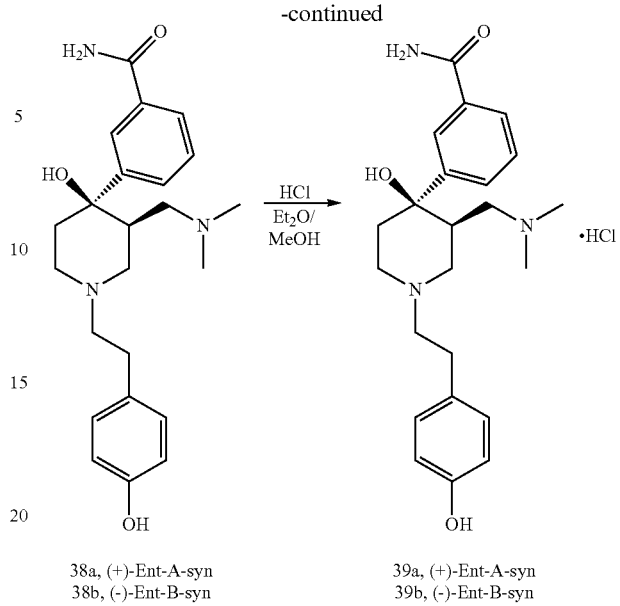

38a, (+)-Ent-A-syn
38b, (−)-Ent-B-syn 39a, (+)-Ent-A-syn
39b, (−)-Ent-B-syn 3-(3-((Dimethylamino)methyl)-4-hydroxy-1-(4-methoxyphenethyl)piperidin-4-yl)benzamide (10e) was separated into stereoisomers on chiral stationary phase chromatography using Daicel CHIRALPAK® ID (250 mm×30 mm) column and Hex/IPA (4:1)+0.1% $NH_2CH_2CH_2OH$ as mobile phase on Shimadzu LC-8A: Rt stereoisomer (+) (37a)=35 min, Rt stereoisomer (−) (37b)=40 min at 40 mL/min flow rate.

(+)-Ent-A-syn-3-(3-((Dimethylamino)methyl)-4-hydroxy-1-(4-hydroxyphenethyl)-piperidin-4-yl)benzamide Hydrochloride (39a)

(a) (+)-Ent-A-syn-3-(3-((Dimethylamino)methyl)-4-hydroxy-1-(4-hydroxyphenethyl)-piperidin-4-yl)benzamide (38a)

A $BBr_3$ solution (1.0 M in $CH_2Cl_2$) (3.64 mL, 3.64 mmol) was added to a solution of (+)-Ent-A-syn-3-(3-((dimethylamino)methyl)-4-hydroxy-1-(4-methoxyphenethyl)piperidin-4-yl)benzamide (37a) (150 mg, 0.36 mmol) in $CH_2Cl_2$ (8 mL) at 0° C. temperature. The reaction mixture was stirred at ambient temperature for 3 hours, then methanol (10 mL) was added and the resulting suspension was stirred for 30 min. Volatiles were removed, and the residue was purified flash column chromatography using gradient elution from $CH_2Cl_2$/methanol (99:1) to $CH_2Cl_2$/methanol (9:1) to give (+)-Ent-A-syn-3-(3-((dimethylamino) methyl)-4-hydroxy-1-(4-hydroxyphenethyl)-piperidin-4-yl)benzamide (38a) (125 mg, 86% yield). ESI-MS (m/z): 398 [M+H]$^+$.

(b) (+)-Ent-A-syn-3-(3-((Dimethylamino)methyl)-4-hydroxy-1-(4-hydroxyphenethyl)-piperidin-4-yl)benzamide Hydrochloride (39a)

(+)-Ent-A-syn-3-(3-((Dimethylamino)methyl)-4-hydroxy-1-(4-hydroxyphenethyl)-piperidin-4-yl)benzamide (38a) (125 mg, 0.31 mmol) was treated with 2M HCl (in diethyl ether) in diethyl ether/methanol (3 mL/2 mL) using procedure described for compound 7 to produce (+)-Ent-A-syn-3-(3-((dimethylamino)methyl)-4-hydroxy-1-(4-hydroxyphenethyl)-piperidin-4-yl)benzamide hydrochloride (39a) (136 mg, 100% yield). 400 MHz $^1$H NMR (CD$_3$OD, ppm) 8.14-8.09 (m, 1H), 7.89-7.84 (m, 1H), 7.82-7.75 (m, 1H), 7.59 (dd, J=7.7, 7.7 Hz, 1H), 7.22-7.14 (m, 2H), 6.82-6.73 (m, 2H), 4.10-4.02 (m, 1H), 3.74-3.65 (m, 1H), 3.56-3.38 (m, 4H), 3.26-3.08 (m, 4H), 2.84-2.72 (m, 2H), 2.76 (s, 3H), 2.59 (s, 3H), 2.05-1.96 (m, 1H). ESI-MS (m/z): 398 [M+H]$^+$. [α$_D^{20}$]=+11.6 (1.00, methanol).

(−)-Ent-B-syn-3-(3-((Dimethylamino)methyl)-4-hydroxy-1-(4-hydroxyphenethyl)-piperidin-4-yl) benzamide Hydrochloride (39b)

(a) (−)-Ent-B-syn-3-(3-((Dimethylamino)methyl)-4-hydroxy-1-(4-hydroxyphenethyl)-piperidin-4-yl) benzamide (38b)

(−)-Ent-B-syn-3-(3-((Dimethylamino)methyl)-4-hydroxy-1-(4-methoxyphenethyl) piperidin-4-yl)benzamide (37b) (160 mg, 0.39 mmol) was treated with BBr$_3$ solution (1.0 M in CH$_2$Cl$_2$) using procedure described for compound 38a to produce (−)-Ent-B-syn-3-(3-((dimethylamino)methyl)-4-hydroxy-1-(4-hydroxyphenethyl)-piperidin-4-yl) benzamide (38b) (135 mg, 87% yield). ESI-MS (m/z): 398 [M+H]$^+$.

(b) (−)-Ent-B-syn-3-(3-((Dimethylamino)methyl)-4-hydroxy-1-(4-hydroxyphenethyl)-piperidin-4-yl) benzamide Hydrochloride (39b)

(−)-Ent-B-syn-3-(3-((Dimethylamino)methyl)-4-hydroxy-1-(4-hydroxyphenethyl)-piperidin-4-yl)benzamide (38b) (125 mg, 0.31 mmol) was treated with 2M HCl (in diethyl ether) in diethyl ether/methanol (3 mL/2 mL) using procedure described for compound 7 to produce (−)-Ent-B-syn-3-(3-((dimethylamino)methyl)-4-hydroxy-1-(4-hydroxyphenethyl)-piperidin-4-yl)benzamide hydrochloride (39b) (128 mg, 94% yield). 400 MHz 1H-NMR (CD$_3$OD, ppm) 8.13-8.09 (m, 1H), 7.89-7.84 (m, 1H), 7.82-7.75 (m, 1H), 7.59 (dd, J=7.7, 7.7 Hz, 1H), 7.22-7.14 (m, 2H), 6.81-6.74 (m, 2H), 4.10-4.02 (m, 1H), 3.74-3.65 (m, 1H), 3.56-3.38 (m, 4H), 3.26-3.08 (m, 4H), 2.84-2.72 (m, 2H), 2.76 (s, 3H), 2.59 (s, 3H), 2.05-1.96 (m, 1H). ESI-MS (m/z): 398 [M+H]$^+$. [α$_D^{20}$]=−10.4 (1.01, methanol).

Example 26: 3-((3S,4R)-3-((Dimethylamino) methyl)-4-hydroxy-1-(2-(thiophen-3-yl)ethyl)piperidin-4-yl)benzamide Hydrochloride (41a), and Corresponding Hydrochloride Salt (42a)

Scheme 13.

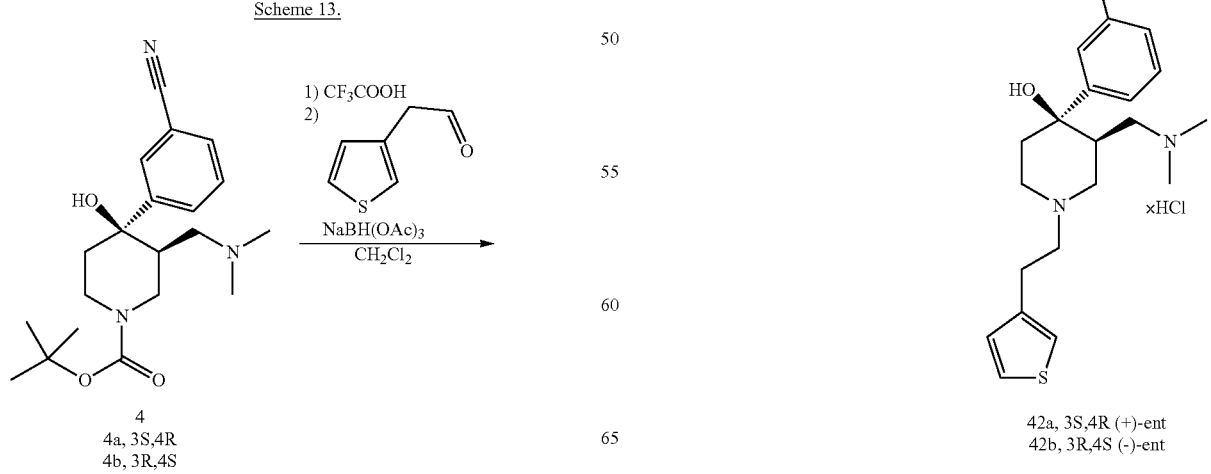

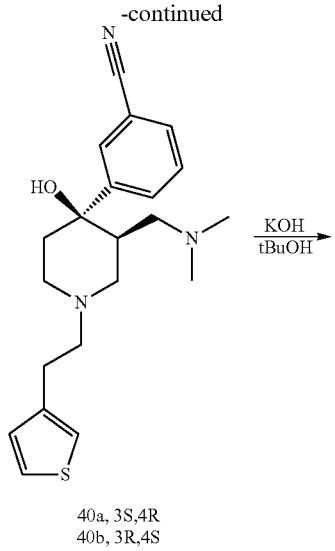

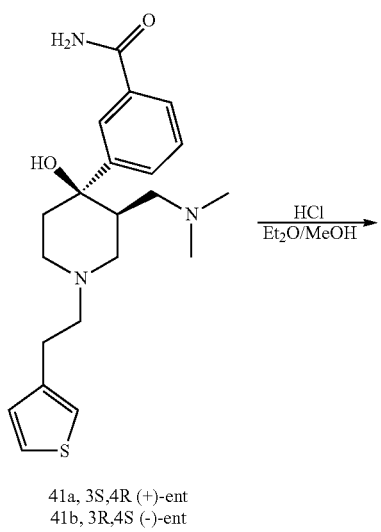

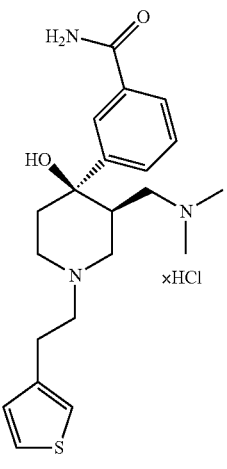

(a) 3-((3S,4R)-3-((Dimethylamino)methyl)-4-hydroxy-1-(2-(thiophen-3-yl)ethyl)piperidin-4-yl)benzonitrile (40a)

tert-Butyl (3S,4R)-4-(3-cyanophenyl)-3-((dimethylamino)methyl)-4-hydroxypiperidine-1-carboxylate (4a) (500 mg, 1.39 mmol) was treated with trifluoroacetic acid, then reacted with 2-(thiophen-3-yl)acetaldehyde (877 mg, 6.95 mmol) using procedure described for compound 23 to produce 3-((3S,4R)-3-((dimethylamino)methyl)-4-hydroxy-1-(2-(thiophen-3-yl)ethyl)piperidin-4-yl)benzonitrile (40a) (420 mg, 82% yield). 300 MHz $^1$H NMR (CDCl$_3$, ppm) 7.96-7.91 (m, 1H), 7.80-7.74 (m, 1H), 7.54 (ddd, J=7.6, 1.4, 1.4 Hz, 1H), 7.46 (dd, J=7.6, 7.6 Hz, 1H), 7.27 (dd, J=4.9, 2.9 Hz, 1H), 7.03 (dd, J=2.9, 1.4 Hz, 1H), 7.00 (dd, J=4.9, 1.4 Hz, 1H), 3.00-2.68 (m, 7H), 2.67-2.47 (m, 1H), 2.36 (dd, J=14.2, 4.4 Hz, 1H), 2.26-2.11 (m, 2H), 2.09 (s, 6H), 2.02-1.80 (m, 1H), 1.73-1.62 (m, 1H). ESI-MS (m/z): 370 [M+H]$^+$.

(b) 3-((3S,4R)-3-((Dimethylamino)methyl)-4-hydroxy-1-(2-(thiophen-3-yl)ethyl)piperidin-4-yl)benzamide (41a)

3-((3S,4R)-3-((Dimethylamino)methyl)-4-hydroxy-1-(2-(thiophen-3-yl)ethyl)piperidin-4-yl)benzonitrile (40a) (550 mg, 1.49 mmol) was treated with KOH (574 mg, 10.24 mmol) using procedure described for compound 23 to afford 3-((3S,4R)-3-((dimethylamino)methyl)-4-hydroxy-1-(2-(thiophen-3-yl)ethyl)piperidin-4-yl)benzamide (41a) (470 mg, 82% yield). 400 MHz $^1$H NMR (CDCl$_3$, ppm) 8.06-8.01 (m, 1H), 7.77-7.68 (m, 2H), 7.45 (dd, J=7.7, 7.7 Hz, 1H), 7.27 (dd, J=4.9, 2.9 Hz, 1H), 7.03 (dd, J=2.9, 1.3 Hz, 1H), 7.00 (dd, J=4.9, 1.3 Hz, 1H), 6.18 (br s, 1H), 5.70 (br s, 1H), 2.95-2.70 (m, 7H), 2.64-2.54 (m, 1H), 2.38 (dd, J=14.0, 4.6 Hz, 1H), 2.30-2.21 (m, 1H), 2.13 (dd, J=14.0, 1.7 Hz, 1H), 2.08 (s, 6H), 2.08-1.97 (m, 1H), 1.69 (dt, J=13.8, 2.6 Hz, 1H). ESI-MS (m/z): 388 [M+H]$^+$.

(c) 3-((3S,4R)-3-((Dimethylamino)methyl)-4-hydroxy-1-(2-(thiophen-3-yl)ethyl)piperidin-4-yl)benzamide Hydrochloride (42a)

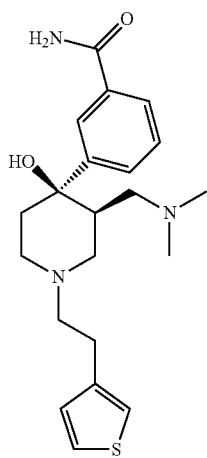

3-((3S,4R)-3-((Dimethylamino)methyl)-4-hydroxy-1-(2-(thiophen-3-yl)ethyl)piperidin-4-yl)benzamide (41a) (447 mg, 1.15 mmol) was treated with 2M HCl (in diethyl ether) in diethyl ether/methanol (25 mL/2 mL) using procedure described for compound 7 to give 3-((3S,4R)-3-((dimethylamino)methyl)-4-hydroxy-1-(2-(thiophen-3-yl)ethyl)piperidin-4-yl)benzamide hydrochloride (42a) (460 mg, 94% yield). 400 MHz $^1$H NMR (CD$_3$OD, ppm) 8.06-8.02 (m, 1H), 7.84-7.79 (m, 1H), 7.75-7.69 (m, 1H), 7.53 (dd, J=7.8, 7.8 Hz, 1H), 7.41 (dd, J=4.9, 2.9 Hz, 1H), 7.26-7.22 (m, 1H), 7.08 (dd, J=4.9, 1.3 Hz, 1H), 3.55-3.44 (m, 1H), 3.40-3.29 (m, 1H), 3.28-3.17 (m, 2H), 3.17-2.96 (m, 4H), 2.79-2.67 (m, 1H), 2.61-2.50 (m, 1H), 2.49-2.23 (m, 2H), 2.36 (s, 6H), 1.92-1.84 (m, 1H). ESI-MS (m/z): 388 [M+H]$^+$. $[\alpha_D^{20}]=+27.2$ (0.54, methanol).

Example 27: 3-((3R,4S)-3-((Dimethylamino)methyl)-4-hydroxy-1-(2-(thiophen-3-yl)ethyl)piperidin-4-yl)benzamide (41b), and Corresponding Hydrochloride Salt (42b)

(a) 3-((3R,4S)-3-((Dimethylamino)methyl)-4-hydroxy-1-(2-(thiophen-3-yl)ethyl)piperidin-4-yl)benzonitrile (40b)

tert-Butyl (3R,4S)-4-(3-cyanophenyl)-3-((dimethylamino)methyl)-4-hydroxy piperidine-1-carboxylate (4b) (260 mg, 0.72 mmol) was treated with trifluoroacetic acid, then reacted with 2-(thiophen-3-yl)acetaldehyde (365 mg, 2.89 mmol) using procedure described for compound 23 to produce 3-((3R,4S)-3-((dimethylamino)methyl)-4-hydroxy-1-(2-(thiophen-3-yl)ethyl)piperidin-4-yl)benzonitrile (40b) (175 mg, 66% yield). 400 MHz $^1$H NMR (CDCl$_3$, ppm) 7.96-7.91 (m, 1H), 7.80-7.74 (m, 1H), 7.54 (ddd, J=7.6, 1.4, 1.4 Hz, 1H), 7.46 (dd, J=7.6, 7.6 Hz, 1H), 7.27 (dd, J=4.9, 2.9 Hz, 1H), 7.04-7.02 (m, 1H), 7.00 (dd, J=4.9, 1.4 Hz, 1H), 3.00-2.68 (m, 7H), 2.67-2.50 (m, 1H), 2.36 (dd, J=14.2, 4.4 Hz, 1H), 2.24-2.12 (m, 2H), 2.09 (s, 6H), 2.02-1.80 (m, 1H), 1.66 (dt, J=13.8, 2.6 Hz, 1H). ESI-MS (m/z): 370 [M+H]$^+$.

(b) 3-((3R,4S)-3-((Dimethylamino)methyl)-4-hydroxy-1-(2-(thiophen-3-yl)ethyl)piperidin-4-yl)benzamide (41b)

3-((3R,4S)-3-((Dimethylamino)methyl)-4-hydroxy-1-(2-(thiophen-3-yl)ethyl)piperidin-4-yl)benzonitrile (40b) (170 mg, 0.46 mmol) was treated with KOH (177 mg, 3.22 mmol) using procedure described for compound 23 to 3-((3R,4S)-3-((dimethylamino)methyl)-4-hydroxy-1-(2-(thiophen-3-yl)ethyl)piperidin-4-yl)benzamide (41b) (140 mg, 79% yield). 400 MHz $^1$H NMR (CDCl$_3$, ppm) 8.06-8.01 (m, 1H), 7.77-7.70 (m, 2H), 7.45 (dd, J=7.7, 7.7 Hz, 1H), 7.27 (dd, J=4.9, 2.9 Hz, 1H), 7.05-7.03 (m, 1H), 7.00 (dd, J=4.9, 1.3 Hz, 1H), 6.16 (br s, 1H), 5.56 (br s, 1H), 2.98-2.73 (m, 7H), 2.68-2.57 (m, 1H), 2.39 (dd, J=14.0, 4.6 Hz, 1H), 2.34-2.25 (m, 1H), 2.14 (dd, J=14.0, 1.7 Hz, 1H), 2.08 (s, 6H), 2.08-1.97 (m, 1H), 1.69 (dt, J=13.8, 2.6 Hz, 1H). ESI-MS (m/z): 388 [M+H]$^+$. $[\alpha_D^{20}]=-17.9$ (1.27, acetone).

93

(c) 3-((3R,4S)-3-((Dimethylamino)methyl)-4-hydroxy-1-(2-(thiophen-3-yl)ethyl)piperidin-4-yl)benzamide Hydrochloride (42b)

3-((3R,4S)-3-((Dimethylamino)methyl)-4-hydroxy-1-(2-(thiophen-3-yl)ethyl) piperidin-4-yl)benzamide (41b) (123 mg, 0.32 mmol) was treated with 2M HCl (in diethyl ether) in diethyl ether/methanol (12 mL/0.5 mL) using procedure described for compound 7 to produce 3-((3R,4S)-3-((dimethylamino)methyl)-4-hydroxy-1-(2-(thiophen-3-yl)ethyl) piperidin-4-yl)benzamide hydrochloride (42b) (115 mg, 86% yield). 300 MHz $^1$H NMR (CD$_3$OD, ppm) 8.06-8.02 (m, 1H), 7.84-7.79 (m, 1H), 7.75-7.69 (m, 1H), 7.53 (dd, J=7.8, 7.8 Hz, 1H), 7.41 (dd, J=4.9, 2.9 Hz, 1H), 7.26-7.21 (m, 1H), 7.08 (dd, J=4.9, 1.3 Hz, 1H), 3.55-3.41 (m, 1H), 3.38-3.27 (m, 1H), 3.25-3.16 (m, 2H), 3.16-3.05 (m, 3H), 3.05-2.93 (m, 1H), 2.79-2.65 (m, 1H), 2.60-2.48 (m, 1H), 2.49-2.21 (m, 2H), 2.33 (s, 6H), 1.93-1.81 (m, 1H). ESI-MS (m/z): 388 [M+H]$^+$.

94

Example 28

(−)-Ent-B-syn 3-[3-Dimethylaminomethyl-4-hydroxy-1-(3-phenyl-propyl)-piperidin-4-yl]-benzamide (43a), and Corresponding Hydrochloride Salt (44a); and (+)-Ent-A-syn-3-[3-Dimethylaminomethyl-4-hydroxy-1-(3-phenyl-propyl)-piperidin-4-yl]-benzamide (43b), and Corresponding Hydrochloride Salt (44b)

Scheme 14 (absolute stereochemistry not implied).

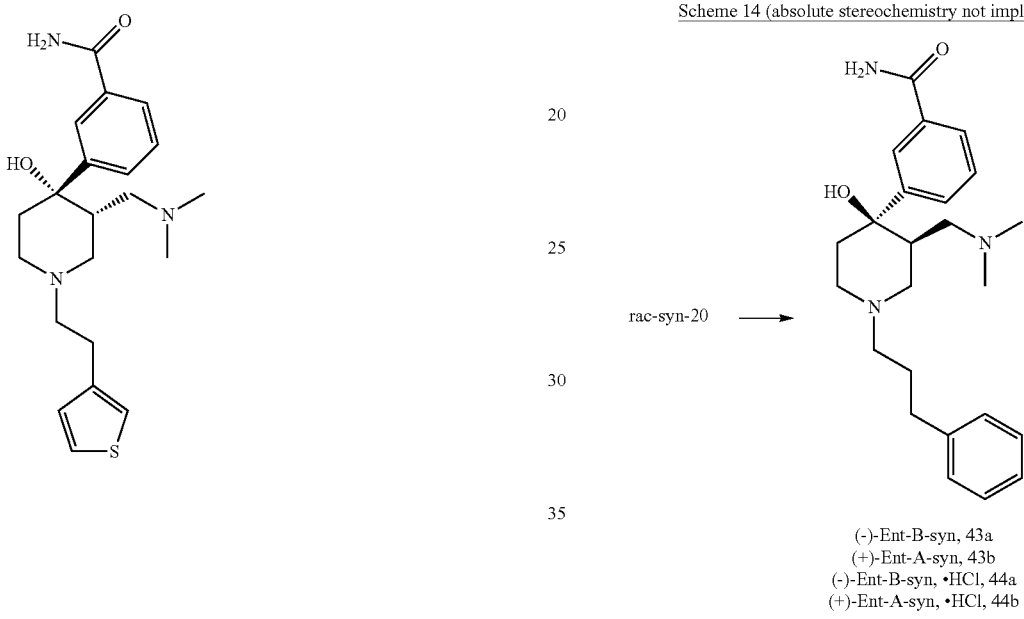

rac-syn-20 →

(−)-Ent-B-syn, 43a
(+)-Ent-A-syn, 43b
(−)-Ent-B-syn, •HCl, 44a
(+)-Ent-A-syn, •HCl, 44b Rac-syn-3-[3-Dimethylaminomethyl-4-hydroxy-1-(3-phenyl-propyl)-piperidin-4-yl]-benzamide (rac-syn-20) was separated into stereoisomers on chiral stationary phase chromatography using (Daicel CHIRALPAK® IC 250 mm×10 mm) column and Hex/IPA (3:1)+0.1% NH$_2$CH$_2$CH$_2$OH as mobile phase on Shimadzu LC-8A: Rt stereoisomer (−) (43a)=45 min, Rt stereoisomer (+) (43b)=49 min at 3 mL/min flow rate.

(−)-Ent-B-syn-3-[3-Dimethylaminomethyl-4-hydroxy-1-(3-phenyl-propyl)-piperidin-4-yl]-benzamide Hydrochloride (44a)

(−)-Ent-B-syn-3-[3-Dimethylaminomethyl-4-hydroxy-1-(3-phenyl-propyl)-piperidin-4-yl]-benzamide (43a) (120 mg, 0.30 mmol) was treated with 2M HCl (in diethyl ether) in diethyl ether (20 mL) using procedure described for compound 7 to produce (−)-Ent-B-syn-3-[3-dimethylaminomethyl-4-hydroxy-1-(3-phenyl-propyl)-piperidin-4-yl]-benzamide hydrochloride (44a) (114 mg, 87% yield). 300 MHz $^1$H NMR (CD$_3$OD, ppm) 8.06-8.00 (m, 1H), 7.85-7.77 (m, 1H), 7.74-7.66 (m, 1H), 7.53 (dd, J=7.8, 7.8 Hz, 1H), 7.36-7.17 (m, 5H), 3.61-3.46 (m, 1H), 3.43-2.95 (m, 5H), 2.82-2.37 (m, 5H), 2.36-2.02 (m, 3H), 2.30 (s, 6H), 1.95-1.82 (m, 1H). ESI-MS (m/z): 396 [M+H]$^+$. [α$_D^{20}$]=−15.0 (0.96, acetone).

(+)-Ent-A-syn-3-[3-Dimethylaminomethyl-4-hydroxy-1-(3-phenyl-propyl)-piperidin-4-yl]-benzamide Hydrochloride (44b)

(+)-Ent-A-syn-3-[3-Dimethylaminomethyl-4-hydroxy-1-(3-phenyl-propyl)-piperidin-4-yl]-benzamide (43b) (120 mg, 0.30 mmol) was treated with 2M HCl (in diethyl ether) in diethyl ether (20 mL) using procedure described for compound 7 to produce (+)-Ent-A-syn-3-[3-dimethylaminomethyl-4-hydroxy-1-(3-phenyl-propyl)-piperidin-4-yl]-benzamide hydrochloride (44b) (117 mg, 89% yield). 300 MHz $^1$H NMR (CD$_3$OD, ppm) 8.05-8.01 (m, 1H), 7.84-7.79 (m, 1H), 7.74-7.68 (m, 1H), 7.52 (dd, J=7.8, 7.8 Hz, 1H), 7.34-7.25 (m, 4H), 7.24-7.18 (m, 1H), 3.62-3.48 (m, 1H), 3.44-3.34 (m, 1H), 3.25-2.97 (m, 4H), 2.79-2.52 (m, 4H), 2.52-2.38 (m, 1H), 2.38-2.05 (m, 3H), 2.30 (s, 6H), 1.93-1.83 (m, 1H). ESI-MS (m/z): 396 [M+H]$^+$. [$\alpha_D^{20}$]=+15.7 (1.24, acetone).

Example 29

(−)-Ent-B-syn-3-(3-dimethylaminomethyl-4-hydroxy-1-phenethyl-piperidin-4-yl)-benzamide (45a), and Corresponding Hydrochloride Salt (46a); and

(+)-Ent-A-syn-3-(3-Dimethylaminomethyl-4-hydroxy-1-phenethyl-piperidin-4-yl)-benzamide (45b), and Corresponding Hydrochloride Salt (46b)

Scheme 15 (absolute stereochemistry not implied).

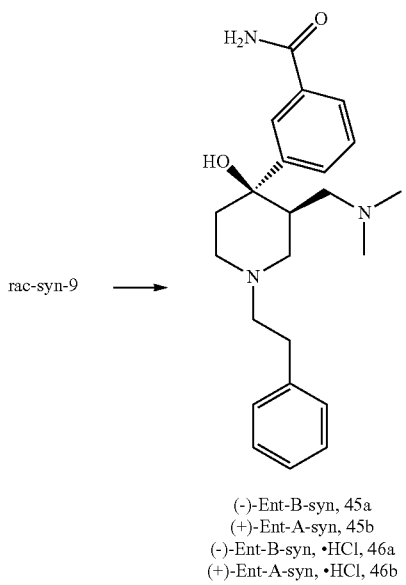

rac-syn-9 →

(−)-Ent-B-syn, 45a
(+)-Ent-A-syn, 45b
(−)-Ent-B-syn, •HCl, 46a
(+)-Ent-A-syn, •HCl, 46b 3-(3-Dimethylaminomethyl-4-hydroxy-1-phenethyl-piperidin-4-yl)-benzamide (rac-syn-9) was separated into stereoisomers on chiral stationary phase chromatography using (Daicel CHIRALPAK® ID 250 mm×30 mm) column and Hex/IPA (85:15)+0.1% NH$_2$CH$_2$CH$_2$OH as mobile phase on Shimadzu LC-8A: Rt stereoisomer (+) (46b)=37 min, Rt stereoisomer (−) (46a)=43 min at 15 mL/min flow rate.

(−)-Ent-B-syn-3-(3-dimethylaminomethyl-4-hydroxy-1-phenethyl-piperidin-4-yl)-benzamide Hydrochloride (46a)

(−)-Ent-B-syn-3-(3-((dimethylamino)methyl)-4-hydroxy-1-phenethylpiperidin-4-yl)benzamide (45a) (45 mg, 0.12 mmol) was treated with 2M HCl (in diethyl ether) in diethyl ether/methanol (20 mL/0.5 mL) using procedure described for compound 7 to produce (−)-Ent-B-syn-3-(3-dimethylaminomethyl-4-hydroxy-1-phenethyl-piperidin-4-yl)-benzamide hydrochloride (46a) (42 mg, 85% yield). 300 MHz $^1$H NMR (CD$_3$OD, ppm) 8.10-8.03 (m, 1H), 7.87-7.81 (m, 1H), 7.79-7.71 (m, 1H), 7.56 (dd, J=7.7, 7.7 Hz, 1H), 7.40-7.22 (m, 5H), 3.83-3.62 (m, 1H), 3.60-3.43 (m, 1H), 3.40-3.07 (m, 6H), 2.98-2.82 (m, 1H), 2.82-2.66 (m, 1H), 2.65-2.33 (m, 2H), 2.48 (s, 6H), 2.00-1.97 (m, 1H). ESI-MS (m/z): 382 [M+H]$^+$.

(+)-Ent-A-syn-3-(3-dimethylaminomethyl-4-hydroxy-1-phenethyl-piperidin-4-yl)-benzamide hydrochloride (46b)

(+)-Ent-A-syn-3-(3-((dimethylamino)methyl)-4-hydroxy-1-phenethylpiperidin-4-yl)benzamide (45b) (35 mg, 0.09 mmol) was treated with 2M HCl (in diethyl ether) in diethyl ether/methanol (20 mL/0.5 mL) using procedure described for compound 7 to produce (+)-Ent-A-syn-3-(3-dimethylaminomethyl-4-hydroxy-1-phenethyl-piperidin-4-yl)-benzamide hydrochloride (46b) (34 mg, 89% yield). 300 MHz $^1$H NMR (CD$_3$OD, ppm) 8.10-8.03 (m, 1H), 7.87-7.81 (m, 1H), 7.79-7.71 (m, 1H), 7.56 (dd, J=7.7, 7.7 Hz, 1H), 7.40-7.22 (n, 5H), 3.83-3.62 (m, 1H), 3.60-3.43 (m, 1H), 3.40-3.07 (m, 6H), 2.98-2.82 (n, 1H), 2.82-2.66 (m, 1H), 2.65-2.33 (m, 2H), 2.48 (s, 6H), 2.00-1.97 (m, 1H). ESI-MS (m/z): 382 [M+H]. [$\alpha_D^{20}$]=+16.6 (2.62, acetone).

Example 30: Bias Factor of Selected Compounds of the Invention $$\Delta RA = LOG\left(\frac{EMAX_{\beta\text{-}Arr}}{EC50_{\beta\text{-}Arr}}\right) - LOG\left(\frac{EMAX_{G\text{-}Protein}}{EC50_{G\text{-}Protein}}\right)$$

| CMPD_ID; EX # | cAMP EC$_{50}$ (um) | cAMP E$_{max}$ (%) | β-Arrestin EC$_{50}$ (μM) | β-Arrestin E$_{max}$ (%) | ΔRA of compound | Bias Factor (ΔRA of compound relative to ΔRA of DAMGO) × 10 |
|---|---|---|---|---|---|---|
| DAMGO | 0.00 | 108 | 0.06 | 98 | −1.48 | 0.00 |
| Morphine | 0.06 | 119 | 0.31 | 28 | −1.33 | 1.51 |
| (6); Ex 3 | 0.102 | 107 | 2.56 | 40 | −1.83 | −2.89 |
| Ent-A-syn-(6); Ex 4 | 0.163 | 132 | 3.17 | 60 | −1.63 | −0.92 |

-continued

| CMPD_ID; EX # | cAMP EC$_{50}$ (um) | cAMP E$_{max}$ (%) | β-Arrestin EC$_{50}$ (μM) | β-Arrestin E$_{max}$ (%) | ΔRA of compound | Bias Factor (ΔRA of compound relative to ΔRA of DAMGO) × 10 |
|---|---|---|---|---|---|---|
| Ent-B-syn-(6); Ex 4 | 0.463 | 111 | 3.67 | 20 | −1.65 | −1.06 |
| (9); Ex 5 | 0.034 | 118 | 0.83 | 18 | −2.22 | −6.76 |
| (11); Ex 6 | 0.550 | 112 | 10.7 | 37 | −1.77 | −2.31 |
| (13); Ex 7 | | | | | | |
| (15); Ex 8 | 0.067 | 95 | >100 | <10 | nc | |
| (17); Ex 9 | 0.467 | 84 | >100 | <10 | nc | |
| (18); Ex 10 | 0.160 | 103 | 3.1 | 24 | −1.91 | −3.73 |
| (20); Ex 11 | 0.010 | 103 | 0.27 | 14 | −2.28 | −7.37 | nc = not calculated

Example 31: In Vivo Studies

In vivo rat pain model experiments were performed using subcutaneous (SC) administration of morphine as a control drug, or certain exemplary compounds of the invention. Experiments Performed Included:
(a) Dose required for compound to reach the ED$_{80}$ of morphine in the rat tail flick nociceptive pain model;
(b) Accelerating RotaRod;
(c) Gastrointestinal motility;
(d) Respiratory depression (partial pressure of O$_2$ at 30 minutes); and
(e) Conditioned place preference.

Selected results are presented herein.

Figure 2:
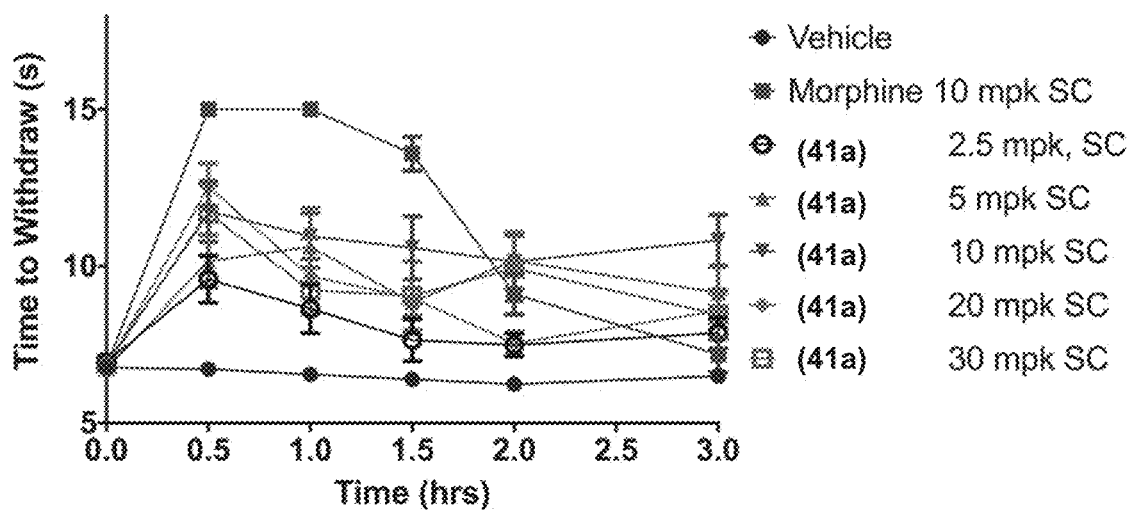
FIG. 2 is a graph illustrating results from a nociceptive analgesia test (rat tail flick, 76° C., N=8) for morphine and illustrative compound (41a). Error bars shown=standard error of the mean.

The ED$_{80}$ for morphine in the rat tail flick nociceptive pain model was reached at a dose of 1 mg/kg morphine. A similar ED$_{80}$ was achieved for illustrative compounds of the invention at doses of 4.5 mg/kg for (23a) (FIG. 1) and 5 mg/kg for (41a) (FIG. 2). Thus, all following studies compared the activity of 1 mg/kg morphine, 4.5 mg/kg (23a), and 5 mg/kg (41a).

Figure 3:
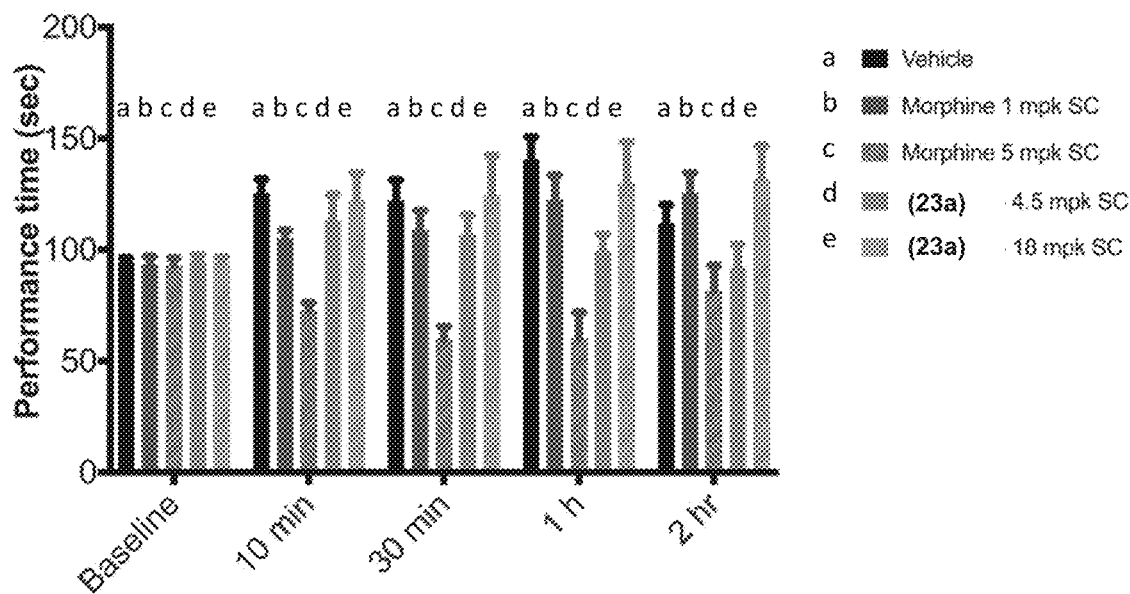
FIG. 3 is a bar graph illustrating results from a test that evaluates sedation (rat accelerating RotaRod, N=8) for morphine and illustrative compound (23a). *$p<0.05$.
Figure 4:
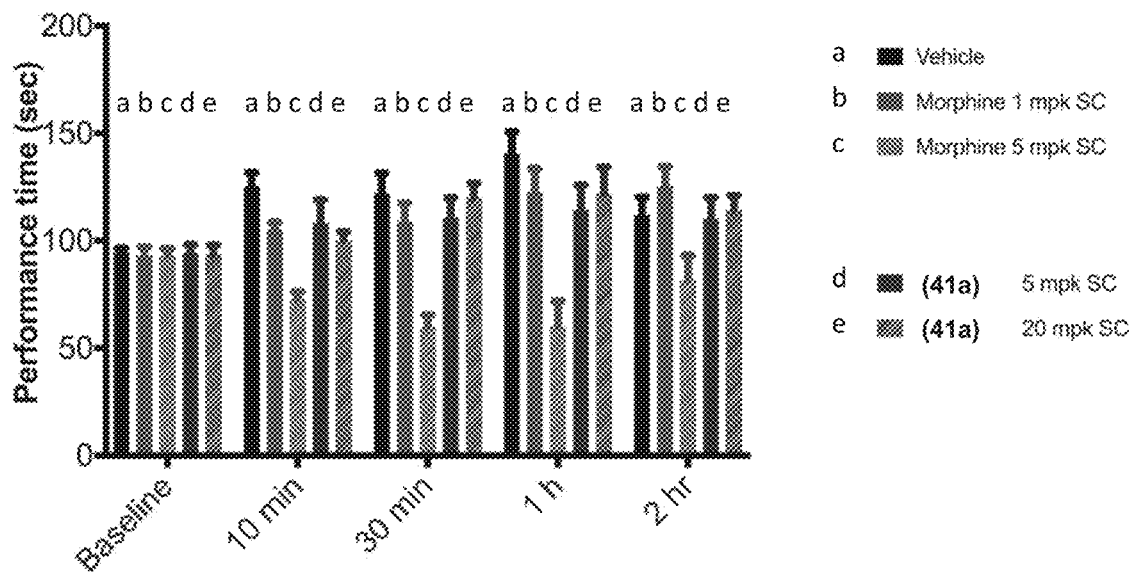
FIG. 4 is a bar graph illustrating results from a test that evaluates sedation (rat accelerating RotaRod, N=8) for morphine and illustrative compound (41a). *$p<0.05$.

In the accelerating RotaRod experiment, morphine showed no sedation at 1 mg/kg, and significant sedation at 5 mg/kg (FIGS. 3-4). (23a) showed no sedation at 4.5 mg/kg or 18 mg/kg (FIG. 3). (41a) showed no sedation at 5 mg/kg or 20 mg/kg (FIG. 4).

Figure 5:
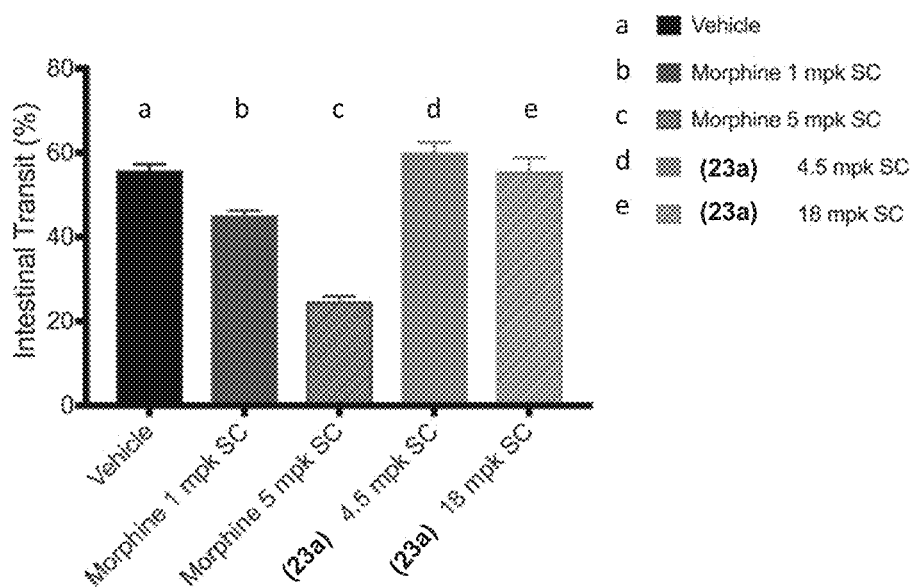
FIG. 5 is a bar graph illustrating results from a gastrointestinal motility test (rat charcoal transit, N=5) for morphine and illustrative compound (23a). *$p<0.05$.
Figure 6:
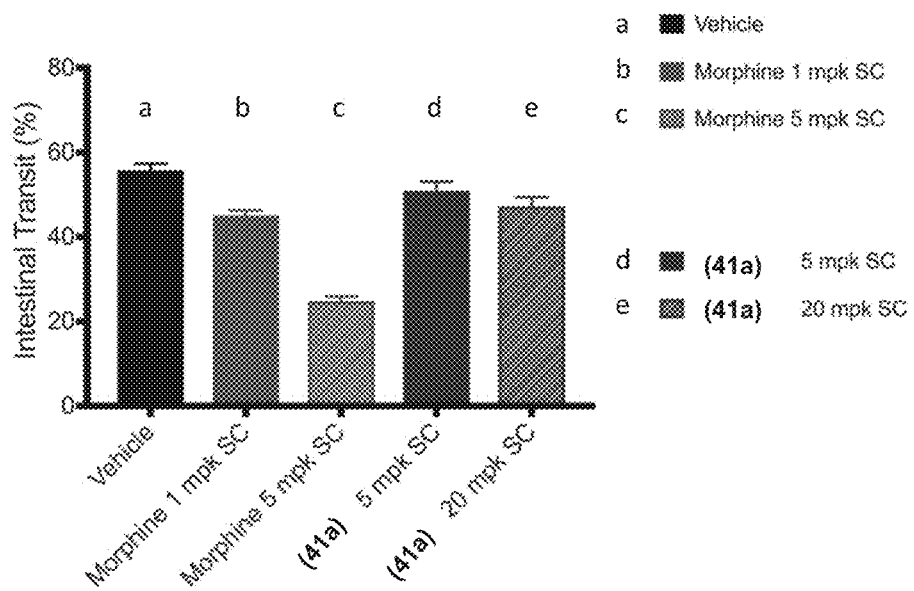
FIG. 6 is a bar graph illustrating results from a gastrointestinal motility test (rat charcoal transit, N=5) for morphine and illustrative compound (41a). *$p<0.05$.

In the gastrointestinal motility experiment, the rats showed small reduction in transit relative to vehicle when dosed with morphine at 1 mg/kg, and significant reduction in transit relative to vehicle when dosed with morphine at 5 mg/kg (FIGS. 5-6). The animals showed no significant reduction in transit relative to vehicle when dosed with (23a) at 4.5 mg/kg, and small reduction in transit relative to vehicle when dosed with (23a) at 18 mg/kg (FIG. 5). The animals showed no significant reduction in transit relative to vehicle when dosed with (41a) at 5 mg/kg or 20 mg/kg (FIG. 6).

Figure 7:
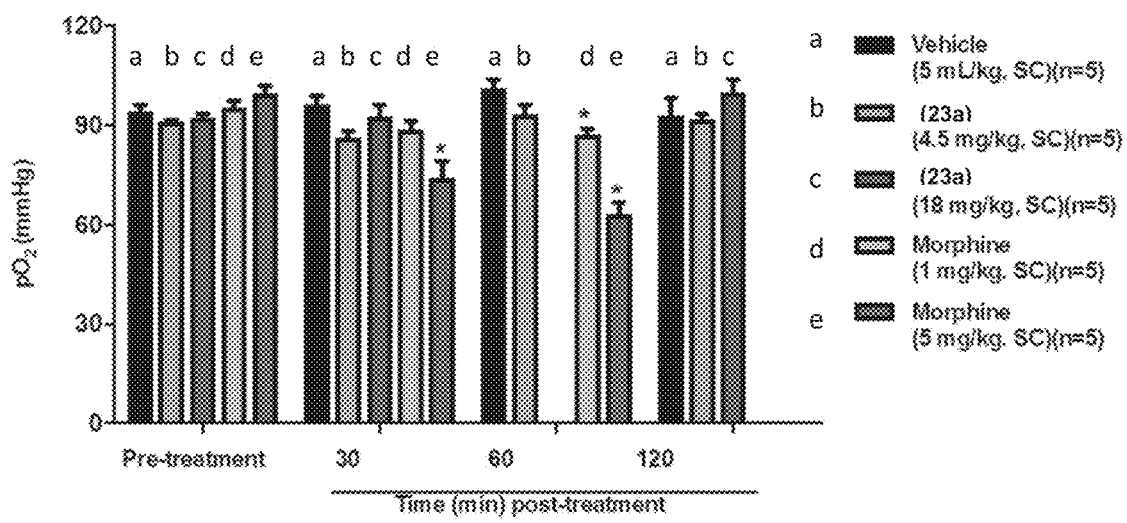
FIG. 7 is a bar graph illustrating results from a respiratory depression test (rat, N=5) for morphine and illustrative compound (23a), as measured by $O_2$ partial pressure. *$p<0.05$.
Figure 8:
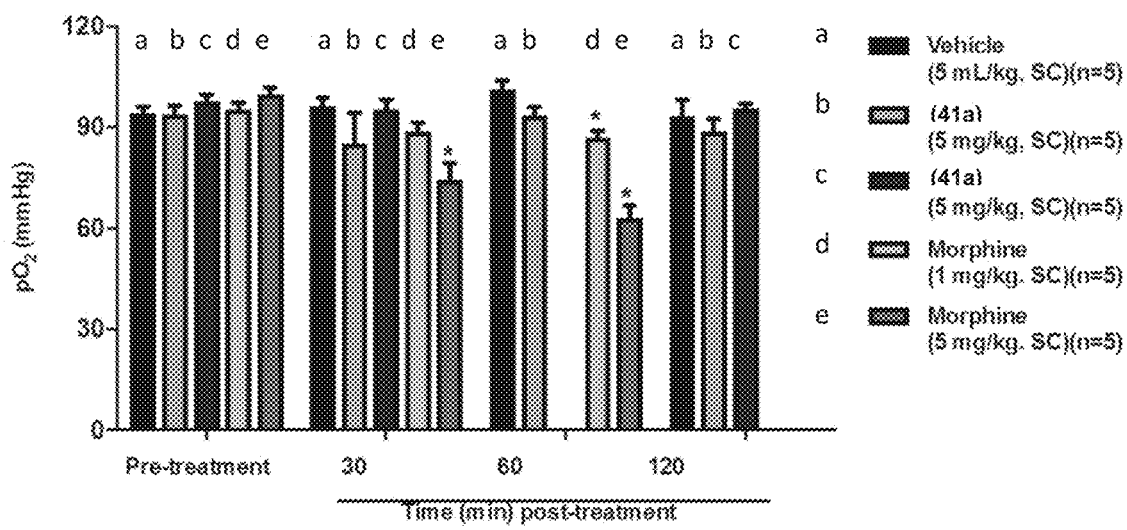
FIG. 8 is a bar graph illustrating results from a respiratory depression test (rat, N=5) for morphine and illustrative compound (41a), as measured by $O_2$ partial pressure. *$p<0.05$.

In the respiratory depression test, partial pressure of O$_2$ was measured at 30 minutes. Vehicle showed a O$_2$ partial pressure of 96 mm Hg under these conditions (FIGS. 7-8). Morphine at a dose of 1 mg/kg showed the same O$_2$ partial pressure as vehicle, and morphine at a dose of 5 mg/kg showed a O$_2$ partial pressure of 74 mm Hg (FIGS. 7-8). (23a) at a dose of 4.5 mg/kg or 18 mg/kg showed the same O$_2$ partial pressure as vehicle (FIG. 7). (41a) at a dose of 5 mg/kg or 20 mg/kg showed the same O$_2$ partial pressure as vehicle (FIG. 8).

Figure 9:
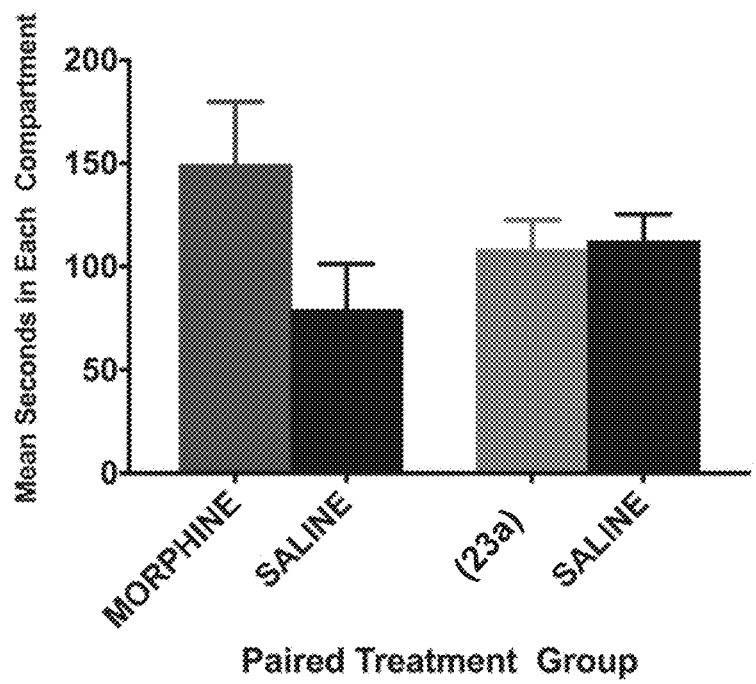
FIG. 9 is a bar graph illustrating results from a conditional placed preference test (rat, N=6-7 per group) for morphine (5 mg/kg SC) and illustrative compound (23a) (16.6 mg/kg SC), as measured by mean time in each compartment. *$p<0.05$.
Figure 10:
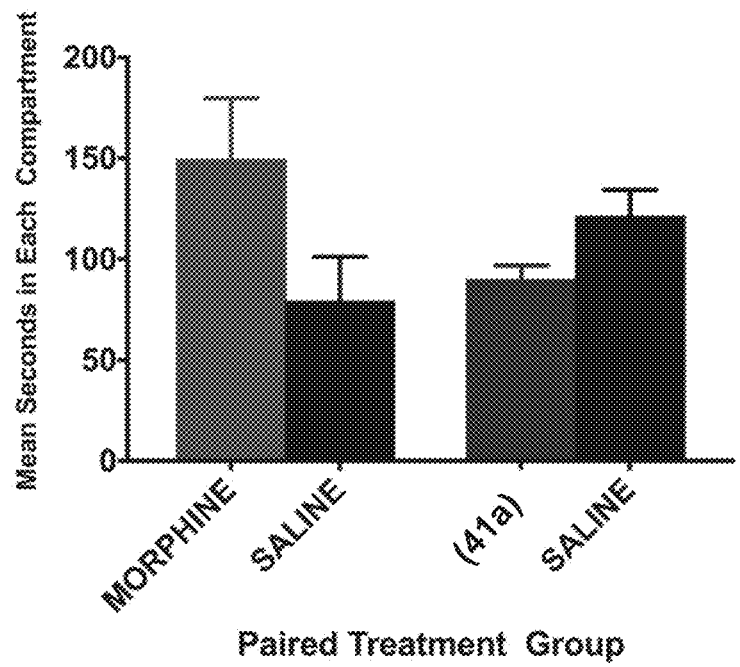
FIG. 10 is a bar graph illustrating results from a conditional placed preference test (rat, N=6-7 per group) for morphine (5 mg/kg SC) and illustrative compound (41a) (18.2 mg/kg SC), as measured by mean time in each compartment. *$p<0.05$.

In the conditioned place preference test, the animals showed significant preference for the morphine chamber over the saline chamber, when dosed with 5 mg/kg morphine (FIGS. 9-10). In contrast, animals dosed at 18 mg/kg (23a) showed no preference for the (23a) chamber over the saline chamber (FIG. 9). Likewise, animals dosed at 20 mg/kg (41a) showed no preference for the (41a) chamber over the saline chamber (FIG. 10).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (I):

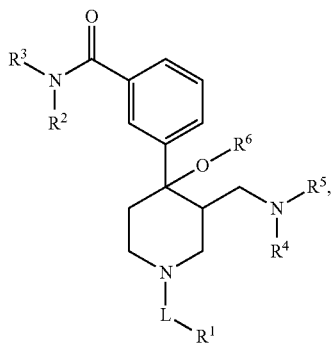

(I)

wherein:

L is selected from the group consisting of —(CZ$^1$Z$^2$)—, —(CZ$^1$Z$^2$—CZ$^1$Z$^2$)—, and —(CZ$^1$Z$^2$—CZ$^1$Z$^2$—CZ$^1$Z$^2$)—;

R$^1$ is selected from the group consisting of

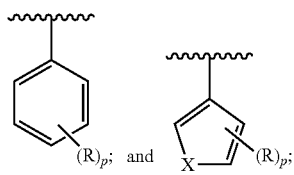

R$^2$ is hydrogen;
R$^3$ is hydrogen;
R$^4$ is selected from the group consisting of methyl and ethyl;
R$^5$ is selected from the group consisting of methyl and ethyl;
R$^6$ is selected from the group consisting of H and C$_1$-C$_6$ alkyl;
each occurrence of Z$^1$ and Z$^2$ is independently selected from the group consisting of hydrogen and methyl;
X is S;
each occurrence of R is independently selected from the group consisting of hydrogen, fluoro, chloro, bromo, iodo, cyano, nitro, hydroxyl, C$_1$-C$_6$ alkoxy, C$_1$-C$_6$ alkyl, substituted C$_1$-C$_6$ alkyl, C$_2$-C$_6$ alkenyl, substituted C$_2$-C$_6$ alkenyl, alkynyl, substituted C$_2$-C$_6$ alkynyl, phenyl, substituted phenyl, —COOR$^7$, and carboxamide;
and
each occurrence of p is independently selected from the group consisting of 0, 1, 2, and 3;
or a salt, solvate, enantiomer, diastereoisomer, or tautomer thereof, and any mixtures thereof.

2. The compound of claim 1, wherein R$^4$ and R$^5$ are methyl.

3. The compound of claim 1, wherein R$^6$ is selected from the group consisting of H and methyl.

4. The compound of claim 1, wherein L is selected from the group consisting of methylene (—CH$_2$—), 1,2-ethylene (—CH$_2$—CH$_2$—), and 1,3-propylene (—CH$_2$—CH$_2$—CH$_2$—).

5. The compound of claim 1, wherein R$^1$ is selected from the group consisting of phenyl, thienyl substituted phenyl, and substituted thienyl.

6. The compound of claim 1, wherein R$^2$ and R$^3$ are H, wherein R$^4$ and R$^5$ are methyl, wherein R$^6$ is selected from the group consisting of H and methyl, wherein L is selected from the group consisting of methylene (—CH$_2$—), 1,2-ethylene (—CH$_2$—CH$_2$—), and 1,3-propylene (—CH$_2$—CH$_2$—CH$_2$—), and wherein R$^1$ is selected from the group consisting of phenyl, thienyl substituted phenyl, and substituted thienyl.

7. The compound of claim 1, wherein the —R$^6$ and —CH$_2$NR$^4$R$^5$ groups have syn relative stereochemistry.

8. The compound of claim 7, which is selected from the group consisting of:

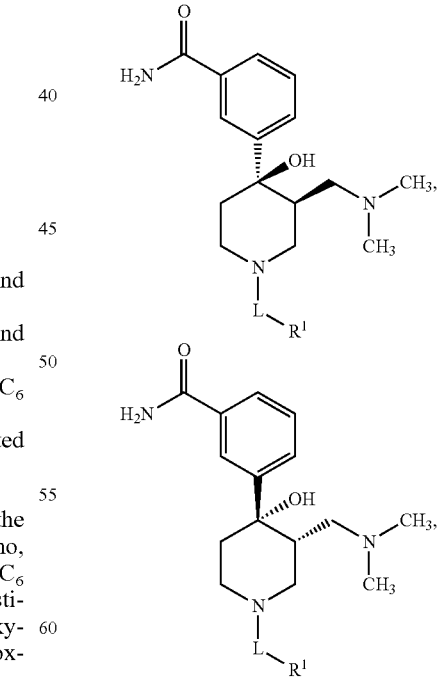

and any mixtures thereof.

9. A compound selected from the group consisting of:
3-(-(2-Chloro-4-fluoro-benzyl)-3-dimethylaminomethyl-4-hydroxy-piperidin-4-yl)-benzamide (6);

(+)-Ent-A-syn-3-(1-(2-chloro-4-fluorobenzyl)-3-((dimethylamino)methyl)-4-hydroxy piperidin-4-yl)benzamide [(+)-Ent-A-syn-(6)];
(−)-Ent-B-syn-3-(1-(2-chloro-4-fluorobenzyl)-3-((dimethylamino)methyl)-4-hydroxy piperidin-4-yl)benzamide [(−)-Ent-B-syn-(6)];
(+)-Ent-A-anti-3-[1-(2-chloro-4-fluorobenzyl)-3-[(dimethylamino)methyl]-4-hydroxypiperidin-4-yl]benzamide [(+)-Ent-A-anti-(6)];
(−)-Ent-B-anti-3-[1-(2-chloro-4-fluorobenzyl)-3-[(dimethylamino)methyl]-4-hydroxypiperidin-4-yl]benzamide [(−)-Ent-B-anti-(6)];
3-(3-Dimethylaminomethyl-4-hydroxy-1-thiophen-3-ylmethyl-piperidin-4-yl)-benzamide (11);
(+)-Ent-A-syn-3-[3-[(dimethylamino)methyl]-4-hydroxy-1-[(thiophen-3-yl)methyl]piperidin-4-yl] benzamide [(+)-Ent-A-syn-(11)];
(−)-Ent-B-syn-3-[3-[(dimethylamino)methyl]-4-hydroxy-1-[(thiophen-3-yl)methyl]piperidin-4-yl] benzamide [(−)-Ent-B-syn-(11)];
(+)-Ent-A-anti-3-[(dimethylamino)methyl]-4-hydroxy-1-[(thiophen-3-yl)methyl]piperidin-4-yl] benzamide [(+)-Ent-A-anti-(11)];
(−)-Ent-B-anti-3-[3-[(dimethylamino)methyl]-4-hydroxy-1-[(thiophen-3-yl)methyl]piperidin-4-yl] benzamide [(−)-Ent-B-anti-(11)];
3-(3-Dimethylaminomethyl-4-hydroxy-1-phenethyl-piperidin-4-yl)-benzamide (9);
(+)-Ent-A-syn-3-[3-[(dimethylamino)methyl]-4-hydroxy-1-(2-phenylethyl)piperidin-4-yl]benzamide (45a);
(−)-Ent-B-syn-3-[3-[(dimethylamino)methyl]-4-hydroxy-1-(2-phenylethyl)piperidin-4-yl]benzamide (45b);
(+)-Ent-A-anti-3-[3-[(dimethylamino)methyl]-4-hydroxy-1-(2-phenylethyl)piperidin-4-yl]benzamide [(+)-Ent-A-anti-(9)];
(−)-Ent-B-anti-3-[3-[(dimethylamino)methyl]-4-hydroxy-1-(2-phenylethyl)piperidin-4-yl]benzamide [(−)-Ent-B-anti-(9)];
3-(1-(2-Chloro-4-fluorophenethyl)-3-((dimethylamino)methyl)-4-hydroxypiperidin-4-yl) benzamide (13);
3-((3S,4R)-1-(2-Chloro-4-fluorophenethyl)-3-((dimethylamino)methyl)-4-hydroxypiperidin-4-yl)benzamide (32a);
3-((3R,4S)-1-(2-Chloro-4-fluorophenethyl)-3-((dimethylamino)methyl)-4-hydroxypiperidin-4-yl)benzamide (32b);
(+)-Ent-A-anti-3-[1-[2-(2-chloro-4-fluorophenyl)ethyl]-3-[(dimethylamino)methyl]-4-hydroxypiperidin-4-yl]benzamide [(+)-Ent-A-anti-(13)];
(−)-Ent-B-anti-3-[1-[2-(2-chloro-4-fluorophenyl)ethyl]-3-[(dimethylamino)methyl]-4-hydroxypiperidin-4-yl]benzamide [(−)-Ent-B-anti-(13)];
3-(3-((Dimethylamino)methyl)-4-hydroxy-1-(4-methoxyphenethyl)piperidin-4-yl)benzamide (17);
(+)-Ent-A-syn-3-(3-((dimethylamino)methyl)-4-hydroxy-1-(4-methoxyphenethyl)piperidin-4-yl)benzamide [(+)-Ent-A-syn-(17)];
(−)-Ent-B-syn-3-(3-((dimethylamino)methyl)-4-hydroxy-1-(4-methoxyphenethyl)piperidin-4-yl)benzamide [(−)-Ent-B-syn-(17)];
(+)-Ent-A-anti-3-(3-((dimethylamino)methyl)-4-hydroxy-1-(4-methoxyphenethyl)piperidin-4-yl)benzamide [(+)-Ent-A-anti-(17)];
(−)-Ent-B-anti-3-(3-((dimethylamino)methyl)-4-hydroxy-1-(4-methoxyphenethyl)piperidin-4-yl)benzamide [(−)-Ent-B-anti-(17)];
3-(3-((Dimethylamino)methyl)-4-hydroxy-1-(4-hydroxyphenethyl)piperidin-4-yl)benzamide (18);
(+)-Ent-A-syn-3-[3-[(dimethylamino)methyl]-4-hydroxy-1-[2-(4-hydroxyphenyl)ethyl] piperidin-4-yl]benzamide (38a);
(−)-Ent-B-syn-3-[3-[(dimethylamino)methyl]-4-hydroxy-1-[2-(4-hydroxyphenyl)ethyl] piperidin-4-yl]benzamide (38b);
(+)-Ent-A-anti-3-[3-[(dimethylamino)methyl]-4-hydroxy-1-[2-(4-hydroxyphenyl)ethyl]piperidin-4-yl]benzamide [(+)-Ent-A-anti-(18)];
(−)-Ent-B-anti-3-[3-(dimethylamino)methyl]-4-hydroxy-1-[2-(4-hydroxyphenyl)ethyl] piperidin-4-yl]benzamide [(−)-Ent-B-anti-(18)];
3-(3-((Dimethylamino)methyl)-4-hydroxy-1-(2-(thiophen-3-yl)ethyl)piperidin-4-yl)benzamide (15);
3-(3S,4R)-3-((Dimethylamino)methyl)-4-hydroxy-1-(2-(thiophen-3-yl)ethyl)piperidin-4-yl)benzamide (41a);
3-((3R,4S)-3-((Dimethylamino)methyl)-4-hydroxy-1-(2-(thiophen-3-yl)ethyl)piperidin-4-yl)benzamide (41b);
(+)-Ent-A-anti-3-[3-[(dimethylamino)methyl]-4-hydroxy-1-[2-(thiophen-3-yl)ethyl]piperidin-4-yl]benzamide [(+)-Ent-A-anti-(15)];
(−)-Ent-B-anti-3-[3-[(dimethylamino)methyl]-4-hydroxy-1-[2-(thiophen-3-yl)ethyl]piperidin-4-yl]benzamide [(−)-Ent-B-anti-(15)];
3-[3-Dimethylaminomethyl-4-hydroxy-1-(3-phenyl-propyl)-piperidin-4-yl]-benzamide (20);
(+)-Ent-A-syn-3-[3-[(dimethylamino)methyl]-4-hydroxy-1-(3-phenylpropyl)piperidin-4-yl]benzamide (44a);
(−)-Ent-B-syn-3-[3-[(dimethylamino)methyl]-4-hydroxy-1-(3-phenylpropyl)piperidin-4-yl]benzamide (44b);
(+)-Ent-A-anti-3-[3-[(dimethylamino)methyl]-4-hydroxy-1-(3-phenylpropyl)piperidin-4-yl]benzamide [(+)-Ent-A-anti-(20)];
(−)-Ent-B-anti-3-[3-[(dimethylamino)methyl]-4-hydroxy-1-(3-phenylpropyl)piperidin-4-yl]benzamide [(−)-Ent-B-anti-(20)];
3-{1-[3-(2-Chloro-4-fluorophenyl)propyl]-3-[(dimethylamino)methyl]-4-hydroxypiperidin-4-yl}benzamide (23);
3-((3S,4R)-1-(3-(2-Chloro-4-fluorophenyl)propyl)-3-((dimethylamino)methyl)-4-hydroxypiperidin-4-yl) benzamide (23a);
3-((3R,4S)-1-(3-(2-Chloro-4-fluorophenyl)propyl)-3-((dimethylamino)methyl)-4-hydroxypiperidin-4-yl) benzamide (23b);
(+)-Ent-A-anti-3-[1-[3-(2-chloro-4-fluorophenyl)propyl]-3-[(dimethylamino)methyl]-4-hydroxypiperidin-4-yl] benzamide [(+)-Ent-A-anti-(23)];
(−)-Ent-B-anti-3-[1-(3-(2-chloro-4-fluorophenyl)propyl)-3-((dimethylamino)methyl)-4-hydroxypiperidin-4-yl) benzamide [(−)-Ent-B-anti-(23)];
or a salt, solvate, enantiomer, diastereoisomer, or tautomer thereof, and any mixtures thereof.

10. A pharmaceutical composition comprising at least one pharmaceutically acceptable carrier and at least one compound of claim 1.

11. A method of treating or ameliorating pain in a subject, the method comprising administering to the subject a therapeutically effective amount of at least one compound of formula (I):

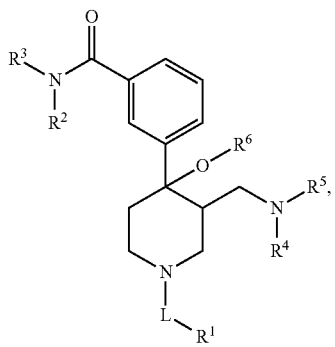

wherein:

L is selected from the group consisting of —(CZ$^1$Z$^2$)—, —(CZ$^1$Z$^2$—CZ$^1$Z$^2$)—, and —(CZ$^1$Z$^2$—CZ$^1$Z$^2$—CZ$^1$Z$^2$)—;

R$^1$ is selected from the group consisting of

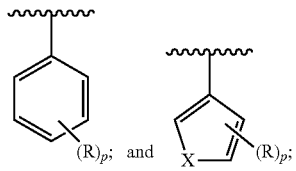

R$^2$ is hydrogen;
R$^3$ is hydrogen;
R$^4$ is selected from the group consisting of methyl and ethyl;
R$^5$ is selected from the group consisting of methyl and ethyl;
R$^6$ is selected from the group consisting of H and C$_1$-C$_6$ alkyl;
each occurrence of Z$^1$ and Z$^2$ is independently selected from the group consisting of hydrogen and methyl;
X is S;
each occurrence of R is independently selected from the group consisting of hydrogen, fluoro, chloro, bromo, iodo, cyano, nitro, hydroxyl, C$_1$-C$_6$ alkoxy, C$_1$-C$_6$ alkyl, substituted C$_1$-C$_6$ alkyl, C$_2$-C$_6$ alkenyl, substituted C$_2$-C$_6$ alkenyl, alkynyl, substituted C$_2$-C$_6$ alkynyl, phenyl, substituted phenyl, —COOR$^7$, and carboxamide; and
each occurrence of p is independently selected from the group consisting of 0, 1, 2, and 3;

or a salt, solvate, enantiomer, diastereoisomer, or tautomer thereof, and any mixtures thereof.

12. A method of treating or ameliorating pain in a subject, the method comprising administering to the subject a therapeutically effective amount of at least one compound is selected from the group of:

3-(-(2-Chloro-4-fluoro-benzyl)-3-dimethylaminomethyl-4-hydroxy-piperidin-4-yl)-benzamide (6);
(+)-Ent-A-syn-3-(1-(2-chloro-4-fluorobenzyl)-3-((dimethylamino)methyl)-4-hydroxy piperidin-4-yl)benzamide [(+)-Ent-A-syn-(6)];
(−)-Ent-B-syn-3-(1-(2-chloro-4-fluorobenzyl)-3-((dimethylamino)methyl)-4-hydroxy piperidin-4-yl)benzamide [(−)-Ent-B-syn-(6)];
(+)-Ent-A-anti-3-[1-(2-chloro-4-fluorobenzyl)-3-[(dimethylamino)methyl]-4-hydroxypiperidin-4-yl]benzamide [(+)-Ent-A-anti-(6)];
(−)-Ent-B-anti-3-[1-(2-chloro-4-fluorobenzyl)-3-[(dimethylamino)methyl]-4-hydroxypiperidin-4-yl]benzamide [(−)-Ent-B-anti-(6)];
3-(3-Dimethylaminomethyl-4-hydroxy-1-thiophen-3-yl-methyl-piperidin-4-yl)-benzamide (11);
(+)-Ent-A-syn-3-[3-[(dimethylamino)methyl]-4-hydroxy-1-[(thiophen-3-yl)methyl]piperidin-4-yl]benzamide [+)-Ent-A-syn-(11)];
(−)-Ent-B-syn-3-[3-[(dimethylamino)methyl]-4-hydroxy-1-[(thiophen-3-yl)methyl]piperidin-4-yl] benzamide [(−)-Ent-B-syn-(11)];
(+)-Ent-A-anti-3-[3-[(dimethylamino)methyl]-4-hydroxy-1-[(thiophen-3-yl)methyl]piperidin-4-yl] benzamide [(+)-Ent-A-anti-(11)];
(−)-Ent-B-anti-3-[3-[(dimethylamino)methyl]-4-hydroxy-1-[(thiophen-3-yl)methyl]piperidin-4-yl] benzamide [(−)-Ent-B-anti-(11)];
(+)-Ent-A-anti-3-[(dimethylamino)methyl]-1-[(5-fluoropyridin-3-yl)methyl]-4-hydroxypiperidin-4-yl]benzamide;
(−)-Ent-B-anti-3-[3-[(dimethylamino)methyl]-1-[(5-fluoropyridin-3-yl)methyl]-4-hydroxypiperidin-4-yl]benzamide;
3-(3-Dimethylaminomethyl-4-hydroxy-1-phenethyl-piperidin-4-yl)-benzamide (9);
(+)-Ent-A-syn-3-[3-[(dimethylamino)methyl]-4-hydroxy-1-(2-phenylethyl)piperidin-4-yl]benzamide (45a);
(−)-Ent-B-syn-3-[3-[(dimethylamino)methyl]-4-hydroxy-1-(2-phenylethyl)piperidin-4-yl]benzamide (45b);
(+)-Ent-A-anti-3-[3-[(dimethylamino)methyl]-4-hydroxy-1-(2-phenylethyl)piperidin-4-yl]benzamide [(+)-Ent-A-anti-(9)];
(−)-Ent-B-anti-3-[3-[(dimethylamino)methyl]-4-hydroxy-1-(2-phenylethyl)piperidin-4-yl]benzamide [(−)-Ent-B-anti-(9)];
3-(1-(2-Chloro-4-fluorophenethyl)-3-((dimethylamino)methyl)-4-hydroxypiperidin-4-yl) benzamide (13);
3-((3S,4R)-1-(2-Chloro-4-fluorophenethyl)-3-((dimethylamino)methyl)-4-hydroxypiperidin-4-yl)benzamide (32a);
3-((3R,4S)-1-(2-Chloro-4-fluorophenethyl)-3-((dimethylamino)methyl)-4-hydroxypiperidin-4-yl)benzamide (32b);
(+)-Ent-A-anti-3-[1-[2-(2-chloro-4-fluorophenyl)ethyl]-3-[(dimethylamino)methyl]-4-hydroxypiperidin-4-yl] benzamide [(+)-Ent-A-anti-(13)];
(−)-Ent-B-anti-3-[1-[2-(2-chloro-4-fluorophenyl)ethyl]-3-[(dimethylamino)methyl]-4-hydroxypiperidin-4-yl] benzamide [(−)-Ent-B-anti-(13)];
3-(3-((Dimethylamino)methyl)-4-hydroxy-1-(4-methoxyphenethyl)piperidin-4-yl)benzamide (17);
(+)-Ent-A-syn-3-(3-((dimethylamino)methyl)-4-hydroxy-1-(4-methoxyphenethyl)piperidin-4-yl)benzamide [(+)-Ent-A-syn-(17)];
(−)-Ent-B-syn-3-(3-((dimethylamino)methyl)-4-hydroxy-1-(4-methoxyphenethyl)piperidin-4-yl)benzamide [(−)-Ent-B-syn-(17)];
(+)-Ent-A-anti-3-(3-((dimethylamino)methyl)-4-hydroxy-1-(4-methoxyphenethyl)piperidin-4-yl)benzamide [(+)-Ent-A-anti-(17)];
(−)-Ent-B-anti-3-(3-((dimethylamino)methyl)-4-hydroxy-1-(4-methoxyphenethyl)piperidin-4-yl)benzamide [(−)-Ent-B-anti-(17)];
3-(3-((Dimethylamino)methyl)-4-hydroxy-1-(4-hydroxyphenethyl)piperidin-4-yl)benzamide (18);

(+)-Ent-A-syn-3-[3-[(dimethylamino)methyl]-4-hydroxy-1-[2-(4-hydroxyphenyl)ethyl] piperidin-4-yl] benzamide (38a);
(−)-Ent-B-syn-3-[3-[(dimethylamino)methyl]-4-hydroxy-1-[2-(4-hydroxyphenyl)ethyl] piperidin-4-yl]benzamide (38b);
(+)-Ent-A-anti-3-[3-[(dimethylamino)methyl]-4-hydroxy-1-[2-(4-hydroxyphenyl)ethyl]piperidin-4-yl] benzamide [(+)-Ent-A-anti-(18)];
(−)-Ent-B-anti-3-[3-(dimethylamino)methyl]-4-hydroxy-1-[2-(4-hydroxyphenyl)ethyl] piperidin-4-yl]benzamide [(−)-Ent-B-anti-(18)];
3-(3-((Dimethylamino)methyl)-4-hydroxy-1-(2-(thiophen-3-yl)ethyl)piperidin-4-yl)benzamide (15);
3-(3S,4R)-3-((Dimethylamino)methyl)-4-hydroxy-1-(2-(thiophen-3-yl)ethyl)piperidin-4-yl)benzamide (41a);
3-((3R,4S)-3-((Dimethylamino)methyl)-4-hydroxy-1-(2-(thiophen-3-yl)ethyl)piperidin-4-yl)benzamide_(41b);
(+)-Ent-A-anti-3-[3-[(dimethylamino)methyl]-4-hydroxy-1-[2-(thiophen-3-yl)ethyl]piperidin-4-yl]benzamide [(+)-Ent-A-anti-(15)];
(−)-Ent-B-anti-3-[3-[(dimethylamino)methyl]-4-hydroxy-1-[2-(thiophen-3-yl)ethyl]piperidin-4-yl]benzamide [(−)-Ent-B-anti-(15)];
3-[3-Dimethylaminomethyl-4-hydroxy-1-(3-phenyl-propyl)-piperidin-4-yl]-benzamide (20);
(+)-Ent-A-syn-3-[3-[(dimethylamino)methyl]-4-hydroxy-1-(3-phenylpropyl)piperidin-4-yl]benzamide (44a);
(−)-Ent-B-syn-3-[3-[(dimethylamino)methyl]-4-hydroxy-1-(3-phenylpropyl)piperidin-4-yl]benzamide (44b);
(+)-Ent-A-anti-3-[3-[(dimethylamino)methyl]-4-hydroxy-1-(3-phenylpropyl)piperidin-4-yl]benzamide [(+)-Ent-A-anti-(20)];
(−)-Ent-B-anti-3-[3-[(dimethylamino)methyl]-4-hydroxy-1-(3-phenylpropyl)piperidin-4-yl]benzamide [(−)-Ent-B-anti-(20)];
3-{1-[3-(2-Chloro-4-fluorophenyl)propyl]-3-[(dimethylamino)methyl]-4-hydroxypiperidin-4-yl}benzamide (23);
3-((3S,4R)-1-(3-(2-Chloro-4-fluorophenyl)propyl)-3-((dimethylamino)methyl)-4-hydroxypiperidin-4-yl)benzamide (23a);
3-((3R,4S)-1-(3-(2-Chloro-4-fluorophenyl)propyl)-3-((dimethylamino)methyl)-4-hydroxypiperidin-4-yl)benzamide (23b);
(+)-Ent-A-anti-3-[1-[3-(2-chloro-4-fluorophenyl)propyl]-3-[(dimethylamino)methyl]-4-hydroxypiperidin-4-yl]benzamide [(+)-Ent-A-anti-(23)];
(−)-Ent-B-anti-3-[1-(3-(2-chloro-4-fluorophenyl)propyl)-3-((dimethylamino)methyl)-4-hydroxypiperidin-4-yl)benzamide [(−)-Ent-B-anti-(23)];

or a salt, solvate, enantiomer, diastereoisomer, or tautomer thereof, and any mixtures thereof.

13. The method of claim 11, wherein the at least one compound is a MOR agonist.

14. The method of claim 11, wherein the at least one compound decreases cyclic adenosine monophosphate (cAMP) levels in the subject.

15. The method of claim 11, wherein the at least one compound does not significantly induce recruitment, binding to, or association with a β-arrestin.

16. The method of claim 11, wherein the at least one compound does not significantly cause at least one side effect selected from the group consisting of tachyphylaxis, respiratory depression, constipation, nausea, emesis, withdrawal, dependence, and addiction.

17. The method of claim 11, wherein the pain comprises at least one of chronic pain, neuropathic pain, nociceptive pain, hyperalgesia, and allodynia.

18. The method of claim 11, wherein the subject is a mammal.

19. The method of claim 18, wherein the mammal is human.

20. The method of claim 12, wherein the at least one compound does not significantly cause at least one side effect selected from the group consisting of tachyphylaxis, respiratory depression, constipation, nausea, emesis, withdrawal, dependence, and addiction.

21. The method of claim 12, wherein the pain comprises at least one of chronic pain, neuropathic pain, nociceptive pain, hyperalgesia, and allodynia.

22. The method of claim 12, wherein the subject is a mammal.

23. The method of claim 22, wherein the mammal is human.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Chemically synthesized
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
```

```
<222> LOCATION: (4)..(4)
<223> OTHER INFORMATION: Tyr methylated on alpha-NH2 and amidated with
      -NHCH2CH2OH on C-terminus

<400> SEQUENCE: 1

Tyr Xaa Gly Xaa
1
```